(12) United States Patent
Seko et al.

(10) Patent No.: US 7,368,444 B2
(45) Date of Patent: May 6, 2008

(54) N-CARBAMOYL NITROGEN-CONTAINING FUSED RING COMPOUNDS AND DRUGS CONTAINING THESE COMPOUNDS AS THE ACTIVE INGREDIENT

(75) Inventors: Takuya Seko, Osaka (JP); Seishi Katsumata, Mishima-gun (JP); Masashi Kato, Mishima-gun (JP); Jun-ichiro Manako, Mishima-gun (JP); Kazuyuki Ohmoto, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 365 days.

(21) Appl. No.: 10/504,422

(22) PCT Filed: Feb. 13, 2003

(86) PCT No.: PCT/JP03/01481

§ 371 (c)(1),
(2), (4) Date: Aug. 13, 2004

(87) PCT Pub. No.: WO03/068753

PCT Pub. Date: Aug. 21, 2003

(65) Prior Publication Data

US 2005/0101600 A1    May 12, 2005

(30) Foreign Application Priority Data

Feb. 14, 2002    (JP) ............... 2002-36340

(51) Int. Cl.
| | |
|---|---|
| C07D 223/16 | (2006.01) |
| C07D 225/06 | (2006.01) |
| C07D 401/12 | (2006.01) |
| C07D 405/12 | (2006.01) |
| C07D 409/12 | (2006.01) |
| C07D 413/12 | (2006.01) |
| C07D 417/12 | (2006.01) |
| C07D 471/04 | (2006.01) |
| C07D 495/04 | (2006.01) |
| A61K 31/395 | (2006.01) |
| A61K 31/55 | (2006.01) |
| A61K 31/553 | (2006.01) |
| A61P 1/00 | (2006.01) |
| A61P 1/04 | (2006.01) |
| A61P 1/16 | (2006.01) |
| A61P 1/18 | (2006.01) |
| A61P 43/00 | (2006.01) |

(52) U.S. Cl. .............. 514/212.07; 514/63; 514/213.01; 540/487; 540/523; 540/593

(58) Field of Classification Search .............. 514/63, 514/212.07, 213.01; 540/487, 523, 593

See application file for complete search history.

(56) References Cited

U.S. PATENT DOCUMENTS

| | | | | |
|---|---|---|---|---|
| 3,346,565 A | 10/1967 | Testa et al. | ............... | 260/239.3 |
| 3,395,150 A | 7/1968 | Krapcho | ............... | 260/268 |
| 3,458,498 A | 7/1969 | Koo et al. | ............... | 260/239 |
| 3,516,987 A | 6/1970 | Koo et al. | ............... | 260/239 |
| 3,542,760 A | 11/1970 | Koo et al. | ............... | 260/239 |
| 3,748,321 A | 7/1973 | Krapcho et al. | ............... | 260/239 |
| 3,960,876 A | 6/1976 | Curran | ............... | 260/294.8 C |
| 4,029,667 A | 6/1977 | Curran | ............... | 260/294.8 C |

FOREIGN PATENT DOCUMENTS

| | | |
|---|---|---|
| FR | 1473839 A | 3/1967 |
| GB | 1193534 A | 6/1970 |
| WO | WO 01/32610 A1 | 5/2001 |
| WO | WO 03/030937 A1 | 4/2003 |

OTHER PUBLICATIONS

Khanna, J.M. et al, Agents Acting on the Central Nervous System. X. 1-Substituted 3-Phenyll-2,2,3,4.5-tetrahydro-1H-1benzazepines, Journal of Medicinal Chemistry, 1967, No. 395, vol. 10, pp. 944 to 945.

Beattle, Doreen E. et al., 5,6,7,8- Tetrahydroquinolines.5. Antiulcer and Antisecretory Activity of 5,6,7,8-Tetrahydroquinolinethioureas and Related heterocycles, Journal of Medicinal Chemistry, 1977, vol. 20, No. 5, pp. 718 to 721.

Ishihara, Yuji et al., Regioselective Friedel-Crafts Acylation of 1,2,3,4-Tetrahydroquinoline and Related Nitrogen Heterocycles: Effects of NH Protective Groups and Ring Size, J. Chem. Soc. Perkin Trans., 1, 1992, vol. 24, pp. 3401 to 3406.

(Continued)

Primary Examiner—Brenda L Coleman
(74) Attorney, Agent, or Firm—Sughrue Mion, PLLC

(57) ABSTRACT

The present invention relates to the compound presented by formula (I)

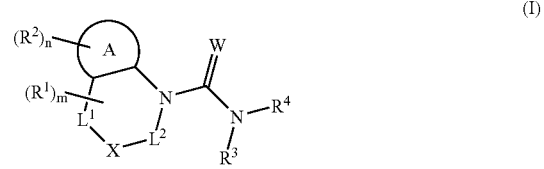

(I)

(wherein all symbols in formula (I) are the same mean as the description shown in the specification.), mitocondorial benzogeazepin receptor (MBR) antagonist comprising the compound, the preventive and/or treatment medicine against diseases caused by stress of which an active ingredient is the compound.

Since the compound represented by formula (I) has MBR antagonistic activity, and controls the production of neurosteroid, it is useful as the preventive and/or treatment medicine against diseases caused by stress.

4 Claims, No Drawings

OTHER PUBLICATIONS

Yanagida, A. Jossang et al., Derivatives of 2,3,4,5-tetrahydroo-1H-pyriodo[3,2-b] azapine and their corresponding lactams. II. Synthesis and pharmacological study on their psychotropic activity, Farmaco, Edizione Scientifica, 1979, vol. 34, No. 1, pp. 26 to 35.

Yanagida, A. Jossang et al., Derivatives of tetrahydropyrido azepines and tetrahydropyridoazepineones. I. Derivatives of 2,3,4,5-tetrahydro-1H-pyrido[3,2-b] azepine and the corresponding lactam, Farmaco, Edizione Scientifica, 1978, vol. 33, No. 12, pp. 984 to 991.

Testa, E. et al., Substances active on the nervous system. XXXVIII. Synthesis of 5-phenyl-3,5-dihydro-4,1-benzoazepin-2(1H)-ones and 5-phenyl.2.3.5-tetrahydro-4,1-benzoxazepines, Farmaco(Pavia), Ed. Sci., 1963, vol. 18, No. 11, pp. 815 to 827.

Dodd, Rober H. et al., Modifications of Mitochondrial Benzodiazephine Receptor Numbers in Stressful Situations, Peripher. Benzodiazepine Recept., 1993, pp. 187 to 207.

N-CARBAMOYL NITROGEN-CONTAINING FUSED RING COMPOUNDS AND DRUGS CONTAINING THESE COMPOUNDS AS THE ACTIVE INGREDIENT

This is a national stage entry under 35 U.S.C. § 371 of PCT/JP03/01481 filed Feb. 13, 2003

TECHNICAL FIELD

The present invention relates to condensed ring compound containing N-carbamoyl nitrogen and pharmaceutically acceptable salt thereof.

In detail, the present invention relates to
(1) a compound represented by formula (I)

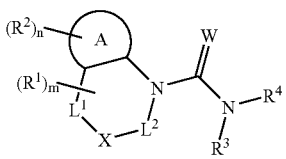

(I)

wherein all symbols represent the same meanings as the postscript or pharmaceutically acceptable salt thereof,
(2) MBR antagonist comprising the compound represented by formula (I) or pharmaceutically acceptable salt thereof as active ingredient,
(3) a manufacturing method of the compound represented by formula (I) and pharmaceutically acceptable salt thereof, and
(4) a preventive and/or treatment medicine for diseases attributable to stress, which comprises the compound represented by formula (I) as an active ingredient.

BACKGROUND ART

In 1977, mitocondorial benzogeazepin receptor (hereafter, it is abbreviated as MBR.) was identified as a receptor that is different from a benzodiazepine binding site in $GABA_A$ receptor to which benzodiazepines bind ("*Science* 198, 849-851, 1977"; "*Proc. Natl. Acad. Sci.*, 89, 3805-3809, 1977"), it has been reported to take part in steroid synthesis, the differentiation and proliferation of cell, and the immune function modulate, etc. though a physiological function is not necessarily clarified. In peripheral tissue, there are MBR in immune system cells such as red blood cell, platelet, monocyte, and macrophages beside adrenal cortex, heart, smooth muscle, kidney, lungs, testis, and in plexus chorioideus, pineal body, olfactory bulb, cerebral cortex, and hippocampus, etc. of central nervous system. Expressing cells in central nervous system has been known to be glia cells mainly, it may be used as a marker of gliosis so that the expression may increase along with the neurodegenerative diseases such as alzheimer's disease, cerebral ischemia, multiple sclerosis, and huntington's disease, etc.

It has been reported that when exposed to chronic stressors, morphologic changes like neuronal death in CA3 field and the shrinkage of dendrite, etc. is admitted in hippocampus and that the number of glial fibrillary acidic protein positive cells increases (*Stress*, 3, 275-284, 2000). It has been suggested that the activation of MBR could happen in glia cells at stress.

There are MBR in mitochondrial outer membrane, which transports cholesterol from intracellular to the internal membrane of mitochondria that is the active site of P-450 scc. Steroid synthesized in encephalon is called as neurosteroid, cholesterol, which is the steroid precursor, is converted into pregnenolone with side chain cleavage enzyme P-450 scc in the first stage of steroidogenesis system. However, it has been presented that this transport process rather than in the metabolism by P-450 scc is a limiting in the steroid production system. It has been thought that the content of neurosteroid in encephalon can be adjusted if the function of MBR can be adjusted. Actually, it has been reported that a diazepam binding inhibitory protein (diazepam binding inhibitor; hereafter, it might be abbreviated as DBI.) identified as an endogenous ligand of MBR and a benzodiazepine binding site in $GABA_A$ receptor promoted the pregnenolone synthesis at mitochondrial fraction from rat brain and glioma cells.

It has been presented that DBI content increases in hippocampus by load sound stressor to rat and DBI density in cerebrospinal fluid of depression patients rises, and is expected that the amount of neurosteroid production could increase at stress. It is reported that the contents of various neurosteroids increase in encephalon by load stressors such as forced swimming, foot shock, expose of carbon dioxide, and restriction as experimental results that proves this.

Neurosteroid adjusts the function of various receptors and ion channels positively or negatively according to the type. For example, though pregnenolone sulfate and dehydroepiandrosterone sulfate control the function of $GABA_A$ receptor, progesterone activats that. And, though pregnenolone sulfate controls functions of AMPA/kainic acid-type glutamate receptor, glycine receptor, and voltage-dependent calcium channel, on the other hand, activates the function of NMDA-type glutamate receptor. Progesterone controls the function of acetylcholine receptor together with glycine receptor. In addition, progesterone is oppositely controled though dehydroepiandrosterone sulfate activates the function of σ receptor. It has been thought that the change of activity of nervous system, immune system, and endocrine system variously adjusted with these nervous systems and the development of diseases related to various stresses could be caused to the collapse of balance between an excitatory signal transmission system and an inhibitory one by the shift of the amount of neurosteroid in encephalon at stress. Considering reports that pregnenolone sulfate reinforces NMDA induced cell death of culture hippocampal neurones and causes late cell death with DNA fragmentation in neural retina cells, the possibility that pregnenolone sulfate also takes part in the degeneration of hippocampus CA3 field at stress partially at least is suggested.

As mentioned above, the inhibition of increase of neurosteroid production via anomalously activated MBR by stressor load and the recovery of balance between the excitatory signal transmission system and the inhibitory one to be normal are effective for the treatment of the disease related to stress. Therefor, it is expected that MBR antagonists could be extremely useful for prevention and treatment of these diseases.

The following compounds are known as 1-carbamoyl-1-benzazepine compound.

(A) It has been described that compounds represented by formula (A)

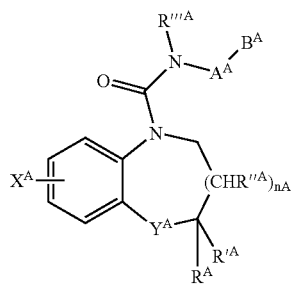

and non-toxic salt thereof are useful as tranquilizer in U.S. Pat. No. 3,748,321 specification.

The following compounds are concretely indicated.

(A-1) 1-(N-2-dimethylaminoethyl-N-methylcarbamoyl)-4-phenyl-2,3,4,5-tetrahydros-1H-1-benzazepine hydrochloride (CAS No. 50832-30-9)

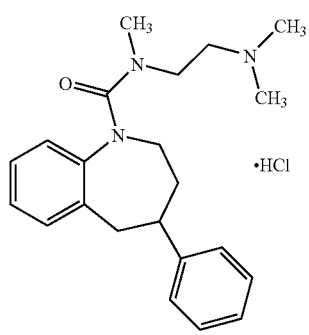

(A-2) N-[2-(dimethylamino)ethyl]-3,4-dihydro-N-methyl-2-phenyl-1,5-benzoxazepine-5-(2H)-carboxamide hydrochloride (CAS No. 50689-70-8)

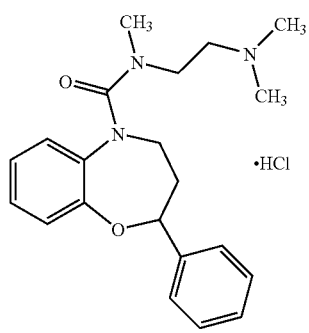

(B) It has been described that compounds represented by formula (B)

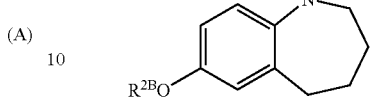

are useful as a diuretic, a hypoglycemic agent, anti-bacteria medicine, and an anticonvulsant in U.S. Pat. No. 3,458,498 specification.

Concretely, the following compounds have been described.

(B-1) 1-cyclohexylcarbamoyl-7-methoxy-2,3,4,5-tetrahydros-1H-1-benzazepine (CAS No. 23605-96-1)

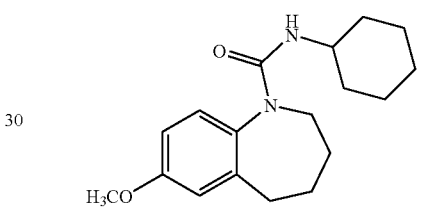

(B-2) 7-methoxy-1-phenylcarbamoyl-2,3,4,5-tetrahydro-1H-1-benzazepine (CAS No. 23573-35-5)

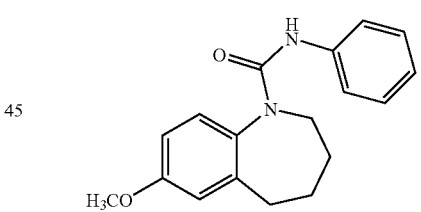

(B-3) 1-butylcarbamoyl-7-methoxy-2,3,4,5-tetrahydro-1H-1-benzazepine (CAS No. 23561-99-1)

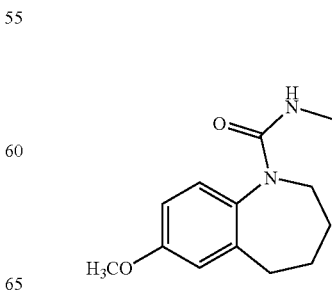

(C) A Compound Represented by Formula (C)

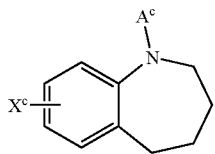
(C)

has been described in FR1473839 specification as a intermediate.

Concretely, the following compounds are indicated.

(C-1) 1-propylcarbamoyl-2,3,4,5-tetrahydro-1H-1-benzazepine (CAS No. 17422-51-4)

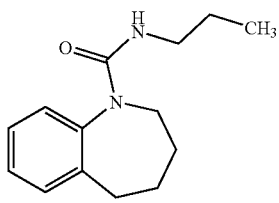

(D) The compounds represented by formula (D)

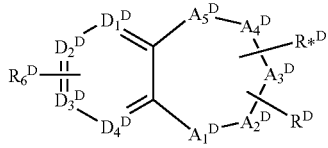
(D)

have been described as fibrinogen antagonists in WO93/00095 specification.

(E) The compounds represented by formula (E)

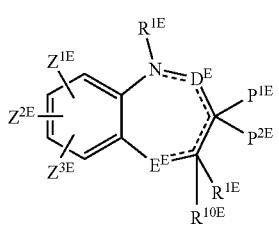
(E)

have been described as endothelin antagonists in WO95/04534 specification.

However, 1-carbamoyl-1-benzazepine compound is not concretely indicated in a patent publication in which the compounds represented by formula (D) and (E) have been described.

(F) In *J. Chem. Soc. Perkin Trans* 1 (1992), (24), 3401-6, (F-1) 7-acetyl-1-methylcarbamoyl-2,3,4,5-tetrahydro-1H-1-benzazepine (CAS No. 147265-78-9)

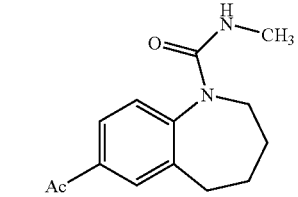
and (F-2) 1-methylcarbamoyl-2,3,4,5-tetrahydro-1H-1-benzazepine(CAS No. 147265-72-3)

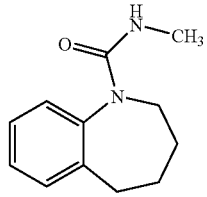

have been described.

(G) In *J. Med. Chem.* 1967, 10(5)944-5, (G-1) 1-carbamoyl-3-phenyl-2,3,4,5-tetrahydro-1H-1-benzazepine (CAS No. 16967-72-9)

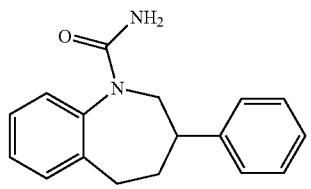

have been described.

However, so far, it has not been known at all that 1-carbamoyl-1-benzazepine compound has MBR competitive activity.

DISCLOSURE OF THE INVENTION

As a result that the present inventors assiduously examined to find the relation between MBR and stress, they found MBR antagonists comprising a compound represented by formula (I) to be useful for diseases attributable to stress and completed the present invention.

That is, the present invention relates to compounds represented by (1) the formula (I)

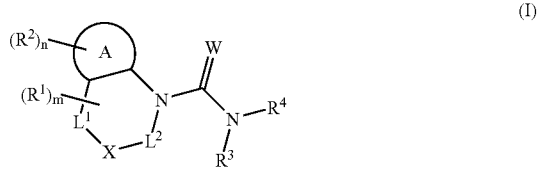
(I)

wherein, ring A represents a C5-8 monocyclic carbocyclic ring or a 5-8 membered monocyclic heterocyclic ring having 1-2 nitrogen atom(s), 1-2 oxygen atom(s) and/or a sulfur atom, X represents (1) —CH$_2$—, (2) —O—, (3) —S—, (4) —S(O)—, or (5) —SO$_2$—, L$^1$ and L$^2$ each independently represents a single bond, C1-4 alkylene, or C2-4 alkenylene and wherein the total carbon number of L$^1$ and L$^2$ is 3 or 4, respectively, R$^1$ and R$^2$ each independently represents,
(1) C1-8 alkyl, C2-8 alkenyl, or C2-8 alkynyl that may be substituted by 1-5 group(s) selected from ring B, OR$^5$, NR$^6$R$^7$, COR$^8$, OCOR$^8$, OCONR$^6$R$^7$, COOR$^8$, SR$^9$, SOR$^8$, SO$_2$R$^8$, SO$_2$NR$^6$R$^7$, a halogen atom, carboxyl, cyano, and nitro,
(2) ring B, (3) OR$^5$, (4) NR$^6$R$^7$, (5) COR$^8$, (6) OCOR$^8$, (7) OCONR$^6$R$^7$, (8) COOR$^8$, (9) CONR$^6$R$^7$, (10) SR$^9$, (11) SOR$^8$, (12) SO$_2$R$^8$, (13) SO$_2$NR$^6$R$^7$, (14) a halogen atom, (15) a carboxyl, (16) a cyano, (17) a nitro, (18) an oxo, or a

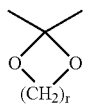

(19)

wherein ring B represents (i) a C3-10 monocyclic or a bicyclic carbocyclic ring or (ii) a 5-10 members' monocyclic or a bicyclic heterocyclic ring with 1-2 nitrogen atom(s), 1-2 oxygen atom(s) and/or a sulfur atom, ring B may be substituted by 1-5 group(s) wherein all symbols have the same meanings as the defined above selected from (i) C1-8 alkyl, C2-8 alkenyl, or C2-8 alkynyl that may be substituted by 1-5 groups selected from OR$^5$, NR$^6$R$^7$, COR$^8$, OCOR$^8$, OCONR$^6$R$^7$, COOR$^8$, CONR$^6$R$^7$, SR$^9$, SOR$^8$, SO$_2$R$^8$, SO$_2$NR$^6$R$^7$, halogen atom, carboxyl, cyano, and nitro, (ii) OR$^5$, (iii) NR$^6$R$^7$, (iv) COR$^8$, (v) OCOR$^8$, (vi) OCONR$^6$R$^7$, (vii) COOR$^8$, (viii) CONR$^6$R$^7$, (ix) SR$^9$, (x) SOR$^8$, (xi) SO$_2$R$^8$, (xii) SO$_2$NR$^6$R$^7$, (xiii) halogen atom, (xiv) carboxyl, (xv) cyano, (xvi) nitro, and (xvii) oxo, R$^5$ represents (i) a hydrogen atom, (ii) C1-8 alkyl, C2-8 alkenyl, or C2-8 alkynyl that may be substituted by 1-5 group(s) selected from OR$^{15}$, NR$^{16}$R$^{17}$, COR$^{18}$, OCOR$^{18}$, OCONR$^{16}$R$^{17}$, COOR$^{18}$, CONR$^{16}$R$^{17}$, SR$^{19}$, SOR$^8$, SO$_2$R$^8$, SO$_2$NR$^6$R$^7$, ring C, halogen atom(s), carboxyl, cyano, and nitro, (iii)-Si(R$^{10}$)$_3$, or (iv) ring C, R$^6$ and R$^7$ each independently represents (i) a hydrogen atom or (ii) —D$^1$-D$^2$ wherein D$^1$ represents (a) a single bond, (b)—C(O)—, (c)—C(O)O—, or (d)SO$_2$—, D represents (a) C1-8 alkyl, C2-8 alkenyl, or C2-8 alkynyl that may be substituted by ring C, or (b) ring C, ring C represents (a) a C3-10 monocyclic or bicyclic carbocyclic ring, or (b) a 5-10 members' monocyclic or bicyclic heterocyclic ring having 1-2 nitrogen atom(s), 1-2 oxygen atom(s), and/or a sulfur atom, ring C may be substituted by 1-5 group(s) selected from C1-8 alkyl, OR$^{15}$, NR$^{16}$ R$^{17}$, COR$^{18}$, OCOR$^{18}$, OCONR$^{16}$R$^{17}$, COOR$^{18}$, CONR$^{16}$R$^{17}$, SR$^{19}$, SOR$^{18}$, SO$_2$R$^{18}$, SO$_2$NR$^{16}$R$^{17}$, a halogen atom, carboxy, cyano, nitro and oxo, R$^8$ represents (i) C1-8 alkyl, C2-8 alkenyl or C2-8 alkynyl that may be substituted by ring C, or (ii) ring C, R$^9$ represents (i) a hydrogen atom, (ii) C1-8 alkyl, C2-8 alkenyl, or C2-8 alkynyl that may be substituted by 1-5 group(s) selected from OR$^{15}$, NR$^{16}$R$^{17}$, COR$^{18}$, OCOR$^{18}$, OCONR$^{16}$R$^{17}$, COOR$^{18}$, CONR$^{16}$R$^7$, SR$^{19}$, SOR$^{18}$, SO$_2$R$^{18}$, SO$_2$NR$^{16}$R$^{17}$, halogen atom, and ring C, or (iii) ring B, two or more R$^{10}$ each independently represents C1-8 alkyl or phenyl, R$^{15}$ and R$^{19}$ each independently represents C1-8 alkyl, C2-8 alkenyl, C2-8 alkynyl or C2-8 acyl, R$^{16}$ and R$^{17}$ each independently represents (i) C1-8 alkyl, C2-8 alkenyl, or C2-8 alkynyl, or (ii) phenyl that may be substituted by C1-8 alkyl, C2-8 alkenyl, C2-8 alkynyl, halogen atom, C1-8 alkoxy, C2-8 alkenyloxy, or C2-8 alkynyloxy, R$^{18}$ represents C1-8 alkyl, C2-8 alkenyl, or C2-8 alkynyl, r represents an integer of 2-4, m and n each independently represents 0 or an integer of 1-4, R$^3$ represents
(i) a hydrogen atom, (ii) ring B, or
(iii) C1-8 alkyl, C2-8 alkenyl, or C2-8 alkynyl that may be substituted by 1-5 group(s) selected from ring B, OR$^5$, NR$^6$R$^7$, COR$^8$, OCOR$^8$, OCONR$^6$R$^7$, COOR$^8$, CONR$^6$R$^7$, SR$^9$, SOR$^8$, SO$_2$R$^8$, SO$_2$NR$^6$R$^7$, halogen atom, cyano, and nitro wherein all symbols represent the same meanings as defined above, R$^4$ represents a hydrogen atom, C1-8 alkyl, C2-8 alkenyl, or C2-8 alkynyl or R$^3$ and R$^4$, taken together with the nitrogen atom bound thereto, may form a 5-10 membered monocyclic or a bicyclic heterocyclic ring that contains a nitrogen atom and may contain 1-3 nitrogen atom(s), an oxygen atom, and/or a sulfur atom wherein the heterocyclic ring may be substituted by 1-5 group(s) selected from C1-8 alkyl, OR$^{15}$, NR$^{16}$R$^{17}$, COR$^{18}$, OCOR$^{18}$, OCONR$^{16}$R$^{17}$, COOR$^{18}$, CONR$^{16}$R$^{17}$, SR$^{19}$, SOR$^{18}$, SO$_2$R$^{18}$, SO$_2$NR$^{16}$R$^{17}$, halogen atom carboxyl, cyano, nitro and oxo; except for (1) 1-(N-2-dimethylaminoethyl-N-methylcarbamoyl)-4-phenyl-2,3,4,5-tetrahydro-1H-1-benzazepine,
(2) 1-cyclohexylcarbamoyl-7-methoxy-2,3,4,5-tetrahydro-1H-1-benzazepine,
(3) 7-methoxy-1-phenylcarbamoyl-2,3,4,5-tetrahydro-1H-1-benzazepine,
(4) 1-butylcarbamoyl-7-methoxy-2,3,4,5-tetrahydro-1H-1-benzazepine,
(5) 1-propylcarbamoyl-2,3,4,5-tetrahydro-1H-1-benzazepine,
(6) 7-acetyl-1-methylcarbamoyl-2,3,4,5-tetrahydro-1H-1-benzazepine,
(7) 1-methylcarbamoyl-2,3,4,5-tetrahydro-1H-1-benzazepine,
(8) 1-carbamoyl-3-phenyl-2,3,4,5-tetrahydro-1H-1-benzazepine, and
(9) N-[2-(dimethylamino)ethyl]-3,4-dihydro-N-methyl-2-phenyl-1,5-benzoxazepine-5(2H)-carboxamide, or a pharmaceutically acceptable salt thereof,
(2) a MBR antagonist comprising the compound represented by formula (I) or a pharmaceutically acceptable salt as active ingredient thereof,
(3) a manufacturing method of the compound represented by formula (I) or a pharmaceutically acceptable salt thereof, and
(4) a medicine for prevention and/or treatment for disease induced or exacerbated/reburnt according to stress.

In formula (I), C1-8 alkyl means methyl, ethyl, propyl, butyl, pentyl, hexyl, heptyl, octyl and those isomers.

In formula (I), C2-8 alkenyl means vinyl, propenyl, butenyl, pentenyl, hexenyl, heptenyl, octenyl and those isomers.

In formula (I), C2-8 alkynyl represents ethynyl, propynyl, butynyl, pentinyl, hexynyl, heptynyl, octynyl and those isomers.

In formula (I), halogen atom represents fluorine, chlorine, bromine and iodine.

In formula (I), C1-4 alkylene represents methylene, ethylene, propylene and butylene.

In formula (I), C2-4 alkenylene represents vinylene, propenylene and butenylene.

In formula (I), C1-8 alkoxy means methoxy, ethoxy, propoxy, butoxy, pentyloxy, hexyloxy, heptyloxy, octyloxy and those isomers.

In formula (I), C2-8 alkenyloxy means vinyloxy, propenyloxy, butenyloxy, pentenyloxy, hexenyloxy, heptenyloxy, octenyloxy and those isomers.

In formula (I), C2-8 alkynyloxy represents ethynyloxy, propynyloxy, butynyloxy, pentinyloxy, hexynyloxy, heptynyloxy, octynyloxy and those isomers.

In formula (I), C5-8 monocyclic carbocyclic ring that ring A represents represents C5-8 monocyclic aromatic carbon ring and the carbocyclic ring saturated in part or all.

The C5-8 monocyclic aromatic carbon ring and the carbocyclic ring saturated in part or all includes, for example, benzene, cyclopentane, cyclohexane, cycloheptane, cyclooctane, cyclopentene, cyclohexene, cyclooctene, cyclopentadiene, cyclohexadiene, cycloheptadiene, cyclooctadiene, cycloheptatriene and cyclooctatriene, etc.

In formula (I), a 5-8 members' monocyclic heterocyclic ring including 1-2 nitrogen atom(s), 1-2 oxygen atom(s), and/or a sulfur atom, which ring A represents, represents a 5-8 members' monocyclic heterocyclic ring aryl and the carbocyclic ring saturated in part or all, including 1-2 nitrogen atom(s), 1-2 oxygen atom(s), and/or a sulfur atom.

The 5-8 members' monocyclic heterocycle aryl and the carbocyclic ring saturated in part or all, including 1-2 nitrogen atom(s), 1-2 oxygen atom(s), and/or a sulfur atom includes, for example, pyrrole, imidazole, pyrazole, pyridine, pyrazine, pyrimidine, pyridazine, azepine, diazepine, azocine, diazocine, furan, pyran, oxepin, oxazepine, thiophene, thiaine (thiopyran), thiepin, oxazole, isoxazole, thiazole, isothiazole, oxazine, oxadiazine, oxazepine, thiadiazole, thiazine, thiadiazine and thiazepine, etc.

The above-described the C5-8 monocyclic aromatic carbon ring and the carbocyclic ring saturated in part or all includes, for example, pyrroline, pyrrolidine, imidazoline, imidazolidine, dihydropyridine, dihydropyrazine, dihydropyrimidine, dihydropyridazin, piperidine, tetrahydropyridine, piperazine, tetrahydropyrimidine, tetrahydropyridazine, dihydrofuran, tetrahydrofuran, dihydropyran, tetrahydropyran, dihydrothiophene, tetrahydrothiophene, dihydrothiaine (dihydrothiopyran), tetrahydrothiaine (tetrahydrothiopyran), dihydrooxazole, tetrahydrooxazole, dihydroisoxazole, tetrahydroisoxazole, dihydrothiazole, tetrahydrothiazole, dihydroisothiazole, tetrahydroisothiazole, morpholine, thiomorpholine and dioxane, etc.

In formula (I), a C3-10 monocyclic and a bicyclic carbocyclic, which ring C and ring B represents, represents a C3-10 monocyclic or bicyclic aromatic carbon ring and the saturated one in all or part.

As the C3-10 monocyclic or bicyclic aromatic carbon ring and the saturated one in all or part, for example, benzene, cyclopropane, cyclobutane, cyclopentane, cyclohexane, cycloheptane, cyclooctane, cyclononane, cyclodecane, cyclopentene, cyclohexene, cycloheptene, cyclooctene, cyclononene, cyclodecene, cyclopentadiene, cyclohexadiene, cycloheptadiene, cyclooctadiene, cyclononadiene, cyclodecadiene, cycloheptatriene, cyclooctatriene, cyclononatriene, cyclodecatriene, pentalene, indan, indene, naphthalene, azulene, perhydropentalene, perhydroindene, dihydronaphthalene, tetrahydronaphthalene, perhydronaphthalene and perhydroazulene, etc. are included.

As 5-10 members' monocyclic or bicyclic heterocycle which contains a nitrogen atom formed with a nitrogen atom to which $R^3$ and $R^4$ bind, and may contain 1-3 nitrogen atom(s), an oxygen atom, and/or a sulfur atom, a 5-10 members' monocyclic or a bicyclic heterocycle aryl which contains a nitrogen atom, and may contain 1-3 nitrogen atom(s), an oxygen atom, and/or a sulfur atom and the saturated one in all or part are included.

As the 5-10 members' monocyclic or bicyclic heterocycle aryl which contains a nitrogen atom, and may contain 1-3 nitrogen atom(s), an oxygen atom, and/or a sulfur atom, for example, imidazole, triazole, tetrazole, pyrrole, pyrazol, indole, isoindole, indazole, purine, pyrroline, pyrrolidine, imidazoline, imidazolidine, pyrazoline, pyrazolidine, dihydropyridine, dihydropyrazine, dihydropyrimidine, dihydropyridazine, piperidine, tetrahydropyridine, piperazine, tetrahydropyrimidine, tetrahydropyridazine, dihydrooxazole, tetrahydrooxazole, dihydroisoxazole, tetrahydroisoxazole, dihydrothiazole, tetrahydrothiazole, dihydroisothiazole, tetrahydroisothiazole, morpholine and thiomorpholine, etc. are included.

Though both groups in the compound represented by formula (I) in the present invention are preferable, especially the compounds with the following groups are preferable.

As ring A, both a C5-8 carbocyclic ring and a 5-8 members' heterocyclic ring are preferable, especially a C5-6 carbocyclic ring and a 5-6 members' heterocyclic ring are preferable. As the C5-6 carbocyclic ring, benzene, cyclohexadiene, cyclohexane, cyclopentene, cyclohexane, and cyclopentane are preferable, and as 5-6 members' heterocycles, pyridine, thiophene, furan, pyrazine, oxazole, thiazole, isoxazole and isothiazole are preferable.

As $R^1$, both are preferable, C1-8 alkyl that may be substituted, $OR^5$, $NR^6R^7$, $COR^8$, $CONR^6R^7$, $COOR^8$, halogen atom, cyano, nitro, oxo,

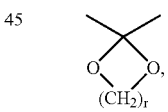

and ring B that may be substituted are more preferable. Especially, C1-8 alky that may be substituted, $OR^5$, $NR^6R^7$, $COR^8$, $CONR^6R^7$, $COOR^8$, a fluorine atom, a chlorine atom, cyano, oxo,

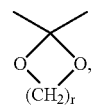

and ring B that may be substituted are preferable.

As $R^2$, both are preferable, C1-8 alkyl that may be substituted, $OR^5$, $NR^6R^7$, $COR^8$, $CONR^6R^7$, $COOR^8$, halogen atom, cyano, nitro, and ring B that may be substituted are more preferable. Especially, C1-8 alkyl that may be substituted, $OR^5$, $NR^6R^7$, $COR^8$, $CONR^6R^7$, $COOR^8$, a fluorine atom, a chlorine atom, a bromine atom, cyano, nitro, and ring B that may be substituted are preferable.

As ring B in $R^1$ and $R^2$, both are preferable, a C5-8 carbocyclic ring and a 5-8 members' heterocyclic ring are especially preferable. Concretely, phenyl, cyclohexane, cyclopentane, cycloheptane, thiophene, furan, pyrrole, pyrrolidine, piperidine, perhydroazepine, morpholine, thiomorpholine, oxazole, imidazole, thiazole, pyrazole, pyridine, pyrimidine and pyrazine are preferable.

As $R^3$, both are preferable, (i) a hydrogen atom, (ii) ring B that may be substituted, and (iii) C1-8 alkyl groups or a C2-8 alkenyl that may be substituted are more preferable.

As a substituent of C1-8 alkyl and C2-8 alkenyl in $R^3$, ring B that may be substituted, $OR^5$, $NR^6R^7$, $COR^8$, $CONR^6R^7$, a halogen atom, cyano, nitro, and an oxo are preferable.

As substituents of ring B included in $R^3$, C1-8 alkyl that may be substituted, $OR^5$, $NR^6R^7$, $COOR^8$, $SR^9$, a halogen atom, cyano, nitro, oxo, and carboxyl are preferable.

As $R^4$, both are preferable, a hydrogen atom or C1-8 alkyl is more preferable, and a hydrogen atom or C1-4 alkyl is further preferable.

In addition, a 5-6 members' heterocyclic ring formed with a nitrogen atom to which $R^3$ and $R^4$ bind are preferable. As the ring, piperidine, piperazine, and imidazole are especially preferable.

Although as W, both an oxygen atom and a sulfur atom are preferable, an oxygen atom is more preferable.

As ring B included in $R^3$, both are preferable, especially, benzene, cyclopropane, cyclobutane, cyclopentane, cyclohexane, cycloheptane, cyclooctane, cyclopentene, cyclohexane, cycloheptene, cyclooctene, cyclohexadiene, cycloheptadiene, cyclooxadiene, piperidine, piperazine, pyridine, dihydropyridine, indole, dihydroindole, pyrrolidine, thiazole, benzothiazole and benzodioxole are preferable.

It is preferable that the total carbon number of $L^1$ and $L^2$ is both 3 or 4, especially 3.

As X, both are preferable, especially —$CH_2$— or —O— is preferable. In ring represented by

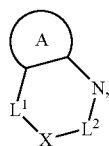

the preferable ones are, for example, rings represented by

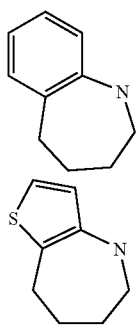 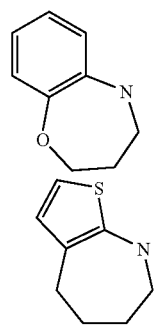 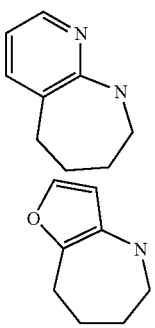

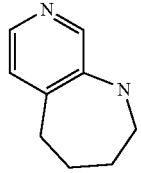 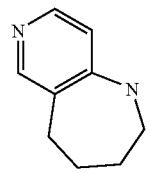 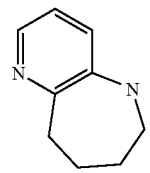

-continued

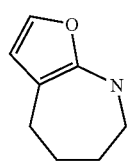 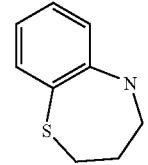 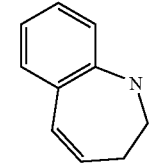

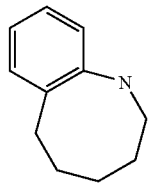 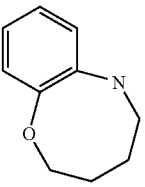 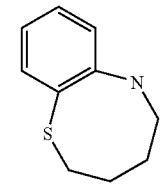

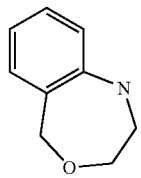 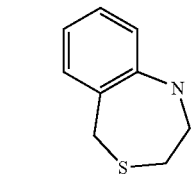

As a preferable present compound, a compound represented by the following formula (I-a)

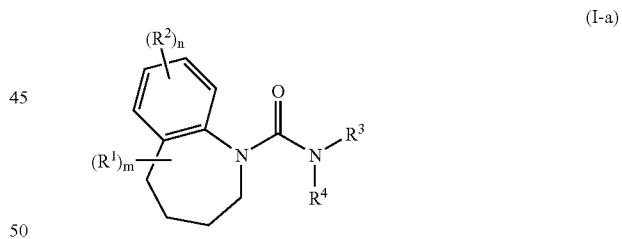

(I-a)

wherein all symbols have the same meanings as defined above, a compound represented by the following formula (I-b)

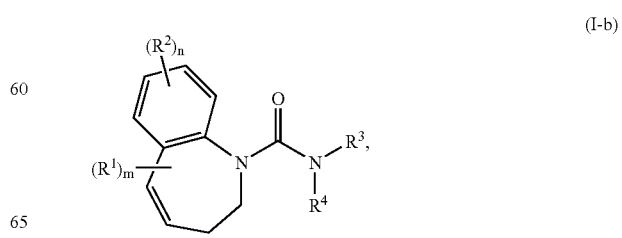

(I-b)

wherein all symbols have the same meanings as defined above, a compound represented by the following formula (I-c)

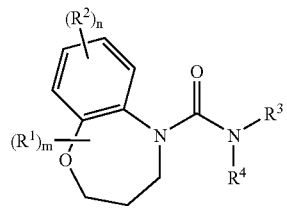
(I-c)

wherein all symbols have the same meanings as defined above, a compound represented by the following formula (I-d)

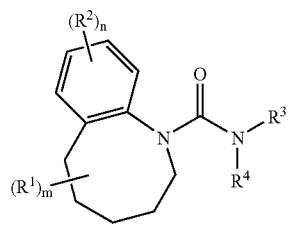
(I-d)

wherein all symbols have the same meanings as defined above, a compound represented by the following formula (I-e)

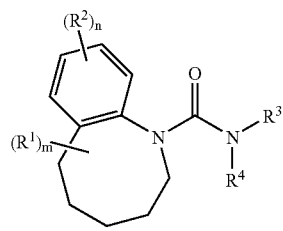
(I-e)

wherein all symbols have the same meanings as defined above, a compound represented by the following formula (I-f)

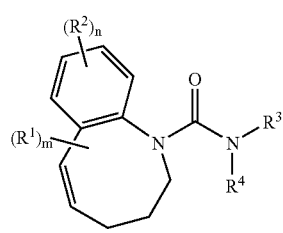
(I-f)

wherein all symbols have the same meanings as defined above, a compound represented by the following formula (I-g)

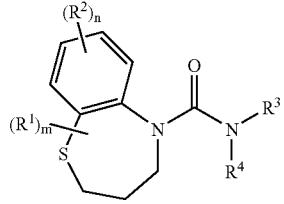
(I-g)

wherein all symbols have the same meanings as defined above, a compound represented by the following formula (I-h)

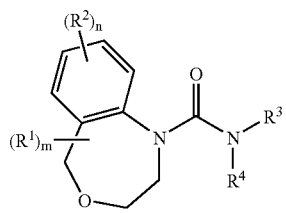
(I-h)

wherein all symbols have the same meanings as defined above, a compound represented by the following formula (I-j)

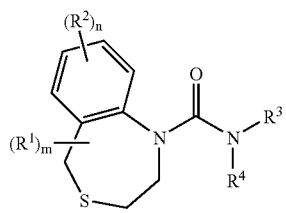
(I-j)

wherein all symbols have the same meanings as defined above, a compound represented by the following formula (I-k)

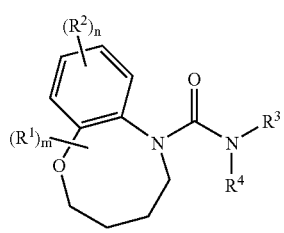
(I-k)

wherein all symbols have the same meanings as defined above, and a compound represented by the following formula (I-m)

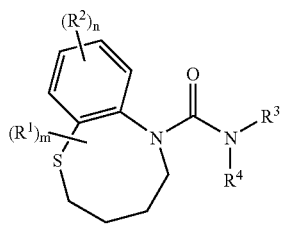

(I-m)

wherein all symbols have the same meanings as defined above are contained.

Concretely, compounds represented by the example described later and the following tables 1-5 are preferable. Though the following tables 1-5 illustrate compounds represented by formula (I-a), as to compounds represented by formula (I-b) to (I-m), the compounds with a similar group are also preferable. The number applied before each groups in the following tables represents the site of substitution. For example, 3-$CH_3$ represents methyl substituted at the third position.

TABLE 1

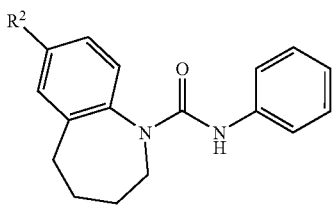

(I-a-1)

| Number | $R^2$ |
|---|---|
| 1 | H |
| 2 | $CH_3$ |
| 3 | OH |
| 4 | $OCH_3$ |
| 5 | $NH_2$ |
| 6 | $NHCH_3$ |
| 7 | $N(CH_3)_2$ |
| 8 | $NO_2$ |
| 9 | F |
| 10 | Cl |

TABLE 2

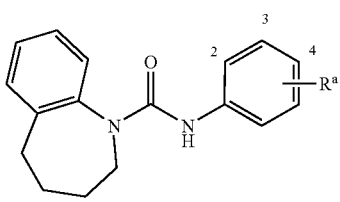

(I-a-2)

| Number | $R^a$ |
|---|---|
| 1 | H |
| 2 | 2-$CH_3$ |
| 3 | 2-$OCH_3$ |
| 4 | 2-$NO_2$ |
| 5 | 2-F |
| 6 | 2-Cl |

TABLE 2-continued

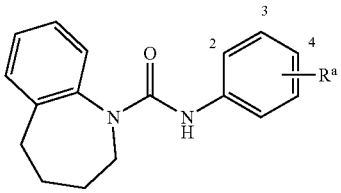

(I-a-2)

| Number | $R^a$ |
|---|---|
| 7 | 3-$CH_3$ |
| 8 | 3-$OCH_3$ |
| 9 | 3-$NO_2$ |
| 10 | 3-F |
| 11 | 3-Cl |
| 12 | 4-$CH_3$ |
| 13 | 4-$OCH_3$ |
| 14 | 4-$NO_2$ |
| 15 | 4-F |
| 16 | 4-Cl |

TABLE 3

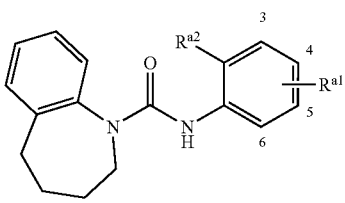

(I-a-3)

| Number | $R^{a1}$ | $R^{a2}$ |
|---|---|---|
| 1-1 | H | OH |
| 1-2 | 3-$CH_3$ | OH |
| 1-3 | 3-$OCH_3$ | OH |
| 1-4 | 3-$NO_2$ | OH |
| 1-5 | 3-F | OH |
| 1-6 | 3-Cl | OH |
| 1-7 | 4-$CH_3$ | OH |
| 1-8 | 4-$OCH_3$ | OH |
| 1-9 | 4-$NO_2$ | OH |
| 1-10 | 4-F | OH |
| 1-11 | 4-Cl | OH |
| 1-12 | 5-$CH_3$ | OH |
| 1-13 | 5-$OCH_3$ | OH |
| 1-14 | 5-$NO_2$ | OH |
| 1-15 | 5-F | OH |
| 1-16 | 5-Cl | OH |
| 1-17 | 6-$CH_3$ | OH |
| 1-18 | 6-$OCH_3$ | OH |
| 1-19 | 6-$NO_2$ | OH |
| 1-20 | 6-F | OH |
| 1-21 | 6-Cl | OH |
| 2-1 | H | $NH_2$ |
| 2-2 | 3-$CH_3$ | $NH_2$ |
| 2-3 | 3-$OCH_3$ | $NH_2$ |
| 2-4 | 3-$NO_2$ | $NH_2$ |
| 2-5 | 3-F | $NH_2$ |
| 2-6 | 3-Cl | $NH_2$ |
| 2-7 | 4-$CH_3$ | $NH_2$ |
| 2-8 | 4-$OCH_3$ | $NH_2$ |
| 2-9 | 4-$NO_2$ | $NH_2$ |
| 2-10 | 4-F | $NH_2$ |
| 2-11 | 4-Cl | $NH_2$ |
| 2-12 | 5-$CH_3$ | $NH_2$ |
| 2-13 | 5-$OCH_3$ | $NH_2$ |
| 2-14 | 5-$NO_2$ | $NH_2$ |
| 2-15 | 5-F | $NH_2$ |
| 2-16 | 5-Cl | $NH_2$ |

TABLE 3-continued (I-a-3)

| Number | R$^{a1}$ | R$^{a2}$ |
|---|---|---|
| 2-17 | 6-CH$_3$ | NH$_2$ |
| 2-18 | 6-OCH$_3$ | NH$_2$ |
| 2-19 | 6-NO$_2$ | NH$_2$ |
| 2-20 | 6-F | NH$_2$ |
| 2-21 | 6-Cl | NH$_2$ |
| 3-1 | H | NHCH$_3$ |
| 3-2 | 3-CH$_3$ | NHCH$_3$ |
| 3-3 | 3-OCH$_3$ | NHCH$_3$ |
| 3-4 | 3-NO$_2$ | NHCH$_3$ |
| 3-5 | 3-F | NHCH$_3$ |
| 3-6 | 3-Cl | NHCH$_3$ |
| 3-7 | 4-CH$_3$ | NHCH$_3$ |
| 3-8 | 4-OCH$_3$ | NHCH$_3$ |
| 3-9 | 4-NO$_2$ | NHCH$_3$ |
| 3-10 | 4-F | NHCH$_3$ |
| 3-11 | 4-Cl | NHCH$_3$ |
| 3-12 | 5-CH$_3$ | NHCH$_3$ |
| 3-13 | 5-OCH$_3$ | NHCH$_3$ |
| 3-14 | 5-NO$_2$ | NHCH$_3$ |
| 3-15 | 5-F | NHCH$_3$ |
| 3-16 | 5-Cl | NHCH$_3$ |
| 3-17 | 6-CH$_3$ | NHCH$_3$ |
| 3-18 | 6-OCH$_3$ | NHCH$_3$ |
| 3-19 | 6-NO$_2$ | NHCH$_3$ |
| 3-20 | 6-F | NHCH$_3$ |
| 3-21 | 6-Cl | NHCH$_3$ |

TABLE 4

(I-a-4)

| Number | R$^{a1}$ | R$^{a2}$ |
|---|---|---|
| 1-1 | H | OH |
| 1-2 | 2-CH$_3$ | OH |
| 1-3 | 2-OCH$_3$ | OH |
| 1-4 | 2-NO$_2$ | OH |
| 1-5 | 2-F | OH |
| 1-6 | 2-Cl | OH |
| 1-7 | 4-CH$_3$ | OH |
| 1-8 | 4-OCH$_3$ | OH |
| 1-9 | 4-NO$_2$ | OH |
| 1-10 | 4-F | OH |
| 1-11 | 4-Cl | OH |
| 1-12 | 5-CH$_3$ | OH |
| 1-13 | 5-OCH$_3$ | OH |
| 1-14 | 5-NO$_2$ | OH |
| 1-15 | 5-F | OH |
| 1-16 | 5-Cl | OH |
| 1-17 | 6-CH$_3$ | OH |
| 1-18 | 6-OCH$_3$ | OH |
| 1-19 | 6-NO$_2$ | OH |
| 1-20 | 6-F | OH |

TABLE 4-continued (I-a-4)

| Number | R$^{a1}$ | R$^{a2}$ |
|---|---|---|
| 1-21 | 6-Cl | OH |
| 2-1 | H | NH$_2$ |
| 2-2 | 2-CH$_3$ | NH$_2$ |
| 2-3 | 2-OCH$_3$ | NH$_2$ |
| 2-4 | 2-NO$_2$ | NH$_2$ |
| 2-5 | 2-F | NH$_2$ |
| 2-6 | 2-Cl | NH$_2$ |
| 2-7 | 4-CH$_3$ | NH$_2$ |
| 2-8 | 4-OCH$_3$ | NH$_2$ |
| 2-9 | 4-NO$_2$ | NH$_2$ |
| 2-10 | 4-F | NH$_2$ |
| 2-11 | 4-Cl | NH$_2$ |
| 2-12 | 5-CH$_3$ | NH$_2$ |
| 2-13 | 5-OCH$_3$ | NH$_2$ |
| 2-14 | 5-NO$_2$ | NH$_2$ |
| 2-15 | 5-F | NH$_2$ |
| 2-16 | 5-Cl | NH$_2$ |
| 2-17 | 6-CH$_3$ | NH$_2$ |
| 2-18 | 6-OCH$_3$ | NH$_2$ |
| 2-19 | 6-NO$_2$ | NH$_2$ |
| 2-20 | 6-F | NH$_2$ |
| 2-21 | 6-Cl | NH$_2$ |
| 3-1 | H | NHCH$_3$ |
| 3-2 | 2-CH$_3$ | NHCH$_3$ |
| 3-3 | 2-OCH$_3$ | NHCH$_3$ |
| 3-4 | 2-NO$_2$ | NHCH$_3$ |
| 3-5 | 2-F | NHCH$_3$ |
| 3-6 | 2-Cl | NHCH$_3$ |
| 3-7 | 4-CH$_3$ | NHCH$_3$ |
| 3-8 | 4-OCH$_3$ | NHCH$_3$ |
| 3-9 | 4-NO$_2$ | NHCH$_3$ |
| 3-10 | 4-F | NHCH$_3$ |
| 3-11 | 4-Cl | NHCH$_3$ |
| 3-12 | 5-CH$_3$ | NHCH$_3$ |
| 3-13 | 5-OCH$_3$ | NHCH$_3$ |
| 3-14 | 5-NO$_2$ | NHCH$_3$ |
| 3-15 | 5-F | NHCH$_3$ |
| 3-16 | 5-Cl | NHCH$_3$ |
| 3-17 | 6-CH$_3$ | NHCH$_3$ |
| 3-18 | 6-OCH$_3$ | NHCH$_3$ |
| 3-19 | 6-NO$_2$ | NHCH$_3$ |
| 3-20 | 6-F | NHCH$_3$ |
| 3-21 | 6-Cl | NHCH$_3$ |

TABLE 5

(I-a-5)

| Number | R$^{a1}$ | R$^{a2}$ |
|---|---|---|
| 1-1 | H | OH |
| 1-2 | 2-CH$_3$ | OH |
| 1-3 | 2-OCH$_3$ | OH |

TABLE 5-continued (I-a-5)

| Number | $R^{a1}$ | $R^{a2}$ |
|---|---|---|
| 1-4 | 2-NO$_2$ | OH |
| 1-5 | 2-F | OH |
| 1-6 | 2-Cl | OH |
| 1-7 | 3-CH$_3$ | OH |
| 1-8 | 3-OCH$_3$ | OH |
| 1-9 | 3-NO$_2$ | OH |
| 1-10 | 3-F | OH |
| 1-11 | 3-Cl | OH |
| 2-1 | H | NH$_2$ |
| 2-2 | 2-CH$_3$ | NH$_2$ |
| 2-3 | 2-OCH$_3$ | NH$_2$ |
| 2-4 | 2-NO$_2$ | NH$_2$ |
| 2-5 | 2-F | NH$_2$ |
| 2-6 | 2-Cl | NH$_2$ |
| 2-7 | 3-CH$_3$ | NH$_2$ |
| 2-8 | 3-OCH$_3$ | NH$_2$ |
| 2-9 | 3-NO$_2$ | NH$_2$ |
| 2-10 | 3-F | NH$_2$ |
| 2-11 | 3-Cl | NH$_2$ |
| 3-1 | H | NHCH$_3$ |
| 3-2 | 2-CH$_3$ | NHCH$_3$ |
| 3-3 | 2-OCH$_3$ | NHCH$_3$ |
| 3-4 | 2-NO$_2$ | NHCH$_3$ |
| 3-5 | 2-F | NHCH$_3$ |
| 3-6 | 2-Cl | NHCH$_3$ |
| 3-7 | 3-CH$_3$ | NHCH$_3$ |
| 3-8 | 3-OCH$_3$ | NHCH$_3$ |
| 3-9 | 3-NO$_2$ | NHCH$_3$ |
| 3-10 | 3-F | NHCH$_3$ |
| 3-11 | 3-Cl | NHCH$_3$ |

TABLE 6

(I-a-6)

| Number | $R^a$ |
|---|---|
| 1 | H |
| 2 | 2-CH$_3$ |
| 3 | 2-OCH$_3$ |
| 4 | 2-NO$_2$ |
| 5 | 2-F |
| 6 | 2-Cl |
| 7 | 3-CH$_3$ |
| 8 | 3-OCH$_3$ |
| 9 | 3-NO$_2$ |
| 10 | 3-F |
| 11 | 3-Cl |
| 12 | 4-CH$_3$ |
| 13 | 4-OCH$_3$ |
| 14 | 4-NO$_2$ |
| 15 | 4-F |
| 16 | 4-Cl |
| 17 | 2-NH$_2$ |

TABLE 6-continued (I-a-6)

| Number | $R^a$ |
|---|---|
| 18 | 2-CN |
| 19 | 2-NHCH$_3$ |
| 20 | 2-COOH |
| 21 | 2-OH |
| 22 | 3-NH$_2$ |
| 23 | 3-CN |
| 24 | 3-NHCH$_3$ |
| 25 | 3-COOH |
| 26 | 3-OH |
| 27 | 4-NH$_2$ |
| 28 | 4-CN |
| 29 | 4-NHCH$_3$ |
| 30 | 4-COOH |
| 31 | 4-OH |
| 32 | 4-COOCH$_3$ |

TABLE 7

(I-a-7)

| Number | $R^a$ |
|---|---|
| 1 | H |
| 2 | CH$_3$ |
| 3 | CH$_2$CH$_3$ |
| 4 | CH(CH$_3$)$_2$ |
| 5 | Ph |
| 6 | CH$_2$Ph |

TABLE 8

(I-a-8)

| Number | $R^a$ |
|---|---|
| 1 | H |
| 2 | 2-CH$_3$ |
| 3 | 2-OCH$_3$ |
| 4 | 2-NO$_2$ |
| 5 | 2-F |
| 6 | 2-Cl |
| 7 | 3-CH$_3$ |
| 8 | 3-OCH$_3$ |

TABLE 8-continued

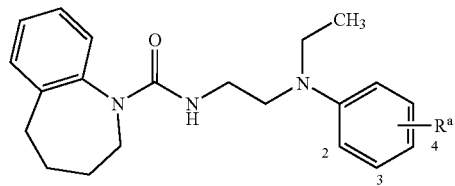

(I-a-8)

| Number | R$^a$ |
|---|---|
| 9 | 3-NO$_2$ |
| 10 | 3-F |
| 11 | 3-Cl |
| 12 | 4-CH$_3$ |
| 13 | 4-OCH$_3$ |
| 14 | 4-NO$_2$ |
| 15 | 4-F |
| 16 | 4-Cl |
| 17 | 2-NH$_2$ |
| 18 | 2-CN |
| 19 | 2-NHCH$_3$ |
| 20 | 2-COOH |
| 21 | 2-OH |
| 22 | 3-NH$_2$ |
| 23 | 3-CN |
| 24 | 3-NHCH$_3$ |
| 25 | 3-COOH |
| 26 | 3-OH |
| 27 | 4-NH$_2$ |
| 28 | 4-CN |
| 29 | 4-NHCH$_3$ |
| 30 | 4-COOH |
| 31 | 4-OH |
| 32 | 4-COOCH$_3$ |

TABLE 9

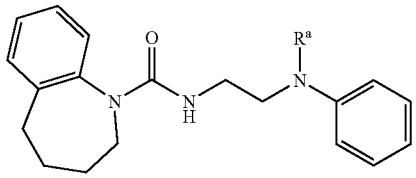

(I-a-9)

| Number | R$^a$ |
|---|---|
| 1 | H |
| 2 | CH$_3$ |
| 3 | CH$_2$CH$_3$ |
| 4 | CH(CH$_3$)$_2$ |
| 5 | Ph |
| 6 | CH$_2$Ph |

TABLE 10

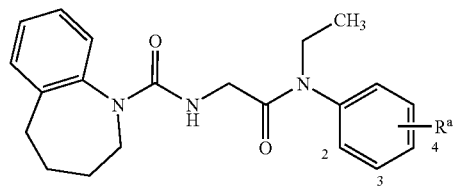

(I-a-10)

| Number | R$^a$ |
|---|---|
| 1 | H |
| 2 | 2-CH$_3$ |
| 3 | 2-OCH$_3$ |
| 4 | 2-NO$_2$ |
| 5 | 2-F |
| 6 | 2-Cl |
| 7 | 3-CH$_3$ |
| 8 | 3-OCH$_3$ |
| 9 | 3-NO$_2$ |
| 10 | 3-F |
| 11 | 3-Cl |
| 12 | 4-CH$_3$ |
| 13 | 4-OCH$_3$ |
| 14 | 4-NO$_2$ |
| 15 | 4-F |
| 16 | 4-Cl |
| 17 | 2-NH$_2$ |
| 18 | 2-CN |
| 19 | 2-NHCH$_3$ |
| 20 | 2-COOH |
| 21 | 2-OH |
| 22 | 3-NH$_2$ |
| 23 | 3-CN |
| 24 | 3-NHCH$_3$ |
| 25 | 3-COOH |
| 26 | 3-OH |
| 27 | 4-NH$_2$ |
| 28 | 4-CN |
| 29 | 4-NHCH$_3$ |
| 30 | 4-COOH |
| 31 | 4-OH |
| 32 | 4-COOCH$_3$ |

TABLE 11

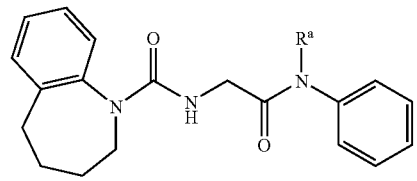

(I-a-11)

| Number | R$^a$ |
|---|---|
| 1 | H |
| 2 | CH$_3$ |
| 3 | CH$_2$CH$_3$ |
| 4 | CH(CH$_3$)$_2$ |
| 5 | Ph |
| 6 | CH$_2$Ph |

TABLE 12

(I-a-12)

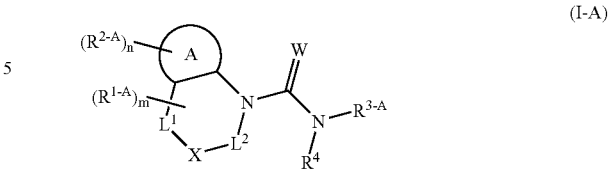

| Number | R$^a$ | Number | R$^a$ |
|---|---|---|---|
| 1 | H | 17 | 2-NH$_2$ |
| 2 | 2-CH$_3$ | 18 | 2-CN |
| 3 | 2-OCH$_3$ | 19 | 2-NHCH$_3$ |
| 4 | 2-NO$_2$ | 20 | 2-COOH |
| 5 | 2-F | 21 | 2-OH |
| 6 | 2-Cl | 22 | 3-NH$_2$ |
| 7 | 3-CH$_3$ | 23 | 3-CN |
| 8 | 3-OCH$_3$ | 24 | 3-NHCH$_3$ |
| 9 | 3-NO$_2$ | 25 | 3-COOH |
| 10 | 3-F | 26 | 3-OH |
| 11 | 3-Cl | 27 | 4-NH$_2$ |
| 12 | 4-CH$_3$ | 28 | 4-CN |
| 13 | 4-OCH$_3$ | 29 | 4-NHCH$_3$ |
| 14 | 4-NO$_2$ | 30 | 4-COOH |
| 15 | 4-F | 31 | 4-OH |
| 16 | 4-Cl | 32 | 4-COOCH$_3$ |

TABLE 13

(I-a-13)

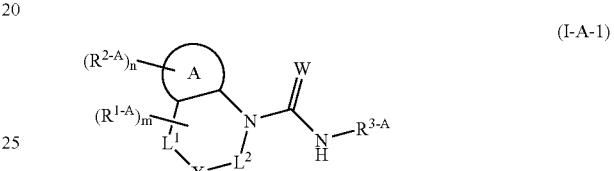

| Number | R$^a$ | Number | R$^a$ |
|---|---|---|---|
| 1 | H | 17 | 2-NH$_2$ |
| 2 | 2-CH$_3$ | 18 | 2-CN |
| 3 | 2-OCH$_3$ | 19 | 2-NHCH$_3$ |
| 4 | 2-NO$_2$ | 20 | 2-COOH |
| 5 | 2-F | 21 | 2-OH |
| 6 | 2-Cl | 22 | 3-NH$_2$ |
| 7 | 3-CH$_3$ | 23 | 3-CN |
| 8 | 3-OCH$_3$ | 24 | 3-NHCH$_3$ |
| 9 | 3-NO$_2$ | 25 | 3-COOH |
| 10 | 3-F | 26 | 3-OH |
| 11 | 3-Cl | 27 | 4-NH$_2$ |
| 12 | 4-CH$_3$ | 28 | 4-CN |
| 13 | 4-OCH$_3$ | 29 | 4-NHCH$_3$ |
| 14 | 4-NO$_2$ | 30 | 4-COOH |
| 15 | 4-F | 31 | 4-OH |
| 16 | 4-Cl | 32 | 4-COOCH$_3$ |

Manufacturing Method of the Present Invention Compound

The present compound represented by formula (I) can be manufactured according to the following methods.

[1] In the compounds of the present invention represented by formula (I), the compounds that R$^1$, R$^2$, and R$^3$ neither contain free amino, hydroxyl, carboxyl or mercapto, i.e., the compounds represented by formula (I-A)

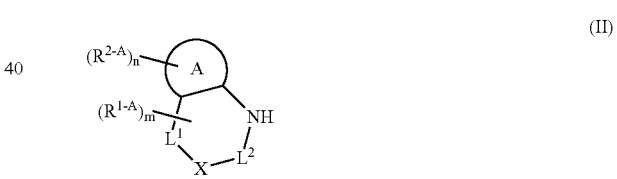

(I-A)

wherein R$^{1-A}$, R$^{2-A}$, and R$^{3-A}$ represent the same meanings as R$^1$, R$^2$, and R$^3$, respectively, neither contain free amino, hydroxyl, carboxyl, or mercapto. Other symbols have the same meanings as defined above can be manufactured according to the following methods.

(1) In the compounds represented by formula (I-A), a compound which R$^4$ is a hydrogen atom, i.e., the compound represented by formula (I-A-1)

(I-A-1)

wherein all symbols have the same meaning as defined above can be manufactured by (thio) urea reaction.

The (thio) urea reaction is executed by (A) the reaction by using of (thio) isocyanate or (B) the reaction by using of (thio) carbamoyl halide.

(A) The reaction by using of (thio) isocyanate can be executed by reacting a compound represented by formula (II)

(II)

wherein all symbols have the same meanings as defined above with (thio) isocyanate represented by formula (III)

$R^{3-A}$—N=C=W       (III)

wherein all symbols have the same meaning as the above.

This reaction is executed at 0° C.-reflux temperature in organic solvent such as toluene, benzene, xylene, tetrahydrofuran, dichloromethane and diethyl ether.

It is preferable that this reaction is executed under water free condition in inert gas.

The (thio) isocyanate compound represented by formula (III) is well-known or can be manufactured according to well-known methods (for example, the following (a), (b) or (c)).

(a) The (thio) isocyanate compound represented by formula (III) is obtained by reacting an amine compound represented by formula (IV)

$R^{3-A}$—NH$_2$       (IV)

wherein R$^{3-A}$ have the same meanings as defined above with a phosgene compound such as phosgene, thiophosgene, and triphosgene (bis(trichloromethyl) carbonate).

This reaction is well-known and can be executed by reacting the amine compound with the phosgene compound at −20° C.-reflux temperature in organic solvent (ether solvents, etc. such as diethyl ether and tetrahydrofuran). It is preferable that this reaction is executed under water free condition in inert gas.

(b) In the compounds represented by formula (III), a compound wherein W is an oxygen atom, i.e., an isocyanate compound can be manufactured by rearrangement reaction.

As the rearrangement reaction, Curtius rearrangement, Hofmann rearrangement, Rossen rearrangement, and Schmidt rearrangement, etc. are enumerated. Though these reactions can be easily understood for the persons skilled in the art, for example, in Cltius rearrangement, the isocyanate compound is obtained by reacting the compound represented by formula (V)

$R^{3-A}$—COOH (V)

wherein $R^{3-A}$ has the same meaning as the above in inert organic solvent (toluene, benzene and xylene, etc.), at 60° C.-reflux temperature, in the existence of bases (triethylamine, diisopropyl ethylamine, dimethylaminopyridine and pyridine, etc.) and diphenylphosphorylazide.

It is preferable that this reaction is executed under water free condition in inert gas.

(c) The (thio) isocyanate compound represented by formula (III) is obtained by reacting the amine compound represented by formula (IV) at −20° C.-reflux temperature in the existence of CDI (carbonyldiimidazole) or TCDI (thiocarbonyldiimidazole), in inert organic solvent (ethyl acetate, tetrahydrofuran, dichloromethane, chloroform, benzene and toluene, etc.).

It is preferable that this reaction is executed under water free condition in inert gas.

The (thio) isocyanate compound represented by formula (III) obtained by the method of (a), (b) or (c) can be used to manufacture the compound represented by formula (I-A-1) by reacting with the compound represented by formula (II) after or in the isolation.

(B) The method using (thio) carbamoyl halide is executed by reacting (thio) carbamoyl halide represented by formula (XIV)

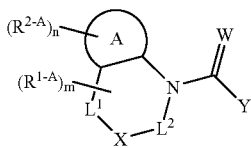

(XIV)

wherein Y represents a halogen atom, and other all symbols represent the same meaning as the above with an amine compound represented by formula (XV)

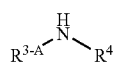

(XV)

wherein all symbols have the same meaning as the above.

This reaction is well-known, for example, is executed by reacting the compound represented by formula (XV) with the one represented by formula (XIV) at 0° C.-reflux temperature in the existence of bases (pyridine, triethylamine, dimethylaniline, dimethylaminopyridine and diisopropyl ethylamine, etc.), in organic solvent (chloroform, dichloromethane, diethyl ether and tetrahydrofuran, etc.).

The compound represented by formula (XIV) can be manufactured by reacting the compound represented by formula (II) at −20° C.-reflux temperature, in the existence of a phosgene compound (phosgene, thiophosgene and triphosgene (bis(trichloromethyl)carbonate), etc.) and bases (pyridine, triethylamine, dimethylaniline, dimethylaminopyridine and diisopropyl ethylamine, etc.), in organic solvent (chloroform, dichloromethane, diethyl ether and tetrahydrofuran, etc.) or without solvent.

(2) In the compound represented by formula (I-A), the compound which $R^4$ is C1-8 alkyl, i.e., the compound represented by formula (I-A-2)

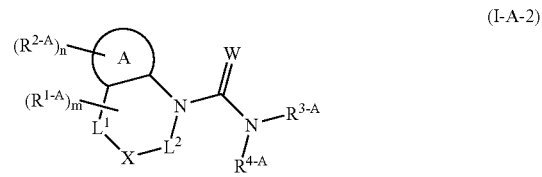

(I-A-2)

wherein $R^{4-A}$ represents C1-8 alkyl, and other symbols represent the same meanings as defined above can be manufactured by N-alkylation of the compound represented by formula (I-A-1).

The N-alkylation is executed by reacting with a base (sodium hydride, triethylamine, dimethylaminopyridine or pyridine, etc.) in −78° C.-reflux temperature in the existence or absence of an alkylating agent (methyl iodide, ethyl iodide or propyl iodide, etc.)

It is preferable that this reaction is executed under water free condition in inert gas.

(3) The compound represented by formula (I-A) can be manufactured by reacting the compound represented by formula (VI)

(VI)

wherein all symbols have the same meanings as defined above with the compound represented by formula (II).

This reaction can be executed in inert organic solvent (pyridine or dimethylaminopyridine, etc.) or without solvent in the existence of a tertiary amine (pyridine or dimethylaminopyridine, etc.) at 0° C.-reflux temperature.

It is preferable that this reaction is executed under water free condition in inert gas.

(4) In the compounds represented by formula (I-A), the compound which $R^3$ and $R^4$ are both hydrogen atoms, i.e., the compound represented by formula (II) can be manufactured by reacting the compound represented by formula (I-A-3)

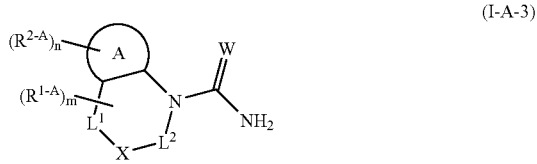

wherein all symbols have the same meanings as defined above with sodium cyanate.

This reaction can be executed at 60° C.-reflux temperature in inert organic solvent (acetonitrile etc.).

It is preferable that this reaction is executed under water free condition in inert gas.

This reaction can be executed in organic solvent (N,N-dimethylformamide, dioxane, tetrahydrofuran or diethyl-ether, etc.) at 0° C.-reflux temperature by reacting the compound represented by formula (XIV) with ammonium carbonate.

[2] In the compounds represented by formula (1), the compound that contains at least a free amino, hydroxyl, carboxyl or mercapto, i.e., the compound represented by formula (I-B)

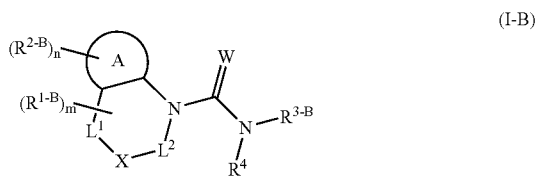

wherein all symbols have the same meanings as defined above can be manufactured by the deprotection reaction of protecting groups of amino, hydroxyl, carboxyl, or mercapto of the compound represented by formula (I-A).

As the protecting groups of amino, for example, benzyloxycarbonyl, t-butoxycarbonyl, trifluoroacetyl, and 9-fluorenylmethoxycarbonyl are included.

As the protecting groups of hydroxyl, for example, methoxymethyl, 2-tetrahydropyranyl, tert-butyldimethylsilyl, tert-butyldiphenylsilyl, acetyl and benzyl are included.

As the protecting groups of carboxyl, for example, methyl, ethyl, tert-butyl and benzyl are included.

As the protecting group of mercapto, for example, benzyl, methoxybenzyl, methoxymethyl, 2-tetrahydropyranyl, diphenylmethyl and acetyl are included.

The protecting group of amino, hydroxyl, carboxyl and mercapto only has to be a group that can be removed easily and selectively besides the above and is not especially limited. For example, the group described in T. W. Greene, *Protective Groups in Organic Synthesis*, Third Edition, Wiley, New York, and 1999 is used.

The deprotection reactions of the protecting groups of amino, hydroxyl, carboxyl, or mercapto are known well, for example, (1) a deprotection reaction under alkaline condition,
(2) a deprotection reaction under acid condition,
(3) a deprotection reaction by hydrolysis, and
(4) a deprotection reaction of silyl, etc. are included.

These methods are concretely explained as follows, (1) The deprotection reaction under alkaline condition may be carried out at 0-40° C., for example, in an organic solvent (methanol, tetrahydrofuran, dioxane or dimethyl formamide, etc.), using an alkali metal (sodium hydroxide, potassium hydroxide or lithium hydroxide, etc.), an alkaline earth metal (barium hydroxide or calcium hydroxide, etc.), an organic amine (triethylamine, N-methylmorpholine, diisopropylethylamine or piperidine, etc.), a quaternary ammonium salt (tetrabutylammoniumfluoride, etc.) or the solution, or these mixture.

(2) The deprotection reaction under acid condition may be carried out at 0-100° C., for example, in an organic solvent (methylene chloride, chloroform, dioxane, ethyl acetate or anisole, etc.), an organic acid (acetate, trifluoroacetic acid or methanesulfonic acid, etc.), an inorganic acid (hydrochloric acid or sulfate, etc.), or these mixture (hydrogen bromide/acetate, etc.).

(3) The deprotection reaction by hydrolysis may be carried out at 0-200° C., for example, in a solvent (ethers (tetrahydrofuran, dioxane, dimethoxyethane or diethylether, etc.), alcohols (methanol or ethanol, etc.), benzenes (benzene or toluene, etc.), ketones (acetone or methyl ethyl ketone, etc.), nitriles (acetonitrile etc.), amides (dimethyl formamide etc.), water, ethyl acetate, acetate, or two or more mixed solvent(s) thereof, etc.), under the presence of a catalyst (palladium-carbon, palladium black, hydroxide palladium, platinum oxide or raney nickel, etc.), under atmospheric or pressurized hydrogen atmosphere or formate ammonium.

The compound with amino groups can be manufactured from the above hydrolysis reaction of the compound with nitro groups.

(4) The deprotection reaction of silyl groups may be carried out at 0-40° C., for example, in an organic solvent (tetrahydrofuran or acetonitrile, etc.) that can be mixed with water, using tetrabutylammoniumfluoride.

[3] In the compounds represented by formula (I), a compound whose at least one of $R^1$ is an oxo can be manufactured from oxidation reaction of the corresponding compound (the compound whose one of $R^1$ is a hydroxy).

The oxidation reaction is well-known, for example, (1) a method using Swan oxidation,
(2) a method using Dess-Martin reagent, and
(3) a method using TEMPO reagent etc. are enumerated.

These methods are concretely explained as follows, (1) The method using Swan oxidation is executed, for example, by reacting an alcoholic compound to solution obtained by reacting oxalyl chloride with dimethyl sulphoxide at −78° C. and reacting with tertiary amine (triethylamine etc.) at −78-20° C. in inert organic solvent (chloroform or dichloromethane, etc.).

(2) The method using Dess-Martin reagent is executed, for example, by the reaction at 0-40° C. in inert organic solvent (chloroform or dichloromethane, etc.) in the existence of Dess-Martin reagent (1,1,1-triacetoxy-1,1-dihydro-1,2-benzoiodoxole-3-(1H)-one).

(3) The method using TEMPO reagent is executed by reacting at 20-60° C. in a inert organic solvent (chloroform or dichloromethane, etc.) in the existence of tempo reagent (2,2,6,6-tetramethyl-1-piperidinyloxy, free radical) and iodobenzene diacetate.

It is preferable that all of (1), (2), and (3) reaction are executed under water free condition in inert gas (argon or nitrogen, etc.).

As this oxidation reaction, the one that can oxidize alcohol into ketone easily and selectively is not limited besides the above. For example, Jones oxidation, oxidation with pyridinium chlorochromate (PCC), and oxidation using sulfur trioxide and pyridine complex, the one described in "*Comprehensive Organic Transformations*" (VCH Publishers, Inc., and (1989) 604-614) are used.

Although the persons skilled in the art can understand easily, the aimed present compound can be easily manufactured by using these reactions properly.

On each reacting in this specification, the reaction product can be purified by a usual purification means, for example, distillation under normal pressure or decompression, high performance chromatography using silicagel or magnesium trisilicate, or washing and recrystallization, etc. The purification may be executed at each reaction, or after some reactions.

Other starting materials and each reagent in the reaction, which are well-known or can be manufactured by well-known methods.

For example, in the compounds represented by formula (II), a compound represented by formula (II-1)

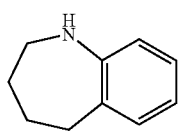
(II-1)

is known as CAS No. 4424-20-8.

A compound represented by formula (II-2)

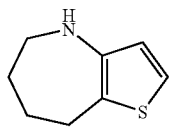
(II-2)

and a compound represented by formula (II-3)

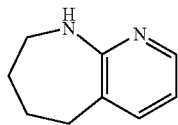
(II-3)

can be manufactured by the method described in "*Bioorg. Med. Chem. Lett.*" 2000, 695-698 or the similar method.

Additionally, the compound represented by formula (II) can be manufactured, for example, according to a method represented by the following reaction process, a method represented on "*J.C.S.* 1957, 2312", "*J.C.S.* 1961, 3989", "*J. Med. Chem.* 2000, 4388-4397", or methods represented by the postscript examples.

For example, a compound of which methylene is adjacent to nitrogen atoms in ring composed by $L^1$ and $L^2$, i.e., a compound represented by formula (II-A) can be manufactured according to the method represented by reaction process 1.

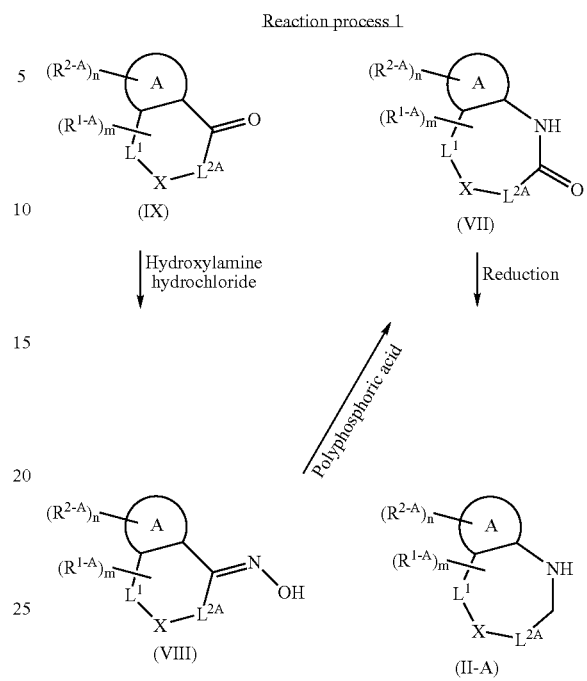

In the reaction process, $L^2$ is composed with -$L^{2A}$- and the adjacent methylene and other symbols have the same meanings as defined above.

For example, a compound which $L^1$ represents single bonds, X represents an oxygen atom, and $L^2$ represents trimethylene, i.e., the compound represented by formula (II-B) can be manufactured by a method represented by the following reaction process.

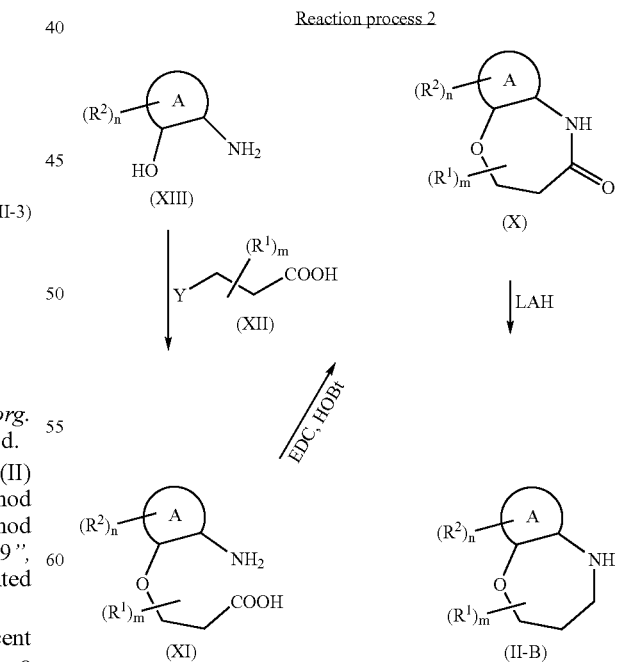

In the reaction process, LAH represents lithium hydride aluminum, EDC represents 1-ethyl-3-[3-(dimethylamino)

propyl]carbodiimide hydrochloride, HOBt represents 1-hydroxybenzotriazole, and other symbols have the same meanings as defined above.

In compounds used as a departure compound, for example, a compound represented by formula (IX-1) in the compounds represented by formula (IX)

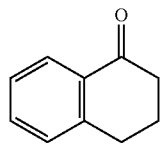

(IX-1)

is known as CAS No. 529-30-4. A compound represented by formula (IX-2)

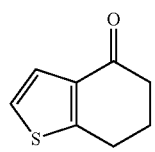

(IX-2)

is known as CAS No. 13414-95-4.

The compounds represented by formula (III), (IV), (V), (VI), (IX), (XII), (XIII), and (XV) are well-known, or can be manufactured according to a well-known method.

The present invention compound represented by formula (I) can be manufactured by the method in examples besides the above method or the similar method.

Salts

The compounds represented by formula (I) in the present invention may be converted into pharmaceutically acceptable salts by a well-known method. As the pharmaceutically acceptable salts, alkaline metal salts, alkaline earth metal salts, ammonium salts, amine salts, and acid addition salts, etc. are included.

As the alkaline metal salts, alkaline earth metal salts, ammonium salts, and amine salts, the water-soluble salts without toxicity are preferable. As these suitable examples, the alkali metal salts (potassium or sodium, etc.), the alkaline earth metal salts (calcium or magnesium, etc.), the ammonium salts (tetramethylammonium, etc.), pharmaceutically acceptable organic amine salts (triethylamine, methylamine, dimethylamine, cyclopentylamine, benzylamine, phenethylamine, piperidine, monoethanolamine, diethanolamine, tris(hydroxymethyl)methylamine, lysine, arginine, or N-methyl-D-glucamine, etc.) are included.

As the acid-addition salts, water-soluble salts without toxicity are preferable. As the suitable acid-addition salts, for example, inorganic acid salts such as hydrochloride, hydrobromate, hydroiodate, sulfate, phosphate, and nitrate, etc, and organic acid salts such as acetate, trifluoroacetate, lactate, tartrate, oxalate, fumarate, maleate, benzoate, citrate, methane sulfonate, ethane sulfonate, benzene sulfonate, toluene sulfonate, isethionate, glucuronate, gluconate, etc. are included.

The compounds of the present invention represented by formula (I) and salt thereof can be converted into the solvate by well-known methods.

As the solvates, the water-soluble one without toxicity are preferable. The appropriate solvates, for example, solvates such as water, alcohol solvents (ethanol, etc.), etc. are included.

Pharmacological Activity

The present invention provides materials with MBR antagonism, which antagonizes to diazepam binding inhibition protein (Diazepam binding inhibitor; DBI) that increases by stressor and the metabolic product on MBR and returns the balance of excitable or inhibitory signal transduction to tone by controlling excessive neurosteroid production via MBR.

The present invention provides the preventive and treatment medicines against diseases caused by stress, which comprises with a material with MBR antagonism as an active ingredient.

The present invention provides the preventive and treatment medicines against exacerbative and recrudescent diseases caused by stressors, which comprises a material that controls the abnormal increase of steroid production at stress via MBR as an active ingredient.

The compounds of the present invention represented by formula (I) have actions that control the increase of neurosteroid production by MBR agonist via MBR. As the result, the compounds of the present invention have actions that recover working of nerve, immunity, and endocrine system by controlling the abnormal increase of steroid production caused by stressors and recoverring the balance of excitable or inhibitory signal transduction changed by neurosteroids.

Under load of stressors to organism, amounts of various neurosteroid as the metabolites increase by increasing production of pregnenolone via MBR in mitochondria of glia cells. Since neurosteroids positively or negatively modulates the function of each kind of various receptors and ion channels, the change of activity of nervous, immune, and endocrine system variously adjusted by these nervous systems and diseases related to various stresses are caused by the collapse of balance of excitable or inhibitory signal transduction. The medicine of the present invention recovers the function of nerve, immunity, and endocrine system, which is accompanied by the control of anomalous increasing production of neurosteroid by the activation of MBR.

The present compound, which can bind to MBR, acts as a competitive antagonist against MBR agonist to increase neurosteroid production by binding to this receptor [for example, FGIN 2-[2-(4-fluorophenyl)-1H-indol-3-yl]-N,N-dihexylacetamide:"$J.$ Pharmaco. Exp. Ther., 262, 971-978, 1992"]. It is thought that the present compound demonstrates an anti-stress action by acting as an antagonist against MBR and antagonizing the increasing activity of steroid production caused by endogenous MBR ligands.

Therefore, the present compound is characterized in (a) the action that controls steroid production by MBR agonists, and (b) based on the depression of steroid production, the expression of the anti-stress action by decreasing neurosteroid followed to return the balance of the excitable or inhibitory signal transduction to be normal. The identification means of the above feature has been described on this specification.

The present compound having MBR antagonism can prevent and/or treatment for exacerbative and recrudescent diseases caused by stressors by returning the balance of the excitable or inhibitory signal transduction to normal by suppression of neurosteroid production and recoverring the function of nerve, immunity, and endocrine system. Identification means of action as MBR antagonist and anti-stress action of MBR antagonist are concretely explained in experiment examples on this specification.

It was proved by the following experiments that the present compound represented by formula (I) has MBR antagonistic activity and that it is effective for the diseases caused by stress.

In the following experimental examples, PK11195 is MBR ligand [1-(2-chlorophenyl)-N-methyl-N-(1-methylpropyl)-3-isoquinoli necarboxamide: "Eur. J. Pharmacol., 119, 153-167, 1985"], FGIN1-27 is MBR agonist [2-[2-(4-fluorophenyl)-1H-indol-3-yl]-N,N-dihexylacetamide:"J. Pharmacol. Exp. Ther., 262, 971-978, 1992"].

Experiment 1: Receptor Binding

The affinity of the compound to MBR was determined using rat brain membrane preparation. After male wistar rats were decapitated followed to remove the whole brain, cerebellums were removed. They were homogenized in ice-cold 50 mmo/L Tris-HCl buffer (pH7.4) and the homogenates were centrifuged at 12,000 g for 20 min (4° C.), and then their supernatants were discarded. The residual pellets were washed in the same buffer. The pellets resuspended in 50 mmo/L Tris-HCl buffer (pH7.4) and adjusted to about 1 mg/mL were used as rat brain membrane preparations for binding assay. The binding assay was experimented using [3H]PK11195 as a selective MBR ligand.

To determine the amount of total binding in saturation binding study, membrane preparations, various concentrations of [$^3$H]PK11195, final concentraion: 0.5 vol % dimethylsulfoxide (DMSO) and 50 mmo/L Tris-HCl buffer (pH7.4) (total volume of 200 μL) were incubated for 1 hour at room temperature. To determine the amount of non-specific binding, 20 μmol/L of PK11195 was added in place of DMSO were incubated for 1 hour. The mixture rapidly was filtrated on GF/B filter soaked with 0.3% polyethyleneimine using cell harvester, which was washed twice with 50 mmo/L Tris-HCl buffer (pH7.4). After drying, the radioactivity on the filer was measured by liquid scintillation counter. The data were analyzed using analysis soft KELL (Ver. 6, BIOSOFT). The dissociation constant ($K_D$ value) was determined by using scatchard analyses.

To determine the amount of total binding in competition binding study, membrane preparation, final concentraion: 1 nmol/L of [$^3$H]PK11195, final concentraion: 0.5 vol % of DMSO and 50 mmol/L Tris-HCl buffer (pH7.4) (the total volume of 200 μL) were incubated for 1 hour at room temperature. To determine the amount of non-specific binding, 20 μmol/L of PK11195 was added in place of DMSO, on the other hand, to determine the affinity of the invention, final concentraion: 10 pmol/L to 1 μmol/L of the compound dissolved in DMSO was incubated in place of DMSO. The reaction was terminated as above described 1 hour later, then radioactivity on the filer was measured by liquid scintillation counter. The concentration of the compound required to reduce [$^3$H]PK11195 binding to 50% of the amount of specific binding of [$^3$H]PK11195 ($IC_{50}$ value) were derived from the data obtained. The inhibitory constant ($K_i$ value) was derived according to the equation of Cheng & Prusoff (Biochem. Pharmacol., 22, 3099-3108, 1973). The $K_i$ values of the compounds of the present invention are shown in table 6. These results clearly indicate that these compounds have high affinity to MBR.

TABLE 6

| Example Num | Ki (nM) |
|---|---|
| 7 (5) | 5.5 |
| 7 (18) | 0.09 |
| 14 | 32 |

Experiment 2: Determination of Pregnenolone in Rat Adrenocortical Mitochondria

The steroid productivity of the present compound was evaluated using rat adrenocortical mitochondria.

After intraperitoneal administration of 20 mg/mL (1 mL) cycloheximide, 10 IU/mL (0.3 mL) adrenocorticotropic hormone (ACTH) was intraperitoneally administered to Male SD rats 5 minutes later. Then, rats were sacrificed by cervical dislocation 20 minutes later and bilateral adrenal cortexes were extirpated at once. The extirpated adrenal cortexes were homogenized in buffer A (50 mmol/L Tris-HCl, 250 mmol/L Succrose) followed to be centrifuged at 2,000 g for 3 min (4° C.). The supernatant was centrifuged at 12,500 g for 10 min (4° C.). The residual pellet was resuspended in buffer A followed to be centrifuged at 12,500 g for 10 min (4° C.). The pellet was washed again and finally suspended in buffer B (250 mmol/L Succrose, 10 mmol/L potassium phosphate buffer, 15 mmol/L triethanolamine, 20 mmol/L potassium chloride, 5 mmol/L magnesium chloride, 10 μmol/L trilostane, 10 μmol/L SU10603) for experiments. Malate (150 mmol/L), β-NADP$^+$ (5 mmol/L) and the compound in a total volume of 25 μL were incubated for 5 min at 37° C. Then, 225 μL of mitochondrial membrane fraction from rat adrenal cortexes in buffer B preincubated for 5 min at 37° C. was added, then further incubated for 10 min at 37° C. to produce pregnenolone (final concentration of the compound: 1 μmol/L). The reaction was terminated by addition of ethanol (1 mL) and the organic phase extracted with n-hexane (1.25 mL) was collected and evaporated. The residual was dissolved in buffer C (0.1% gelatin in phosphate buffered saline) followed to be centrifuged at 12,000 g for 5 min, and the supernatant was collected as a sample for determination. [$^3$H]Pregnenolone (10,000 cpm, 100 μL), pregnenolone antibody (ICN Biomedicals Inc, 100 μL) and sample (100 μL) were mixed and incubated overnight at 4° C. Then, dextran/charcoal (200 μL) was added to the mixture, which was mixed well and was kept on ice for 10 min, and was centrifuged at 1,000 g for 10 min (4° C.). The radioactivity of the supernatant was measured by liquid scintillation counter. The pregnenolone content in the sample was calculated from standard curve. Though pregnenolone content in FGIN1-27 treated group was higher than that in DMSO treated group, in the present compound treated group was as same as that in DMSO treated group. These results indicated that the present compound did not influence pregnenolone production in DMSO treatment group though FGIN1-27 is a MBR agonist which increase pregnenolone production more than in DMSO treated group.

Experiment 3: Measurement of MBR Antagonist Activity in Rat Adrenocortical Mitochondria The effects of the compounds of the present invention on 1 nmol/L of FGIN1-27-stimulated pregnenolone production in an experiment according to the method described in Example 2 indicated that the compounds of the present invention antagonizes to steroid-productive action of MBR agonist.

Experiment 4: Effect of the Present Compound on Increase in Pregnenolone Production in the Brain Under Stress.

Psychological stress was loaded to male Wistar rats (Brain Res., 641, 21-28, 1994). Water was saved up to the depth of about 10 cm in a container where the platform had been installed at the center. The vehicle or the compound was orally administered to the rats in the stressed group though neither administering nor stressor were loaded to the rats in the non-treated group. The stressor was loaded to the rat put on the platform 30 minutes later, and the bilateral hippocampus were removed and weighed after microwave (output: about 6.5 kW, exposure time: 0.96 s) was irradiated with a microwave applicator(Muromachi Kikai Co., Ltd.) 1 hour later from stress loading. Internal standard substance (D4-pregnenolone 20 ng), water (1 ml), and diethyl ether/n-hexane (3 ml) (9:1) were added to the crushed hippocampus and stirred. After being crushed by supersonic wave and stirred again, the organic layer obtained by centrifugal for 5 minutes at 3,000 rpm was transferred to a new tube with pasteur pipet. The water phase were extracted with diethyl-ether/n-hexane (9:1) again, then the organic phase were added to the preserved one. The residual dried under reduced pressure were dissolved in 150 μL of $H_2O$/acetonitrile (1:9), and then was measured by LC-MS. The measurement conditions are as follows.

LC: Hewlett Packard series 1100;
Column: Inertsil ODS-3, 3 μm, $2.19^\Phi \times 100$ mm;
Temperature: room temp.;
Mobile phase: 5 mmol/L $CH_3CO_2NH_4$/MeCN (10:90);
Flow rate: 0.2 mL/min;
Injection vol.: 40 μL.
MS: Quattoro II (Micromass);
Ionization mode: Atmosphere Pressure Chemical Ionization (APcl);
positive; Corona: 3.4 kV;
Sheath gas: $N_2$ (50 L/hr);
Source temperature: 180° C.;
Probe temperature: 550° C.;
Detection: Pregnenolone: m/z 317.2 (cone: 10 V);
$D_4$-pregnenolone:m/z 321.2 (cone: 10 V).

Pregnenolone content in hippocampus of vehicle-treated group significantly increased compared with that in non-stressed group. On the other hand, the increase of pregnenolone content was significantly inhibited in the group to which 3-30 mg/kg of the present compound was orally administered. These results indicate that the compounds of the present invention inhibit increase of pregnenolone content in hippocampus on stress.

Experiment 5: Evaluation of Anti-Stress Effects of MBR Antagonists.

Psychological stress was loaded to male Wistar rats (Brain Res., 641, 21-28, 1994). Water was saved up to the depth of about 10 cm in a container where the platform had been installed at the center. A stressor load was begun 30 minutes after the vehicle or the present invention compound was orally administered. The number of defecation was counted (10 per each group) 1 hour later. Rats without administeration and the load of stressor did not rarely defecated for 1 hour. On the other hand, remarkable defecation was admitted in media treatment group which the stressor had been loaded. However, it turned out that the number of defecation in the present compound treated group was significantly suppressed more than the vehicle one. These results clearly indicate that MBR antagonists have anti-stress effects.

Toxicity

The toxicities of the compounds of the present invention are very low and are safe enough for pharmaceutical use.

INDUSTRIAL APPLICABILITY

Application to Pharmaceuticals

Since the compounds of the present invention represented by formula (I) antagonize MBR, it is thought that they could be useful for the prevention and/or treatment of diseases induced, exacerbated or reignited by stress.

The diseases induced, exacerbated or reignited by stress include, digestive system diseases (functional dyspepsia, gastric and duodenal ulcer, ulcerative colitis, irritable bowel syndrome, biliary dyskinesia, esophageal spasm, gastric atony, aerophagia, chronic hepatitis, chronic pancreatitis, etc.), circulatory system diseases (essential hypertension, essential hypotension, (nervous) angina pectoris, arrhythmia, orthostatic dysregulation, myocardial infarction, arteriosclerosis, vertigo, etc.), endocrine and metabolic diseases (neural anorexia, hyperphagia, Bartter syndrome, cachexia exophthalmica, diabetes, psychogenic polydipsia, obesity, reflex hypoglycemia, etc.), respiratory system diseases (bronchial asthma, hyperventilation syndrome, laryngeal spasm, chronic obstructive pulmonary diseases, etc.), nervous and muscular system diseases (migraine, catatonic headache, migrainous neuralgia, post-traumatic stress disorder, dissociated disturbance, panic disorder, anxiety, depression, insomnia, nervous vomiting, nervous coughing, neurosis, autonomic dystonia, reactive depression, psychogenic raptus nervorum, psychogenic faint, maladjustment to job, burnout syndrome, chronic fatigue syndrome, writer's cramp, spasmic torticollis, etc.), dermatosis (chronic urticaria, atopic dermatitis, hyperhidrosis, eczema, dermal pruritus, alopecia areata, systemic lupus erythematosus, etc.), surgery diseases (postoperative abdominal neurosis, dumping syndrome, polysurgery, plastic postoperative neurosis, etc.), orthopedic diseases (rheumatoid arthritis, low back pain, cervico-omo-brachial syndrome, stiff shoulder, cellulitis, polyarthralgia, systemic myalgia, gout, etc.), urinary and genital system diseases (bladder neurosis (neurogenic bladder), bed-wetting, enuresis, psychogenic anuresis, impotentia, prostatism, urethra syndrome, etc.), gynecological diseases (menopausal disorders, menstrual pain, menstrual disorder, premenstrual syndrome, infertility, frigidity, serious vomiting of pregnancy, abortus pregnancy immature birth, etc.), ophthalmologic diseases (asthenopia, central retinitis, myodesopsia, blepharospasm, primary glaucoma, etc.), otolaryngological diseases (tinnitus, dizziness, psychogenic deafness, empyema, allergic rhinitis, dysosmia, stammering, aphonia, etc.), oral surgery and dentistry diseases (temporomandibular arthrosis, glossopharyngeal neuralgia, sudden glossalgia, stomatitis, toothache, ozostomia, abnormal salivation, teeth gnashing, etc.), cancer, etc. are enumerated.

The compound represented by formula (I) or pharmaceutically acceptable salt thereof may be administered in combination with other pharmaceutical preparations as a combind drug, 1) to supplement and/or enhance the preventive and/or treatment effect of the compound,
2) to improve the kinetics/absorption of the compound and reduce the dose, and/or
3) to eliminate the side effect of the compound.

The combind drug comprising the compound represented by formula (I) and other pharmaceutical preparations may be administered in the form of combination drug with which both elements are mixed in a pharmaceutical preparation or may be administered in separate pharmaceutical preparations. When be administered by a separate pharmaceutical preparation, they may be administered simultaneously or by time interval. In the latter case, the compound represented by formula (I) may be administered first, the other pharmaceutical preparations may be post-administered. Alternatively, the other pharmaceutical preparations may be administered first, the compound represented by formula (I) may be post-administered. Each method for the administration may be same or different.

The disease on which prevention and the therapeutic potential are effective with the above combnd drug not be especially limited, but may be those for which the preventive and/or treatment effect of the compound represented by formula (I) is compensated for and/or enhanced.

For example, the other pharmaceutical preparations for compensating for and/or enhancing the preventive and/or treatment effect of the compound represented by formula (I) on irritable bowel syndrome include antianxiety drugs (benzodiazepine drugs, thienodiazepine drugs, non-benzodiazepinedrugs, etc.), antidepressant drugs (monoamine liberating agent, monoamine oxidase inhibitor, monoamine reuptake inhibitor (SNRI, SSRI), dopamine (D2) antagonist, CRF antagonist, β3 agonist, neurotensin antagonist, NK1 antagonist, tricyclic antidepressant drug, tetracyclic antidepressant drug, etc.), cholinergic-blocking agents, affinity polyacrylic resin, antidiarrheal drug, mucosal paralytic agent, bulk cathartic, saline purgatives, fiber formulation, drug for controlling intestinal function, autonomic nervous system modulator, calcium blocker, phosphodiesterase inhibitor, serotonin antagonist (5-HT$_3$ antagonist, 5-HT$_4$ antagonist), serotonin agonist (5-HT$_4$ agonist, 5-HT$_{1A}$ agonist), modulator of gastrointestinal tract function (CCK-A antagonist, β3 agonist, neurotensin antagonist, opioid agonist, NK$_1$ antagonist, NK$_2$ antagonist, 5-HT$_{1A}$ agonist, muscarine agonist, 5-lipoxygenase inhibitor, CRF antagonist), etc.

For example, the other pharmaceutical preparations for compensating for and/or enhancing the preventive and/or treatment effect of the compound represented by formula (I) on gastric and duodenal ulcer include, for example, acid reducer, histamine (H$_2$) receptor antagonist, proton-pump inhibitor, muscarine receptor antagonist, antigastric drug, antiulcer drugs (defensive factor enhancer, anti-pepsin drugs, prostaglandin derivatives, mesalazine, salazosulfapyrizine, etc.), anticholinergic drugs, gastric mucosa anesthetics, antidepressant and dopamine antagonist, etc.

For examples, the other pharmaceutical preparations for compensating for and/or enhancing the preventive and/or treatment effect of the compound represented by formula (I) on ulcerative colitis include, mesalazine, salazosulfapyrizine, antiulcer drug, anticholinergic agent, steroid agent, 5-lipoxygenase inhibitor, antioxidant, LTB$_4$ antagonist, local anesthetics, immunosuppressant, defensive factor enhancer, metalloprotease inhibitor, etc.

For examples, the other pharmaceutical preparations for compensating for and/or enhancing the preventive and/or treatment effect of the compound represented by formula (I) on bilary dyskinesia include, cerulein, spasmolytic agents, COMT (catechol-O-methyl transferase) inhibitor, cholinergic agent, anticholinergic agent, anxiolytic drug, cholagogue, antidepressant, CCK-A antagonist, etc.

For examples, the other pharmaceutical preparations for compensating for and/or enhancing the preventive and/or treatment effect of the compound represented by formula (I) on aerophagia include, drug for controlling intestinal function, anxiolytic drug, autonomic nerve modulator, fiber formulations, digestive exogenous enzyme, gas absorption agent, intestinal tract motion promotor.

For examples, the other pharmaceutical preparations for compensating for and/or enhancing the preventive and/or treatment effect of the compound represented by formula (I) on chronic hepatitis include hepatic hydrolysate drugs, polyenephosphatidylcholine, glycyrrhizinate formulations, protoporphyrin disodium, ursodeoxycholic acid, steroid drugs, cholinergic-blocking agents, antacidum, propagermanium, lipid peroxisome inhibitor, etc.

Examples of the other pharmaceutical preparations for compensating for and/or enhancing the preventive and/or treatment effect of the compound of formula (I) on chronic pancreatitis include, protease inhibitor, gastric acid secretion suppressant, antispasmodicantispasmodic agents (COMT inhibitor, antiserotonin drug, etc.), non-steroidal anti-inflammatory drug, central analgesics, sedatives, digestive enzyme formulation, acid reducer, H2 receptor antagonist, antidepressant, gastric mucosa local anesthetic, digestive function modulator (CCK-A antagonist), etc.

Examples of the other pharmaceutical preparations for compensating for and/or enhancing the preventive and/or treatment effect of the compound of formula (I) on throat spasms include, throat mobile function modulator, anxiolytic drug, autonomic nerve modulator, etc.

Examples of the other pharmaceutical preparations for compensating for and/or enhancing the preventive and/or treatment effect of the compound of formula (I) on gastric atony include, digestive function promotor, digestive enzyme formulation, tranquilizers, etc.

Examples of the other pharmaceutical preparations for compensating for and/or enhancing the preventive and/or treatment effect of the compound of formula (I) on functional dyspepsia include, acid reducer, H2 receptor antagonist, digestive function modulator, digestive function promoters, anxiolytic drug, tranquilizers, digestive enzyme formulation, proton pump inhibitor, muscarine receptor antagonist, anticholinergic agent, defensive factor enhancer, dopamine antagonist, etc.

Anxiolytic drugs include, for example, diazepam, oxazolam, flutazolam, alprazolam, ethyl loflazepate, tofisopam, etc.

Tricyclic antidepressants include, for example, amitriptyline, imipramine, clomipramine, nortriptyline, amoxapine, etc.

Tetracyclic antidepressants include, for example, maprotiline, mianserin, etc.

Acid reducers include, for example, sodium bicarbonate, magnesium oxide, dry aluminum hydroxide, aluminum silicate, etc.

H2 receptor antagonist includes, for example, famotidine, lanitidine, cimetidine, etc.

Proton pump inhibitors include, for example, omeprazole etc.

Muscarine receptor antagonists include, for example, pirenzepine hydrochloride, etc.

Defensive factor enhancers include, for example, sucralfate, aldioxa, teprenone, cetraxate hydrochloride, ornoprostil, etc.

Anti-pepsine drugs include, for example, sucralfate etc.

Prostaglandin derivatives include, for example, ornoprostil, misoprostol, etc.

Anticholinergic drugs include, for example, mepenzolate bromide, ipratropium bromide, etc.

Steroid drus include, for example, prednisolone, etc.

Topical anesthetics include, for example, cocaine hydrochloride, procaine hydrochloride, lidocaine, dibucaine hydrochloride, tetracaine hydrochloride, etc.

Immunosuppresants include, for example, cyclosporin, tacrolimus, azathiopurine, etc.

Autonomic nerve modulators include, for example, γ-oryzanol, etc.

Cholagogues include, for example, ursodesoxycholic acid, etc.

Drugs which adjust the function of gastrointestinal tract include, for example, metoclopramide, domperidone, trimebutine maleate, etc.

Drugs which assist the function of gastrointestinal tract include, for example, cisapride, bethanechol hydrochloride.

The weight proportion of the compound of formula (I) and the other pharmaceutical preparations is not specifically limited.

Arbitrary two or more of the other pharmaceutical preparations may be administered in combination.

Examples of the other pharmaceutical preparations for compensating for and/or enhancing the preventive and/or treatment effect of the compound of formula (I) include not only those which have so far been found but also those which will be found on the basis of the aforementioned mechanism.

To use the compound represented by formula (I) or pharmaceutically acceptable salt thereof, or a combind drug containing the compound represented by formula (I) and other medicines by the above purpose, it is usually administered systemically or locally, and orally or parenterally.

The dosage is determined depending on age, body weight, symptom, therapeutic effect, administration route, duration of the treatment and the like. Generally, 1 mg to 1000 mg per adult is orally administered once to several times per day, or 1 mg to 100 mg per adult is parenterally administered (preferably, nose drop, ophthalmic solution, ointment) once to several times per day, or intravenously administered for 1 to 24 hours per day, continuously.

Since the dose changes depending on various conditions as described above, there are cases in which doses lower than or greater than the above ranges may be used.

When the compound represented by the formula (I) or pharmaceutically acceptable salt thereof, or the combind drug containing the compound represented by the formula (I) and other medicines are administered, they are used as solid medicines, liquid medicines, and other compositions for internal use, and injections, external preparations, and suppositoriums, etc. for parenteral administration.

The solid compositions for oral administration include compressed tablets, pills, capsules, dispersing powders, granules, etc.

The capsules include hard capsules and soft capsules.

In such solid compositions, one or more active compound(s) is/are mixed with at least one inert diluent such as lactose, mannitol, glucose, hydroxypropyl cellulose, microcrystalline cellulose, starch, polyvinyl pyrrolidone or magnesium metasilicate aluminate. The compositions may also contain additional substances other than inert diluents, for example, lubricating agents such as magnesium stearate, disintegrating agents such as cellulose calcium glycolate, stabilizers such as lactose and solubilizers such as glutamic acid or asparatic acid according to usual methods. The tablets or pills may, if desired, be coated with film of gastric or enteric coating agents such as sugar, gelatin, hydroxypropyl cellulose or hydroxypropyl cellulose phthalate, or be coated with two or more films. Furthermore, capsules of absorbable materials such as gelatin are included.

The liquid compositions for oral administration include pharmaceutically acceptable emulsions, solutions, syrups and elixirs. In such liquid compositions, one or more active compound(s) is/are contained in inert diluents commonly used (purified water and ethanol, etc.). Furthermore, these compositions may also contain wetting agents, adjuvants such as suspending agents, sweetening agents, flavoring agents, perfuming agents, and preserving agents besides inert diluents.

The injections for parenteral administration in the present invention include sterile aqueous and/or non-aqueous solutions, suspensions and emulsions. The aqueous solutions or suspensions include, for example, distilled water for injection and a physiological salt solution. The non-aqueous solutions or suspensions include propylene glycol, polyethylene glycol, plant oil such as olive oil, alcohol such as ethanol, POLYSORBATE 80 (registered trade mark), and the like. They may be used mixing sterile aqueous or non-aqueous solutions, suspensions and emulsions. These compositions may contain preserving agents, wetting agents, emulsifying agents, dispersing agents, stabilizing agents (for example, lactose), and adjuvants such as solubilizer (glutamic acid and aspartic acid, etc.). These may be sterilized by filtrating through a bacteria-retaining filter, mixing with antimicrobial agents, or irradiation.

These may also be manufactured, for example, by making to be aseptic or dissolving to aseptic distilled water for injection or other solvents before use of sterile solid compositions.

As other compositions for parenteral administration, liquids for external use, ointments, liniments, inhalants, sprays, and pessaries for administering in vagina, which contain one or more activators and are prescribed with common procedure, are included.

The sprays may contain stabilizing agents such as sodium hydrogen sulfate, buffers to give isotonicity, and isotonic solutions such as sodium chloride, sodium citrate or citric acid besides inert diluents used generally. Processes for preparing the sprays have been described in U.S. Pat. Nos. 2,868,691 and 3,095,355.

BEST MODE FOR CARRYING OUT THE INVENTION

The following reference examples and examples illustrate the present invention, but do not limit the present invention.

The solvents in the parentheses in chromatographic separations or TLC show the developing or eluting solvents and the ratio shows volume ratio.

A solvent in parentheses in NMR shows the solvent for measurement.

In formula, TBS represents tert-butyldimethylsilyl, Ts represents toluenesulfonyl.

REFERENCE EXAMPLE 1

4-[(2-ethoxycarbonylphenyl)amino]-4-oxobutanoate

A mixture of which succinic anhydride (3.0 g) was added to toluene solution of 2-ethylaminobenzoate (4.96 g) was stirred at 115° C. The reactive mixture left at room temperature over night was extracted by 1N sodium hydroxide solution (40 ml) and water. Further, the extract that has been adjusted to pH 2 with 1N hydrochloric acid to the water layer was extracted by ethyl acetate. The organic layer that has been washed with the saturated brine was concentrated after drying with sulfuric anhydride sodium, and the title compound (6.57 g) having the following physical properties values was obtained.

TLC:Rf 0.42 (chloroform:methanol=9:1);

NMR (CDCl₃):δ 11.25 (b, 1H), 8.66 (d, J=8.4 Hz, 1H), 8.05 (dd, J=8.1 Hz, 1.8 Hz, 1H), 7.57-7.50 (m, 1H), 7.12-7.06 (m, 1H), 4.39 (q, J=7.2 Hz, 2H), 2.82-2.71 (m, 4H), 1.42 (t, J=7.2 Hz, 3H).

REFERENCE EXAMPLE 2

N-(2-ethoxycarbonylphenyl)-3-ethoxycarbonyl propanamide

A mixture of which thionyl chloride (1.9 ml) was dropped to ethanol (50 ml) solution of the compound (6.29 g) prepared in Reference example 1 during storage in ice was stirred at room temperature for 3 hours. The residue of the concentrated reactive mixture, which water is added, was extracted by ethyl acetate. The organic layer, which was washed with 1N hydrochloric acid, saturated sodium bicarbonate solution, and saturated brine, was concentrated after drying with sulfuric anhydride sodium. The residue was purified by silica gel column chromatography (n-hexane: ethyl acetate=5:1 to 2:1), and the compound (5.10 g) of the present invention with the following physical properties values was obtained.

TLC:Rf 0.26 (n-hexane: ethyl acetate=5:1);

NMR (CDCl₃):δ 11.19 (b, 1H), 8.69 (dd, J=8.4 Hz, 1.2 Hz, 1H), 8.04 (dd, J=8.1 Hz, 1.8 Hz, 1H), 7.56-7.49 (m, 1H), 7.10-7.04 (m, 1H), 4.39 (q, J=7.2 Hz, 2H), 4.21-4.10 (m, 2H), 2.82-2.71 (m, 4H), 1.42 (t, J=7.2 Hz, 3H), 1.26 (t, J=7.2 Hz, 3H).

REFERENCE EXAMPLE 3

5-hydroxy-4-ethoxycarbonyl-2,3-dihydro-1H-1-benzazepine-2-one

A mixture of which toluene (12 ml)/N,N-dimethylformamide (3 ml) solution of the compound (5.10 g) prepared in reference example 2 was dropped to toluene (5 ml)/N,N-dimethylformamide (2 ml) suspension of sodium hydride (4.18 g) during storage in ice was stirred at 70° C. for 1 hour. The removed deposit obtained by which acetate (8 ml) and water (20 ml) have been added to the radiationally cooled reactive mixture was dried, and the title compound (3.64 g) having the following physical properties values was obtained.

TLC:Rf 0.44 (n-hexane:ethyl acetate=1:1);

NMR (DMSO-d6):δ 12.55 (s, 1H), 10.32 (s, 1H), 7.78 (dd, J=8.1 Hz, 2.1 Hz, 1H), 7.56-7.49 (m, 1H), 7.28-7.22 (m, 1H), 7.17 (dd, J=8.7 Hz, 1.2 Hz, 1H), 4.29 (q, J=6.9 Hz, 2H), 2.93 (s, 2H), 1.30 (t, J=6.9 Hz, 3H).

REFERENCE EXAMPLE 4

2,5-dioxo-2,3,4,5-tetrahydro-1H-1-benzazepine

A mixture of which water (0.56 ml) was added to dimethyl sulphoxide (50 ml) solution of the compound (3.64 g) prepared in reference example 3 was stirred at 155° C. for 4 hours and half. The reactive mixture to which water has been added was extracted by the acetate. The organic layer that had been sequentially washed by 1N hydrochloric acid, saturated sodium bicarbonate solution, and saturated brine was concentrated after drying with sulfuric anhydride sodium. The residue was recrystallized from ethanol. A title compound (1.40 g) having the following physical properties values was obtained.

TLC:Rf 0.36 (n-hexane:ethyl acetate=1:1);

NMR (DMSO-d6):δ 10.06 (s, 1H), 7.80 (dd, J=9.0 Hz, 1.5 Hz, 1H), 7.56-7.49 (m, 1H), 7.19-7.12 (m, 2H), 2.92-2.86 (m, 2H), 2.67-2.62 (m, 2H)

REFERENCE EXAMPLE 5

5-hydroxy-2,3,4,5-tetrahydro-1H-1-benzazepine

A mixture of which the compound (175 mg) prepared in Reference example 4 has been added to diethyl ether (5 ml) suspension of lithium aluminum hydride (190 mg) was refluxed. 2N sodium hydroxide solution (1 ml) was added to the reactive mixture cooled up to room temperature. The residue of the filtrate which had been concentrated from the removed deposit was purified by silica gel column chromatography (n-hexane:ethyl acetate=3:2 to 1:1), and a compound (121 mg) of the present invention having the following physical properties values was obtained.

TLC:Rf 0.38 (n-hexane:ethyl acetate=1:1);

NMR: (CDCl₃):δ 7.27 (dd, J=7 Hz, 2 Hz, 1H), 7.10 (td, J=7 Hz, 2 Hz, 1H), 6.92 (td, J=7 Hz, 2 Hz, 1H), 4.79 (d, J=7 Hz, 1H), 3.25-3.05 (m, 2H), 2.97 (ddd, J=12 Hz, 9 Hz, 3 Hz, 1H), 2.19-1.99 (m, 2H), 1.88-1.70 (m, 1H).

REFERENCE EXAMPLE 6

5-(t-butyldimethylsilyloxy)-2,3,4,5-tetrahydro-1H-1-benzazepine

A mixture of which imidazole (355 mg) and tert-butyldimethylsilyl chloride (393 mg) have been added to N,N-dimethylformamide (1.7 ml) solution of the compound (283 mg) prepared in Reference example 5 was stirred at room temperature for 90 minutes. The residue obtained from the concentrated reactive mixture was purified by silica gel column chromatography (n-hexane: ethyl acetate=9:1), and a title compound (565 mg) having the following physical properties values was obtained.

TLC:Rf 0.42 (n-hexane:ethyl acetate=5:1);

NMR (CDCl₃):δ 7.52-7.48 (m, 1H), 7.06 (td, J=7.5 Hz, 1.5 Hz, 1H), 6.93 (td, J=7.5 Hz, 1.5 Hz, 1H), 6.71 (dd, J=7.5 Hz, 1.5 Hz, 1H), 4.77 (td, J=9.6 Hz, 2.4 Hz, 1H), 3.30-3.21 (m, 1H), 2.80-2.70 (m, 1H), 2.05-1.96 (m, 1H), 1.90-1.78 (m, 2H), 1.70-1.50 (m, 2H), 0.94 (s, 9H), 0.08 (s, 3H), 0.04 (s, 3H).

EXAMPLE 1

5-(t-butyidimethylsilyloxy)-1-phenylcarbamoyl-2,3,4,5-tetrahydro-1H-1benzazepine A mixture of which phenyl isocyanate (250 mg) had been added to toluene solution of the compound (560 mg) prepared in Reference example 6 was refluxed over night. The residue obtained from the concentrated reactive mixture was purified by silica gel column chromatography (n-hexane: ethyl acetate=9:1 to 7:1), and a title compound (655 mg) having the following physical properties values was obtained.

TLC:Rf 0.37 (n-hexane:ethyl acetate=5:1);

NMR (CDCl₃):δ 7.76 (bd, J=8.1 Hz, 1H), 7.46-7.38 (m, 1H), 7.37-7.16 (m, 6H), 7.04-6.94 (m, 1H), 6.09 (s, 1H), 4.90-4.83 (m, 1H), 4.80-4.53 (m, 1H), 2.72-2.60 (m, 1H), 2.18-1.98 (m, 2H), 1.76-1.48 (m, 2H), 0.94 (bs, 9H), 0.06 (bs, 6H).

EXAMPLE 2

5-hydroxy-1-phenylcarbamoyl-2,3,4,5-tetrahydro-1H-1-benzazepine

A mixture of which tetrabutylammoniumfluoride (1M, 2 ml) had been added to tetrahydrofuran (3 ml) solution of the compound (676 mg) prepared in Example 1 was stirred for 5 hours and half. The residue obtained from the concentrated reactive mixture was purified by silica gel column chromatography (n-hexane:ethyl acetate=2:1 to 1:2), and a title compound (459 mg) having the following physical properties values was obtained.

TLC:Rf 0.36 (n-hexane:ethyl acetate=1:1);

NMR (CDCl$_3$):δ 7.82-7.72 and 7.50-7.40 (b, 1H), 7.40-7.18 (b, 8H), 7.02-6.95 (m, 1H), 6.23 (bs, 1H), 5.00-4.87 (m, 1H), 4.70-4.50 (m, 1H), 2.80-2.55 (m 1H), 2.25-1.43 (m, 3H), 1.40-1.20 (m, 1H).

EXAMPLE 3

5-chloro-1-phenylcarbamoyl-2,3,4,5-tetrahydro-1H-1-benzazepine

A mixture of which thionyl chloride (0.44 ml) had been added to dichloromethane (5 ml) suspension of the compound (846 mg) prepared in Example 2 during storage in ice was stirred for 1 hour. The residue obtained from the concentrated reactive mixture has been extracted by ethyl acetate after adding of water. The organic layer that had been sequentially washed by 1N hydrochloric acid, saturated sodium bicarbonate solution, and saturated brine was concentrated after drying with sulfuric anhydride sodium. A title compound (879 mg) having the following physical properties values was obtained.

TLC:Rf 0.29 (n-hexane:ethyl acetate=2:1);

NMR (CDCl$_3$):δ 7.47-7.18 (m, 8H), 7.05-6.95 (m,1H), 6.08 (bs, 1H), 5.30-5.00 (m, 1H), 4.89-4.75 (m, 1H), 2.80-2.50 (m, 2H), 2.43-2.29 (m, 1H), 2.05-1.89 (m, 1H), 1.82-1.68(m, 1H).

EXAMPLE 4

5-cyano-1-phenylcarbamoyl-2,3,4,5-tetrahydro-1H-1-benzazepine

A mixture of which sodium cyanide (126 mg) had been added to N,N-dimethylformamide (5 ml) solution of the compound (291 mg) prepared in Example 3 was stirred at 60° C. over night. The reactive mixture to which water had been added was extracted by ethyl acetate. The organic layer sequentially washed by 1N hydrochloric acid, saturated sodium bicarbonate solution, and saturated brine was concentrated after drying with sulfuric anhydride sodium. The residue was purified by silica gel column chromatography (n-hexane:ethyl acetate=3:1), and a title compound (119 mg) having the following physical properties values was obtained.

TLC:Rf 0.24 (n-hexane:ethyl acetate=2:1);

NMR (CDCl$_3$):δ 7.88-7.79 (m, 0.5H), 7.54-7.20 (m, 7.5H), 7.06-6.98 (m, 1H), 6.19 (bs, 1H), 4.96-4.84 (m, 0.5H), 4.72-4.60 (m, 0.5H), 4.20-4.01 (m, 1H), 2.81-2.58 (m, 1H), 2.52-2.22 (m, 1.5H), 2.18-1.98 (m, 0.5H), 1.98-1.62 (m, 2H).

EXAMPLE 4(1)

1-phenylcarbamoyl-5-pyrrolidino-2,3,4,5-tetrahydro-1H-1-benzazepine hydrochloride A free body of the present compound was obtained by operation similar to the method represented in Example 4 using pyrrolidine instead of sodium cyanate. The obtained compound to which 4N hydrochloric acid-ethyl acetate solution has been added was concentrated. The residue was washed by diethyl ether, and the hydrochloride of the present compound having the following physical properties values was obtained.

TLC:Rf 0.41 (dichloromethane:ethyl acetate=1:1);

NMR (CDCl$_3$):δ 8.37 (d, J=7.5 Hz, 1H), 7.63-7.55 (m, 1H), 7.54-7.46 (m, 1H), 7.42-7.36 (m, 1H), 7.36-7.23 (m, 4H), 7.08-7.00 (m, 1H), 6.44 (s, 1H), 4.39-4.27 (m, 1H), 4.17-3.96 (m, 3H), 3.36-3.25 (m, 1H), 3.08-2.94 (m, 1H), 2.82-2.70 (m, 1H), 2.50-1.85 (m, 7H), 1.36-1.18 (m, 1H).

EXAMPLE 5

5-methoxymethyloxy-1-phenylcarbamoyl-2,3,4,5-tetrahydro-1H-1-benzazepine

A mixture of which diisopropyl ethylamine (37 µl) and methoxymethyl chloride (16 µl) have been added to tetrahydrofuran (0.2 ml) solution of the compound (50 mg) prepared in Example 2 was stirred over night. The reactive mixture has been extracted by ethyl acetate after adding of water. The organic layer sequentially washed by 1N hydrochloric acid, saturated sodium bicarbonate solution, and saturated brine was concentrated after drying with sulfuric anhydride sodium. The residue was recrystallized from n-hexane ethyl acetate. A compound (48 mg) of the present invention having the following physical properties values was obtained.

TLC:Rf 0.25 (n-hexane:ethyl acetate=3:1);

NMR (CDCl$_3$):δ 7.73-7.60 (b, 0.5H), 7.50-7.10 (b, 7.5H), 7.03-6.93 (b, 1H), 1H), 6.33-6.00 (b, 1H), 4.90-4.33 (b, 4H), 3.47-3.17 (b, 3H), 2.87-1.45 (m, 5H).

REFERENCE EXAMPLE 7

5-phenoxy-2,3,4,5-tetrahydro-1H-1-benzazepine

A mixture of which phenol (52 mg), triphenylphosphine (181 mg), and diethyl azodicarboxylate (40% toluene solution and 300 mg) had been added to tetrahydrofuran (2 ml) solution of the compound (75 mg) prepared in Reference example 5 was stirred for 1 hour. The residue obtained by concentrating the reactive mixture was purified by silica gel column chromatography (n-hexane:ethyl acetate=8:1 to 5:1), and a title compound (97 mg) having the following physical properties values was obtained.

TLC:Rf 0.39 (n-hexane:ethyl acetate=5:1);

NMR (CDCl$_3$):δ 7.38-7.34 (m, 1H), 7.28-7.19 (m, 4H), 7.10 (td, J=7.5 Hz, 1.5 Hz, 1H), 6.96-6.77 M, 3H), 5.33-5.27 (m, 1H), 5.00-4.60 (b, 1H), 3.38-3.30 (m, 1H), 2.91-2.81 (m, 1H), 2.30-2.20 (m, 1H), 1.97-1.80 (m, 3H).

EXAMPLE 6

5-phenoxy-1-phenylcarbamoyl-2,3,4,5-tetrahydro-1H-1-benzazepine

A mixture of which phenyl isocyanate (52 mg) had been added to toluene (10 ml) solution of the compound (95 mg) prepared in Reference example 7 was refluxed over night. The residue obtained by concentrating the reactive mixture was purified by silica gel column chromatography (n-hexane:ethyl acetate=5:1), and was recrystallized from n-hexane ethyl acetate. A present compound (65 mg) having the following physical properties values was obtained.

TLC:Rf 0.22 (n-hexane:ethyl acetate=5:1);
NMR (CDCl$_3$):δ 7.70-6.78 (m, 14H), 6.33 and 5.81 (bs, 1H), 5.46-5.35 (m, 1H), 4.82-4.60 (m, 1H), 2.84-2.70 (m, 1H), 2.70-2.10 (m, 2H), 1.88-1.67 (m, 2H).

EXAMPLE 6(1)

1-phenylcarbamoyl-5-(2-phenylcarbamoyloxyethyloxy)-2,3,4,5-tetrahydro-1H-1-benzazepine A present compound having the following physical properties values was obtained by operating as well as the method represented in Example 6, using the corresponding compound.

TLC:Rf 0.24 (n-hexane:ethyl acetate=2:1);
NMR (CDCl$_3$):δ 8.05-7.90 (bs, 1H), 7.50-6.65 (m, 14H), 6.37-6.03 (m, 1H), 4.76-4.63 (m, 1H), 4.59-4.52 (m, 1H), 4.49-4.30 (m, 1H), 3.89-3.62 (m, 2H), 3.50-3.38 (m, 1H), 2.88-2.60 (m, 1H), 2.47-2.23 (m, 2H), 1.70-1.40 (m, 2H).

REFERENCE EXAMPLE 8

5-(4-fluorophenyl) tetrahydrofuran-2-one

A mixture of which sodium borohydride (10.4 g) had been added to 1.5N sodium hydroxide solution (174 ml) of 3-(4-fluorobenzoyl) propanoic acid (51.2 g) at 50° C. was stirred at 50° C. for 15 minutes. The reactive mixture to which 6N hydrochloric acid (110 ml) had been added was stirred at 80° C. for 2 hours followed to be extracted by ethyl acetate. The extract washed with water and saturated brine was concentrated after drying with sulfuric anhydride magnesium. A title compound (46.7 g) having the following physical properties value was obtained.

TLC:Rf 0.34 (ethyl acetate: hexane=1:2);
NMR (CDCl$_3$):δ 7.38-7.26 (m, 2H), 7.15-7.03 (m, 2H), 5.54-5.44 (m, 1H), 2.76-2.56 (m, 3H), 2.29-2.04 (m, 1H).

REFERENCE EXAMPLE 9

7-Fluoro-4-(4-fluorophenyl)-1,2,3,4-tetrahydronaphthalene-1-one

A mixture of which trifluoromethane sulfonic acid (39 ml) has been added to fluorobenzene (50 ml) solution of the compound (15.9 g) prepared in Reference example 8 at room temperature was stirred with heating at 75° C. for 1 hour. The reactive mixture dissolved to water has been extracted by ethyl acetate. The extract sequentially washed by 1N hydrochloric acid, saturated sodium bicarbonate solution, and saturated brine was concentrated after drying with sulfuric anhydride sodium. The residue was recrystallized from n-hexane ethyl acetate. A compound (16.3 mg) of the present invention having the following physical properties values was obtained.

TLC:Rf 0.46 (ethyl acetate: hexane=1:4);
NMR (CDCl$_3$):δ 7.77 (dd, J=9.0 Hz, 2.7 Hz,1H), 7.20-6.91 (m, 6H), 4.29-4.23 (m, 1H), 2.80-2.58 (m, 2H), 2.51-2.39 (m, 1H), 2.33-2.18 (m, 1H).

REFERENCE EXAMPLE 10

7-fluoro-4-(4-fluorophenyl)-1-hydroxyimino-1,2,3,4-tetrahydronaphthalene

A mixture of which hydroxyamine hydrochloride (8.79 g) and sodium bicarbonate (10.6 g) have been added to methanol (125 ml) solution of the compound (16.3 g) prepared in Reference example 9 was refluxed. After the reaction, the residue obtained from the concentrated reactive mixture had been diluted with water followed to be extracted by ethyl acetate. The extract sequentially washed with water and saturated brine was concentrated after drying with sulfuric anhydride magnesium. A title compound (17.3 g) having the following physical properties value was obtained.

TLC:Rf 0.45 (ethyl acetate: hexane=1:4);
NMR (CDCl$_3$):δ 8.10 (br. s, 1H), 7.67 (dd, J=10.0 Hz, 2.4 Hz, 1H), 7.08-6.83 (m, 6H), 4.14-4.05 (m, 1H), 2.82-2.73 (m, 2H), 2.28-1.85 (m, 2H).

REFERENCE EXAMPLE 11

8-fluoro-5-(4-fluorophenyl)-2,3,4,5-tetrahydro-1H-1-benzazepine-2-one

A mixture of which the compound (17.3 g) prepared in Reference example 10 had been added to the mixed liquid of which polyphosphoric acid obtained by adding phosphorus pentoxide (260 g) to 85% phosphate (180 ml) had been heated at 130° C. was stirred for 5 minutes. The reactive mixture diluted with water was extracted by ethyl acetate. The organic layer sequentially washed with saturated sodium bicarbonate solution, water, and saturated brine was concentrated after drying with sulfuric anhydride magnesium. A title compound (6.9 g) having the following physical properties value was obtained.

TLC:Rf 0.20 (ethyl acetate: hexane=1:2);
NMR (CDCl$_3$):δ 8.03 (s, 1H), 7.28-7.19 (m, 2H), 7.12-7.03 (m, 2H), 6.80-6.66 (m, 3H), 4.40-4.28 (m, 1H), 2.65-2.42 (m, 4H).

REFERENCE EXAMPLE 12

8-fluoro-5-(4-fluorophenyl)-2,3,4,5-tetrahydro-1H-1-benzazepine

A mixture of which lithium aluminum hydride (3.86 g) had been added to tetrahydrofuran (250 ml) solution of the compound (6.93 g) prepared in Reference example 11 was refluxed for 1 hour. The reactive mixture to which 1N sodium hydroxide solution and water had been added was filtered with celite and was concentrated. A title compound (6.03 g) having the following physical properties value was obtained.

TLC:Rf 0.69 (ethyl acetate: hexane=1:2);
NMR (CDCl$_3$):δ 7.19-7.09 (m, 2H), 7.06-6.92 (m, 2H), 6.70-6.60 (m, 1H), 6.52-6.38 (m, 2H), 4.22-4.15 (m, 1H), 3.24-2.96 (m, 2H), 2.16-2.02 (m, 2H), 1.84-1.72 (m, 2H).

EXAMPLE 7

8-fluoro-5-(4-fluorophenyl)-1-phenylcarbamoyl-2,3,4,5-tetrahydro-1H-1-benzazepine A present compound having the following physical properties values was obtained by operating as well as the method represented in Example 1, using the compound prepared in Reference example 12 instead of the compound prepared in Reference example 6.

TLC:Rf 0.45 (n-hexane:ethyl acetate=2:1);
NMR (CDCl$_3$):δ 7.40-7.00 (m, 10H), 6.98-6.86 (m, 1H), 6.72-6.55 (m, 1H), 6.26 (brs, 1H), 4.75-4.64 (m, 1H), 4.24-4.15 (m, 1H), 2.94-2.78 (m, 1H), 2.30-2.10 (m, 2H), 1.95-1.78 (m, 2H).

The following compounds (Example 7-A and B) that was optically removed from this compound by using HPLC were obtained. The absolute configurations of these compounds, which have not been decided yet, represent either corresponding enantiomer.

EXAMPLE 7-A (−)-8-fluoro-5-(4-fluorophenyl)-1-phenylcarbamoyl-2,3,4,5-tetrahydro-1H-1-benzazepine TLC:Rf 0.43 (n-hexane:ethyl acetate=3:1);
NMR (CDCl$_3$):δ 7.40-7.00 (m, 10H), 6.96-6.86 (m, 1H), 6.69-6.58 (m, 1H), 6.30-6.20 (m, 1H), 4.74-4.60 (m, 1H), 4.23-4.14 (m, 1H), 2.94-2.76 (m, 1H), 2.26-2.08 (m, 2H), 1.96-1.78 (m, 2H); [α]$_D$=−8.52 (c=0.21, MeOH).

EXAMPLE 7-B (+)-8-fluoro-5-(4-fluorophenyl)-1-phenylcarbamoyl-2,3,4,5-tetrahydro-1H-1-benzazepine TLC:Rf 0.43 (n-hexane:ethyl acetate=3:1);
NMR (CDCl$_3$):δ 7.40-7.00 (m, 10H), 6.96-6.85 (m, 1H), 6.68-6.56 (m, 1H), 6.31-6.20 (m, 1H), 4.75-4.60 (m, 1H), 4.23-4.14 (m, 1H), 2.94-2.76 (m, 1H), 2.26-2.08 (m, 2H), 1.96-1.78 (m, 2H); [α]$_D$=+11.4 (c=0.21, MeOH).

EXAMPLE 7(1)-EXAMPLE 7(35)

Compounds of the present invention having the following physical properties values were obtained by operating as well as the method sequentially represented by (Reference example 8), Reference example 9, Reference example 10, Reference example 11, Reference example 12, and Example 7, using the corresponding compound.

EXAMPLE 7(1)

1-phenylcarbamoyl-2,3,4,5-tetrahydro-1H-1-benzazepine

TLC:Rf 0.51 (n-hexane:ethyl acetate=3:1);
NMR (CDCl$_3$):δ 7.35-7.19 (m, 8H), 7.02-6.95 (m, 1H), 6.22 (bs, 1H), 4.80-4.60 (m, 1H), 2.95-2.60 (m, 3H), 2.12-1.75 (m, 3H), 1.50-1.30 (m, 1H).

EXAMPLE 7(2)

5-phenyl-1-phenylcarbamoyl-2,3,4,5-tetrahydro-1H-1-benzazepine

TLC:Rf 0.33 (n-hexane:ethyl acetate=5:1);
NMR (CDCl$_3$):δ 7.43-6.95 (m, 13H), 6.68 (bd, J=7.2 Hz, 1H), 6.32 (bs, 1H), 4.74-4.64 (m, 1H), 4.34-4.20 (m, 1H), 2.92-2.80 (m, 1H), 2.30-2.10 (m, 2H), 2.02-1.80 (m, 2H).

EXAMPLE 7(3)

8-chloro-5-(4-chlorophenyl)-1-phenylcarbamoyl-2,3,4,5-tetrahydro-1H-1-benzazepine TLC:Rf 0.26 (n-hexane:ethyl acetate=5:1);
NMR (CDCl$_3$):δ 7.42-7.00 (m, 11H), 6.66-6.55 (m, 1H), 6.24 (bs, 1H), 4.74-4.62 (m, 1H), 4.22-4.12 (m, 1H), 2.92-2.76 (m, 1H), 2.26-2.06 (m, 2H), 1.96-1.78 (m, 2H).

EXAMPLE 7(4)

1-ethylcarbamoyl-8-fluoro-5-(4-fluorophenyl)-2,3,4,5-tetrahydro-1H-1-benzazepine TLC:Rf 0.33 (n-hexane:ethyl acetate=2:1);
NMR (CDCl$_3$):δ 7.20-7.01 (m, 4H), 6.97 (dd, J=9.0 Hz, 3.0 Hz, 1H), 6.90-6.78 (m, 1H), 6.64-6.48 (m, 1H), 4.68-4.50 (m, 1H), 4.33-4.24 (m, 1H), 4.14-4.06 (m, 1H), 3.34-3.18 (m, 2H), 2.85-2.67 (m, 1H), 2.20-1.96 (m, 2H), 1.96-1.70 (m, 2H), 1.14-1.00 (m, 3H).

EXAMPLE 7(5)

8-fluoro-1-phenylcarbamoyl-2,3,4,5-tetrahydro-1H-1-benzazepine

TLC:Rf 0.33 (n-hexane:ethyl acetate=4:1);
NMR (CDCl$_3$):δ 7.34-7.21 (m, 5H), 7.08-6.96 (m, 3H), 6.17 (bs, 1H), 4.45-4.90 (b, 1H), 2.84-2.72 (m, 3H), 2.04-1.20 (m, 4H).

EXAMPLE 7(6)

8-methoxymethyloxy-1-phenylcarbamoyl-2,3,4,5-tetrahydro-1H-1-benzazepine

TLC:Rf 0.39 (n-hexane:ethyl acetate=3:1);
NMR (CDCl$_3$):δ 7.33-7.19 (m, 5H), 7.02-6.94 (m, 3H), 6.30 (bs, 1H), 5.16 (s, 2H), 4.75-4.55 (m, 1H), 3.49 (s, 3H), 2.85-2.62 (m, 3H), 2.08-1.75 (m, 3H), 1.50-1.20 (m, 1H).

EXAMPLE 7(7)

6-methoxy-1-phenylcarbamoyl-2,3,4,5-tetrahydro-1H-1-benzazepine

TLC:Rf 0.44 (n-hexane:ethyl acetate=3:1);
NMR (CDCl$_3$):δ 7.32-7.19 (m, 5H), 7.01-6.87 (m, 3H), 6.32-6.25 (bs, 1H), 4.71-4.58 (m, 1H), 3.87 (s, 3H), 3.45-3.31 (m, 1H), 2.78-2.63 (m, 1H), 2.42-2.28 (m, 1H), 2.06-1.90 (m, 2H), 1.85-1.72 (m, 1H), 1.40-1.19 (m, 1H).

EXAMPLE 7(8)

7-methoxy-1-phenylcarbamoyl-2,3,4,5-tetrahydro-1H-1-benzazepine

TLC:Rf 0.35 (n-hexane:ethyl acetate=3:1);
NMR (CDCl$_3$):δ 7.32-7.18 (m, 5H), 7.00-6.94 (m, 1H), 6.84 (d, J=2.7 Hz, 1H), 6.79 (dd, J=8.4 Hz, 2.7 Hz, 1H), 6.25 (bs, 1H), 4.72-4.58 (m, 1H), 3.84 (s, 1H), 2.90-2.77 (m, 1H), 2.72-2.58 (m, 2H), 2.08-1.88 (m, 2H), 1.86-1.74 (m, 1H), 1.46-1.28 (m, 1H).

EXAMPLE 7(9)

1-(4-methoxyphenylcarbamoyl)-2,3,4,5-tetrahydro-1H-1-benzazepine

TLC:Rf 0.44 (n-hexane:ethyl acetate=2:1);
NMR (CDCl$_3$):δ 7.34-7.25 (m, 4H), 7.23-7.16 (m, 2H), 6.82-6.75 (m, 2H), 6.07 (bs, 1H), 4.80-4.54 (m, 1H), 3.76 (s, 3H), 3.00-2.54 (m, 3H), 2.13-1.71 (m, 3H), 1.53-1.20 (m, 1H).

EXAMPLE 7(10)

1-phenylcarbamoyl-1,2,3,4,5,6-hexahydro-1-benzazocine

TLC:Rf 0.38 (n-hexane:ethyl acetate=5:1);
NMR (CDCl$_3$):δ 7.42-7.30 (m, 3H), 7.28-7.18 (m, 5H), 7.00-6.93 (m, 1H), 5.94 (brs, 1H), 4.76-4.65 (m, 1H), 2.97-2.88 (m, 1H), 2.85-2.72 (m, 1H), 2.69-2.58 (m, 1H), 1.98-1.84 (m, 1H), 1.82-1.68 (m, 1H), 1.67-1.29 (m, 4H).

EXAMPLE 7(11)

1-(4-fluorophenylcarbamoyl)-2,3,4,5-tetrahydro-1H-1-benzazepine

TLC:Rf 0.44 (n-hexane:ethyl acetate=3:1);
NMR (CDCl$_3$):δ 7.35-7.20 (m, 6H), 6.96-6.89 (m, 2H), 6.16 (brs, 1H), 4.76-4.61 (m, 1H), 2.89-2.59 (m, 3H), 2.09-1.72 (m, 3H), 1.45-1.30 (m, 1H).

EXAMPLE 7(12)

1-benzylcarbamoyl-2,3,4,5-tetrahydro-1H-1-benzazepine

TLC:Rf 0.36 (n-hexane:ethyl acetate=3:1);
NMR (CDCl$_3$):δ 7.33-7.18 (m, 10H), 4.65-4.56 (m, 1H), 4.44-4.35 (m, 3H), 2.82-2.45 (m, 3H), 2.04-1.72 (m, 3H), 1.49-1.19 (m, 1H).

EXAMPLE 7(13)

1-(2-chlorophenylcarbamoyl)-2,3,4,5-tetrahydro-1H-1-benzazepine

TLC:Rf 0.54 (n-hexane:ethyl acetate=3:1);
NMR (CDCl$_3$):δ 8.34-8.29 (m, 1H), 7.38-7.19 (m, 6H), 6.93 (brs, 1H), 6.92-6.86 (m, 1H), 4.70-4.59 (m, 1H), 2.96-2.65 (m, 3H), 2.12-1.78 (m, 3H), 1.52-1.28 (m, 1H).

EXAMPLE 7(14)

1-(3-chlorophenylcarbamoyl)-2,3,4,5-tetrahydro-1H-1-benzazepine

TLC:Rf 0.48 (n-hexane:ethyl acetate=3:1);
NMR (CDCl$_3$):δ 7.42-7.40 (m, 1H), 7.34-7.27 (m, 4H), 7.15-7.12 (m, 2H), 6.97-6.93 (m, 1H), 6.23 (brs, 1H), 4.76-4.59 (m, 1H), 2.90-2.61 (m, 3H), 2.09-1.77 (m, 3H), 1.51-1.23 (m, 1H).

EXAMPLE 7(15)

1-(4-chlorophenylcarbamoyl)-2,3,4,5-tetrahydro-1H-1-benzazepine

TLC:Rf 0.44 (n-hexane:ethyl acetate=3:1);
NMR (CDCl$_3$):δ 7.38-7.15 (m, 8H), 6.21 (brs, 1H), 4.78-4.60 (m, 1H), 2.90-2.59 (m, 3H), 2.08-1.78 (m, 3H), 1.48-1.25 (m, 1H).

EXAMPLE 7(16)

1-(2,3-dichlorophenylcarbamoyl)-2,3,4,5-tetrahydro-1H-1-benzazepine

TLC:Rf 0.52 (n-hexane:ethyl acetate=3:1);
NMR (CDCl$_3$):δ 8.29 (dd, J=8.1 Hz, 1.5 Hz, 1H), 7.39-7.29 (m, 4H), 7.16 (t, J=8.1 Hz, 1H), 7.06 (dd, J=8.1 Hz, 1.5 Hz, 1H), 7.03 (brs,1H), 4.71-4.60 (m, 1H) 2.93-2.68 (m, 3H), 2.10-1.69 (m, 3H) 1.53-1.30 (m, 1H).

EXAMPLE 7(17)

1-(2,4-dichlorophenylcarbamoyl)-2,3,4,5-tetrahydro-1H-1-benzazepine

TLC:Rf 0.56 (n-hexane:ethyl acetate=3:1);
NMR (CDCl$_3$):δ 8.29 (d, J=8.7 Hz, 1H), 7.36-7.17 (m, 6H), 6.86 (brs, 1H), 4.70-4.59 (m, 1H), 2.93-2.66 (m, 3H), 2.10-1.78 (m, 3H) 1.53-1.29 (m, 1H).

EXAMPLE 7(18)

1-(2,6-dichlorophenylcarbamoyl)-2,3,4,5-tetrahydro-1H-1-benzazepine

TLC:Rf 0.32 (n-hexane:ethyl acetate=3:1);
NMR (CDCl$_3$):δ 7.48-7.44 (m, 1H), 7.36-7.24 (m, 5H) 7.08 (dd, J=8.7 Hz, 7.5 Hz, 1H), 5.93 (brs, 1H), 4.70-4.59 (m, 1H), 3.09-2.93 (m, 1H), 2.86-2.64 (m, 2H), 2.12-1.93 (m, 2H), 1.88-1.72 (m, 1H), 1.55-1.30 (m, 1H).

EXAMPLE 7(19) cl 1-(2,5-dichlorophenylcarbamoyl)-2,3,4,5-tetrahydro-1H-1 benzazepine TLC:Rf 0.62 (n-hexane:ethyl acetate=3:1);
NMR (CDCl$_3$):δ 8.46 (d, J=2.7 Hz, 1H), 7.36-7.28 (m, 4H) 7.12 (d, J=8.7 H 1H), 6.96 (brs, 1H), 6.87 (dd, J=8.7 Hz, 2.7 Hz, 1H), 4.70-4.59 (m, 1H), 2.93-2.66 (m, 3H), 2.11-1.77 (m, 3H), 1.53-1.29 (m, 1H).

EXAMPLE 7(20)

1-(3,4-dichlorophenylcarbamoyl)-2,3,4,5-tetrahydro-1H-1-benzazepine

TLC:Rf 0.48 (n-hexane:ethyl acetate=3:1);
NMR (CDCl$_3$):δ 7.53 (d, J=2.4 Hz, 1H), 7.36-7.24 (m, 5H), 7.13 (dd, J=8.7 Hz, 2.4 Hz, 1H), 6.21 (brs, 1H), 4.72-4.59 (m, 1H), 2.90-2.61 (m, 3H), 2.08-1.77 (m, 3H), 1.53-1.25 (m, 1H).

EXAMPLE 7(21)

1-(3,5-dichlorophenylcarbamoyl)-2,3,4,5-tetrahydro-1H-1-benzazepine

TLC:Rf 0.58 (n-hexane:ethyl acetate=3:1);
NMR (CDCl$_3$):δ 7.35-7.25 (m, 6H), 6.96 (t, J=1.8 Hz, 1H), 6.25 (brs, 1H), 4.69-4.59 (m, 1H), 2.87-2.62 (m, 3H), 2.08-1.76 (m, 3H), 1.50-1.28 (m, 1H).

EXAMPLE 7(22)

1-cyclohexylcarbamoyl-2,3,4,5-tetrahydro-1H-1-benzazepine

TLC:Rf 0.34 (n-hexane:ethyl acetate=3:1);
NMR (CDCl$_3$):δ 7.29-7.15 (m, 4H), 4.79-4.37 (m, 1H), 4.11-4.01 (m, 1H), 3.70-3.55 (m, 1H), 2.81-2.40 (m, 3H), 2.05-1.67 (m, 4H), 1.64-1.48 (m, 4H), 1.39-1.22 (m, 3H), 1.16-0.84 (m, 3H).

EXAMPLE 7(23)

1-(4-nitrophenylcarbamoyl)-2,3,4,5-tetrahydro-1H-1-benzazepine

TLC:Rf 0.33 (n-hexane:ethyl acetate=1:1);
NMR (CDCl$_3$):δ 8.15-8.09 (m, 2H), 7.49-7.43 (m, 2H), 7.38-7.28 (m, 4H), 6.59 (brs, 1H), 4.73-4.61 (m, 1H), 2.89-2.68 (m, 3H), 2.10-1.79 (m, 3H), 1.50-1.29 (m, 1H).

EXAMPLE 7(24)

1-(4-cyanophenylcarbamoyl)-2,3,4,5-tetrahydro-1H-1-benzazepine

TLC:Rf 0.22 (n-hexane:ethyl acetate=1:1);
NMR (CDCl$_3$):δ 7.54-7.48 (m, 2H), 7.45-7.39 (m, 2H), 7.37-7.25 (m, 4H), 6.44 (brs, 1H), 4.72-4.61 (m, 1H); 2.90-2.63 (m, 3H), 2.10-1.78 (m, 3H), 1.52-1.25 (m, 1H).

EXAMPLE 7(25)

1-(4-methylphenylcarbamoyl)-2,3,4,5-tetrahydro-1H-1-benzazepine

TLC:Rf 0.42 (n-hexane:ethyl acetate=1:1);
NMR (CDCl$_3$):δ 7.35-7.25 (m, 4H), 7.20-7.14 (m, 2H), 7.06-7.00 (m, 2H), 6.13 (brs, 1H), 4.80-4.58 (m, 1H), 2.94-2.58 (m, 3H), 2.26 (s, 3H), 2.10-1.71 (m, 3H), 1.51-1.22 (m, 1H).

EXAMPLE 7(26)

1-cyclopentylcarbamoyl-2,3,4,5-tetrahydro-1H-1-benzazepine

TLC:Rf 0.39 (n-hexane:ethyl acetate=3:1);
NMR (CDCl$_3$):δ 7.29-7.14 (m, 4H), 4.74-4.31 (m, 1H), 4.19-4.05 (m, 2H), 2.81-2.32 (m, 3H), 2.08-1.66 (m, 5H), 1.59-1.03 (m, 7H).

EXAMPLE 7(27)

1-isopropylcarbamoyl-2,3,4,5-tetrahydro-1H-1-benzazepine

TLC:Rf 0.35 (n-hexane:ethyl acetate=3:1);
NMR (CDCl$_3$):δ 7.29-7.15 (m, 4H), 4.84-4.23 (m, 1H), 4.04-3.90 (m, 2H), 2.81-2.25 (m, 3H), 2.05-1.64 (m, 3H), 1.58-1.13 (m, 1H), 1.03 (d, J=6.0 Hz, 6H).

EXAMPLE 7(28)

1-hexylcarbamoyl-2,3,4,5-tetrahydro-1H-1-benzazepine

TLC:Rf 0.44 (n-hexane:ethyl acetate=3:1);
NMR (CDCl$_3$):δ 7.29-7.16 (m, 4H), 4.78-4.39 (m, 1H), 4.26-4.13 (m, 1H), 3.24-3.03 (m, 2H), 2.82-2.43 (m, 3H), 2.06-1.69 (m, 3H), 1.45-1.14 (m, 9H), 0.85 (t, J=6.9 Hz, 3H).

EXAMPLE 7(29)

4-phenylcarbamoyl-5,6,7,8-tetrahydro-4H-thieno[2,3-f]-4-azepine

TLC:Rf 0.38 (n-hexane:ethyl acetate=5:1);
NMR (CDCl$_3$):δ 7.36-7.31 (m, 2H), 7.30-7.21 (m, 2H), 7.08 (d, J=5.4 Hz, 1H), 7.04-6.95 (m, 2H), 6.51 (bs, 1H), 4.0-3.4 (b, 2H), 2.89-2.82 (m, 2H), 1.98-1.90 (m, 2H), 1.78-1.62 (m, 2H)

EXAMPLE 7(30)

8-nitro-1-phenylcarbamoyl-2,3,4,5-tetrahydro-1H-1-benzazepine

TLC:Rf 0.45 (ethyl acetate: n-hexane=2:3);
NMR (DMSO-d6):δ 8.14 (bs, 1H), 8.10 (dd, J=8.4 Hz, 2.1 Hz, 1H), 8.02 (d, J=2.1 Hz, 1H), 7.63 (d, J=8.4 Hz, 1H), 7.44-7.38 (m, 2H), 7.26-7.18 (m, 2H), 7.00-6.93 (m, 1H), 3.83-3.44 (m, 2H), 2.90-2.83 (m, 2H), 1.90-1.53 (m, 4H).

EXAMPLE 7(31)

8-methyl-1-phenylcarbamoyl-2,3,4,5-tetrahydro-1H-1-benzazepine

TLC:Rf 0.43 (n-hexane:ethyl acetate=4:1);
NMR (CDCl$_3$):δ 7.32-7.19 (m, 5H), 7.11-7.08 (m, 2H), 7.01-6.95 (m, 1H), 6.23 (s, 1H), 4.76-4.59 (br, 1H), 2.87-2.57 (br, 3H), 2.35 (s, 3H), 2.08-1.72 (m, 3H), 1.45-1.22 (br, 1H).

EXAMPLE 7(32)

1-(4-bromophenylcarbamoyl)-2,3,4,5-tetrahydro-1H-1-benzazepine

NMR (CDCl$_3$):δ 7.36-7.24 (m, 6H), 7.24-7.17 (m, 2H), 6.21 (brs, 1H), 4.75-4.53 (m, 1H), 2.95-2.53 (m, 3H), 2.15-1.73 (m, 3H), 1.50-1.20 (m, 1H).

EXAMPLE 7(33)

7-benzyloxy-1-phenylcarbamoyl-2,3,4,5-tetrahydro-1H-1-benzazepine

TLC:Rf 0.39 (n-hexane:ethyl acetate=3:1);
NMR (CDCl$_3$):δ 7.49-7.18 (m, 10H), 7.01-6.92 (m, 2H), 6.86 (dd, J=8.7 Hz, 3.0 Hz, 1H), 6.25 (s, 1H), 5.09 (s, 2H), 4.71-4.61 (m, 1H), 2.90-2.59 (m, 3H), 2.08-1.74 (m, 3H), 1.46-1.30 (m, 1H).

EXAMPLE 7(34)

7-benzyloxy-1-(4-fluorophenylcarbamoyl)-2,3,4,5-tetrahydro-1H-1-benzazepine

TLC:Rf 0.36 (n-hexane:ethyl acetate=3:1);
NMR (CDCl$_3$):δ 7.49-7.32 (m, 5H), 7.27-7.21 (m, 3H), 6.97-6.83 (m, 4H), 6.20 (brs, $_1$H), 5.07 (s, 2H), 4.69-4.58 (m, 1H), 2.85-2.60 (m, 3H), 2.06-1.76 (m, 3H), 1.59-1.22 (m, 1H).

EXAMPLE 7(35)

7-chloro-1-phenylcarbamoyl-2,3,4,5-tetrahydro-1H-1-benzazepine

TLC:Rf 0.23 (n-hexane:ethyl acetate=3:1);
NMR (CDCl$_3$):δ 7.34-7.22 (m, 7H), 7.04-6.98 (m,1H), 6.17-6.10 (m, 1H), 4.85-4.42 (m, 1H), 2.90-2.52 (m, 3H), 2.06-1.73 (m, 3H), 1.59-1.22 (m, 1H).

EXAMPLE 8

8-fluoro-5-(4-fluorophenyl)-1-(N-methyl-N-phenylaminocarbonyl)-2,3,4,5-tetrahydro-1H-1-benzazepine A mixture of which N,N-dimethylformamide (2.5 ml) solution of the compound (271 mg) prepared in Example 7 and tetrahydrofuran (1 ml) have been added to N,N-dimethylformamide (0.5 ml) suspension of sodium hydride (29 mg) during storage in ice was stirred for 1 hour under argon gas. In addition, the reactive mixture to which methyl iodide (45 μl) was added was stirred for 2 hours. The reactive mixture to which water is added was extracted by ethyl acetate. The organic layer sequentially washed with saturated sodium bicarbonate solution, water, and saturated brine was concentrated after drying with sulfuric anhydride magnesium. The obtained residue was purified by silica gel column chromatography (n-hexane:ethyl acetate=93:7), and was recrystallized from n-hexane ethyl acetate. The present compound (149 mg) having the following physical properties values was obtained.

TLC:Rf 0.43 (toluene:ethyl acetate=9:1);
NMR (CDCl$_3$):δ 7.22-7.14 (m, 2H), 7.12-7.06 (m, 1H), 7.03-6.94 (m, 2H), 6.91-6.82 (m, 5H), 6.50 (td, J=8.4 Hz, 2.4 Hz, 1H), 6.02 (dd, J=8.4 Hz, 6.6 Hz, 1H), 4.63 (dt, J=13.8, 4.8 Hz, 1H), 3.54-3.46 (m, 1H), 3.20 (s, 3H), 2.85 (ddd, J=13.8 Hz, 9.6 Hz, 3.0 Hz, 1H), 2.05-1.95 (m,1H), 1.92-1.72 (m, 2H), 1.69-1.52 (m, 1H).

EXAMPLE 9

1-carbamoyl-8-fluoro-5-(4-fluorophenyl)-2,3,4,5-tetrahydro-1H-benzazepine

A mixture of which sodium cyanate (65 mg) have been added to acetonitrile (1.5 ml) solution of the compound (130 mg) prepared in Reference example 12 was refluxed over night. The reactive mixture to which water is added was extracted by ethyl acetate. The organic layer sequentially washed with saturated sodium bicarbonate solution, water, and saturated brine was concentrated after drying with sulfuric anhydride magnesium. The obtained residue was recrystallized from n-hexane ethyl acetate. The present compound (99 mg) having the following physical properties values was obtained.

TLC:Rf 0.48 (n-hexane:ethyl acetate=1:3);
NMR (CDCl$_3$):δ 7.24-7.01 (m, 5H), 6.88-6.78 (m, 1H), 6.60-6.50 (m, 1H), 4.62-4.40 (m, 3H), 4.20-4.10 (m, 1H), 2.86-2.72 (m, 1H), 2.24-2.04 (m, 2H), 1.94-1.74 (m, 2H).

EXAMPLE 10

1-(N,N-dimethylcarbamoyl)-8-fluoro-5-(4-fluorophenyl)-2,3,4,5-tetrahydro-1H-1-benzazepine A mixture of which dimethylcarbamoyl chloride (55 μl) have been added to pyridine (3 ml) solution of the compound (148 mg) prepared in Reference example 12 was refluxed for 4 hours. In addition, dimethylcarbamoyl chloride (55 μl) was added, and was refluxed for a day. The reactive mixture to which water is added was extracted by ethyl acetate. The organic layer sequentially washed with saturated sodium bicarbonate solution, water, and saturated brine was concentrated after drying with sulfuric anhydride magnesium. The obtained residue was purified by silica gel column chromatography (n-hexane:ethyl acetate=3:1 to 2:1), and was recrystallized from n-hexane ethyl acetate. The present compound (83 mg) having the following physical properties values was obtained.

TLC:Rf 0.35 (n-hexane:ethyl acetate=2:1);
NMR (CDCl$_3$):δ 7.20-7.13 (m, 2H), 7.11-7.03 (m, 2H), 6.73-6.65 (m, 2H), 6.54-6.47 (m, 1H), 4.47-4.32 (m, 1H), 4.23-4.18 (m, 1H), 3.04-2.92 (m, 1H), 2.69 (s, 6H), 2.20-2.11 (m, 1H), 1.93-1.76 (m, 3H).

EXAMPLE 11

1-phenylaminothiocarbonyl-2,3,4,5-tetrahydro-1H-1-benzazepine

The present compound having the following physical properties values was obtained by operating as well as the method represented in Example 1, using phenylthio isocyanate instead of phenyl isocyanate.

TLC:Rf 0.50 (n-hexane:ethyl acetate=3:1);
NMR (CDCl$_3$):δ 7.40-7.28 (m, 8H), 7.22-7.15 (m, 1H), 6.96 (brs, 1H), 5.58-5.40 (m, 1H), 3.09-2.97 (m, 1H), 2.92-2.70 (m, 2H), 2.44-2.26 (m, 1H), 2.11-1.98 (m, 1H), 1.87-1.77 (m, 1H), 1.55-1.36 (m, 1H).

EXAMPLE 12

1-(2-cyclohexylethylcarbamoyl)-2,3,4,5-tetrahydro-1H-1-benzazepine

A mixture of which diphenylphosphorylazide(0.17 ml) and triethylamine (0.11 ml) are added to toluene (3 ml) solution of 3-cyclohexyl propionate (120 mg) at room temperature was refluxed for 90 minutes at 120° C. In addition, the reactive mixture to which toluene (3 ml) solution of 2,3,4,5-1H-tetrahydro benzazepine (114 mg) had been added was refluxed for 3 hours at 120° C. In addition, the reactive mixture cooled up to room temperature was concentrated. The obtained residue was purified by silica gel column chromatography (n-hexane: ethyl acetate=6:1). The present compound (196 mg) having the following physical properties values was obtained.

TLC:Rf 0.42 (n-hexane:ethyl acetate=3:1);
NMR (CDCl$_3$):δ 7.30-7.17 (m, 4H), 4.78-4.36 (m, 1H), 4.22-4.13 (m, 1H), 3.28-3.08 (m, 2H), 2.83-2.41 (m, 3H), 2.03-0.79 (m, 17H).

EXAMPLE 12(1)-EXAMPLE 12(23)

Compounds of the present invention having the following physical properties values were obtained by operating as well as the method represented in Example 12, using the corresponding compound.

EXAMPLE 12(1)

1-(1,3-benzodioxol-5-ylcalbamoyl)-2,3,4,5-tetrahydro-1H-1-benzazepine

TLC:Rf 0.31 (n-hexane:ethyl acetate=3:1);
NMR (CDCl$_3$):δ 7.36-7.25 (m, 4H), 7.09 (d, J=2.1 Hz, 1H), 6.65 (d, J=8.1 Hz, 1H), 6.49 (dd, J=8.1 Hz, 2.1 Hz, 1H) 6.09 (brs, 1H), 5.90 (s, 2H), 4.78-4.51 (m, 1H), 2.89-2.57 (m, 3H), 2.08-1.69 (m, 3H), 1.50-1.22 (m, 1H).

EXAMPLE 12(2)

1-(4-benzyloxyphenylcarbamoyl)-2,3,4,5-tetrahydro-1H-1-benzazepine

TLC:Rf 0.56 (n-hexane:ethyl acetate=2:1);
NMR (CDCl$_3$):δ 7.43-7.24 (m, 9H), 7.22-7.16 (m, 2H), 6.89-6.83 (m, 2H), 6.08 (bs, 1H), 5.01 (s, 2H), 4.80-4.73 (b, 1H), 2.95-2.53 (m, 3H), 2.13-2.07 (m, 3H), 1.48-1.20 (m, 1H).

EXAMPLE 12(3)

1-(3-chloro-4-methoxymethyloxyphenylcarbamoyl)-2,3,4,5-tetrahydro-1H-1-benzazepine TLC:Rf 0.53 (n-hexane:ethyl acetate=2:1);
NMR (CDCl$_3$):δ 7.41 (d, J=2.7 Hz, 1H), 7.35-7.26 (m, 4H), 7.10 (dd, J=9.0 Hz, 2.7 Hz, 1H), 7.03 (d, J=9.0 Hz, 1 Hz), 6.10 (brs, 1H), 5.16 (s, 2H), 4.75-4.57 (m, 1H), 3.49 (s, 3H), 2.91-2.57 (m, 3H), 2.07-1.72 (m, 3H), 1.57-1.23 (m, 1H).

EXAMPLE 12(4)

1-(2-chloro-4-methoxymethyloxyphenylcarbamoyl)-2,3,4,5-tetrahydro-1H-1-benzazepine TLC:Rf 0.57 (n-hexane:ethyl acetate=2:1);
NMR (CDCl$_3$):δ 8.12 (d, J=9.0 Hz, 1H), 7.38-7.26 (m, 4H), 6.97 (d, J=2.7 Hz, 1H), 6.93 (dd, J=9.0 Hz, 2.7 Hz, 1H), 6.67 (brs, 1H), 5.08 (s, 2H), 4.71-4.58 (m, 1H), 3.44 (s, 3H), 2.94-2.63 (m, 3H), 2.09-1.76 (m, 3H), 1.51-1.27 (m, 1H).

EXAMPLE 12(5)

1-(4-methoxymethyloxy-3-nitrophenylcarbamoyl)-2,3,4,5-tetrahydro-1H-1-benzazepine TLC:Rf 0.32 (n-hexane:ethyl acetate=2:1);
NMR (CDCl$_3$):δ 7.79 (d, J=2.7 Hz, 1H), 7.49 (dd, J=9.0 Hz, 2.7 Hz, 1H), 7.37-7.27 (m, 4H), 7.17 (d, J=9.0 Hz, 1H), 6.32 (brs, 1H), 5.20 (s, 2H), 4.72-4.57 (m, 1H), 3.49 (s, 3H), 2.90-2.58 (m, 3H), 2.09-1.76 (m, 3H), 1.50-1.23 (m, 1H).

EXAMPLE 12(6)

1-(4-benzyloxyphenylcarbamoyl)-8-chloro-2,3,4,5-tetrahydro-1H-1-benzazepine

TLC:Rf 0.32 (n-hexane:ethyl acetate=3:1);
NMR (CDCl$_3$):δ 7.43-7.25 (m, 8H), 7.24-7.17 (m, 2H), 6.90-6.83 (m, 2H), 6.01 (brs, 1H), 5.01 (s, 2H), 4.82-4.42 (m, 1H), 2.85-2.41 (m, 3H), 2.02-1.71 (m, 3H), 1.58-1.30 (m, 1H).

EXAMPLE 12(7)

4-(4-benzyloxyphenylcarbamoyl)-5, 6, 7, 8-tetrahydro4H -thieno[2,3-f]azepine

TLC:Rf 0.56 (n-hexane:ethyl acetate=2:1);
NMR (CDCl$_3$):δ 7.44-7.20 (m, 7H), 7.06 (d, J=5.4 Hz, 1H), 6.96 (d, J=5.4 Hz, 1H), 6.92-6.86 (m, 2H), 6.38 (s, 1H), 5.02 (s, 2H), 4.0-3.3 (b, 2H), 2.88-2.80 (m, 2H), 1.98-1.88 (m, 2H), 1.78-1.60 (m, 2H).

EXAMPLE 12(8)

1-(2-methoxy-4-methoxymethyloxyphenylcarbamoyl)-2,3,4,5-tetrahydro-1H-1-benzazepine TLC:Rf 0.34 (n-hexane:ethyl acetate=2:1);
NMR (CDCl$_3$):δ 8.06 (d, J=9.3 Hz, 1H), 7.34-7.24 (m, 4H), 6.73 (bs,1H), 6.62 (dd, J=9.3 Hz, 2.7 Hz, 1H), 6.48 (d, J=2.7 Hz, 1H), 5.10 (s, 2H), 4.8-4.5 (m, 1H), 3.59 (s, 3H), 3.46 (s, 3H), 2.9-2.6 (m, 3H), 2.1-1.7 (m, 3H), 1.6-1.2 (m, 1H).

EXAMPLE 12(9)

1-(4-benzyloxyphenylcarbamoyl)-7-methoxy-2,3,4,5-tetrahydro-1H-1-benzazepine

TLC:Rf 0.21 (n-hexane:ethyl acetate=3:1);
NMR (CDCl$_3$):δ 7.43-7.29 (m, 4H), 7.23-7.17 (m, 3H), 6.89-6.75 (m, 4H), 6.10 (brs, 1H), 5.01 (s, 2H), 4.71-4.57 (m, 1H), 3.84 (s, 3H), 2.90-2.57 (m, 3H), 2.06-1.69 (m, 3H), 1.48-1.27 (m, 1H).

EXAMPLE 12(10)

1-(4-benzyloxyphenylcarbamoyl)-8-methoxy-2,3,4,5-tetrahydro-1H-1-benzazepine

TLC:Rf 0.22 (n-hexane:ethyl acetate=3:1):

NMR (CDCl$_3$):δ 7.43-7.29 (m, 5H), 7.24-7.17 (m, 3H), 6.90-6.79 (m, 4H), 6.15 (brs, 1H), 5.01 (s, 2H), 4.79-4.52 (m, 1H), 3.80 (s, 3H), 2.84-2.52 (m, 3H), 2.09-1.63 (m, 3H), 1.51-1.18 (m, 1H).

EXAMPLE 12(11)

1-(4-benzyloxyphenylcarbamoyl)-6-methoxy-2,3,4,5-tetrahydro-1H-1-benzazepine

TLC:Rf 0.21 (n-hexane:ethyl acetate=3:1);

NMR (CDCl$_3$):δ 7.43-7.28 (m, 5H), 7.24-7.16 (m, 3H), 6.93-6.88 (m, 4H), 6.15 (brs, 1H), 5.01 (s, 2H), 4.71-4.57 (m, 1H), 3.86 (s, 3H), 3.45-3.31 (m, 1H), 2.78-2.59 (m, 1H), 2.46-2.26 (m, 1H), 2.11-1.68 (m, 3H), 1.41-1.14 (m, 1H).

EXAMPLE 12(12)

1-(3-fluoro-4-methoxymethyloxyphenylcarbamoyl)-2,3,4,5-tetrahydro-1H-1-benzazepine TLC:Rf 0.40 (n-hexane:ethyl acetate=2:1);

NMR (CDCl$_3$):δ 7.37-7.26 (m, 5H), 7.02 (t, J=9.0 Hz, 1H), 6.78 (ddd, J=9.0 Hz, 2.4 Hz, 1.5 Hz, 1H), 6.14 (bs, 1H), 5.12 (s, 2H), 4.8-4.6 (m, 1H), 3.49 (s, 3H), 2.9-2.6 (m, 3H), 2.1-1.7 (m, 3H), 1.6-1.2 (m, 1H).

EXAMPLE 12(13)

8-benzyloxy-1-(4-benzyloxyphenylcarbamoyl)-2,3,4,5-tetrahydro-1H-1-benzazepine

TLC:Rf 0.28 (n-hexane:ethyl acetate=3:1);

NMR (CDCl$_3$):δ 7.44-7.27 (m, 10H), 7.23-7.10 (m, 3H), 6.92-6.82 (m, 4H), 6.07 (brs, 1H), 5.06 (s, 2H), 5.02 (s, 2H), 4.78-4.53 (m, 1H), 2.82-2.51 (m, 3H), 2.07-1.69 (m, 3H), 1.50-1.18 (m, 1H).

EXAMPLE 12(14)

1-(4-methoxymethyloxyphenylcarbamoyl)-8-nitro-2,3,4,5-tetrahydro-1H-1-benzazepine TLC:Rf 0.34 (n-hexane:ethyl acetate=3:2);

NMR (CD$_3$OD):δ 8.14-8.09 (m, 2H), 7.58-7.53 (m, 1H), 7.24-7.18 (m, 2H), 6.96-6.90 (m, 2H), 5.12 (s, 2H), 4.2-3.5 (m, 2H), 3.42 (s, 3H), 2.96-2.89 (m, 2H), 1.93-1.65 (m, 4H).

EXAMPLE 12(15)

1-cyclohexylmethylcarbamoyl-2,3,4,5-tetrahydro-1H-1-benzazepine

TLC:Rf 0.38 (n-hexane:ethyl acetate=3:1);

NMR (CDCl$_3$):δ 7.31-7.18 (m, 4H), 4.78-4.37 (m, 1H), 4.36-4.22 (m, 1H), 3.15-2.82 (m, 2H), 2.79-2.37 (m, 3H), 2.05-1.54 (m, 6H), 1.47-0.74 (m, 9H).

EXAMPLE 12(16)

1-(3-benzyloxyphenylcarbamoyl)-2,3,4,5-tetrahydro-1H-1-benzazepine

TLC:Rf 0.50 (n-hexane:ethyl acetate=3:1);

NMR (CDCl$_3$):δ 7.45-7.24 (m, 10H), 7.10 (t, J=8.1 Hz, 1H), 6.71 (dd, J=8.1 Hz, 2.4 Hz, 1H), 6.61 (dd, J=8.1 Hz, 2.4 Hz, 1H), 6.23 (brs, 1H), 5.03 (s, 2H), 4.77-4.59 (m, 1H), 2.91-2.57 (m, 3H), 2.10-1.67 (m, 3H), 1.59-1.27 (m, 1H).

EXAMPLE 12(17)

1-(4-benzyloxy-3-methoxyphenylcarbamoyl)-2,3,4,5-tetrahydro-1H-1-benzazepine

TLC:Rf 0.22 (n-hexane:ethyl acetate=3:1);

NMR (CDCl$_3$):δ 7.47-7.25 (m, 10H), 6.70 (d, J=8.7 Hz, 1H), 6.40 (dd, J=8.7 Hz, 2.4 Hz, 1H), 6.10 (brs, 1H), 5.09 (s, 2H), 4.78-4.57 (m, 1H), 3.88 (s, 3H), 2.91-2.56 (m, 3H), 2.11-1.77 (m, 3H), 1.61-1.25 (m, 1H).

EXAMPLE 12(18)

1-(4-benzyloxy-3-nitrophenylcarbamoyl)-2,3,4,5-tetrahydro-1H-1-benzazepine

TLC:Rf 0.22 (n-hexane:ethyl acetate=3:1);

NMR (CDCl$_3$):δ 7.72 (d, J=2.7 Hz, 1H), 7.59 (dd, J=9.0 Hz 2.7 Hz, 1H), 7.46-7.22 (m, 9H), 7.00 (d, J=9.0 Hz, 1H), 6.21 (brs, 1H), 5.18 (s, 1H), 4.72-4.57 (m, 1H), 2.88-2.60 (m, 3H), 2.09-1.73 (m, 3H), 1.51-1.23 (m, 1H).

EXAMPLE 12(19)

1-(4-benzyloxy-3-chlorophenylcarbamoyl)-2,3,4,5-tetrahydro-1H-1-benzazepine

TLC:Rf 0.35 (n-hexane:ethyl acetate=3:1);

NMR (CDCl$_3$):δ 7.46-7.25 (m, 10H), 7.12 (dd, J=8.7 Hz, 2.7 Hz, 1H), 6.83 (d, J=8.7 Hz, 1H), 6.09 (brs, 1H), 5.09 (s, 2H), 4.75-4.52 (m, 1H), 2.87-2.59 (m, 3H), 2.05-1.68 (m, 3H), 1.51-1.29 (m, 1H).

EXAMPLE 12(20)

1-(4-benzyloxy-2-chlorophenylcarbamoyl)-2,3,4,5-tetrahydro-1H-1-benzazepine

TLC:Rf 0.50 (n-hexane:ethyl acetate=3:1);

NMR (CDCl$_3$):δ 8.11-8.07 (m, 1H), 7.44-7.24 (m, 9H), 6.90-6.84 (m, 2H), 6.61 (brs, 1H), 4.99 (s, 2H), 4.72-4.58 (m, 1H), 2.95-2.62 (m, 3H), 2.10-1.72 (m, 3H), 1.51-1.25 (m, 1H).

EXAMPLE 12(21)

1-(4-benzyloxyphenylcarbamoyl)-8-fluoro-5-(4-fluorophenyl)-2,3,4,5-tetrahydro-1H-1-benzazepine TLC:Rf 0.17 (n-hexane:ethyl acetate=5:1);

NMR (CDCl$_3$):δ 7.44-7.02 (m, 13H), 6.96-6.82 (m, 3H), 6.68-6.44 (m, 1H), 6.13 (bs, 1H), 5.04 (s, 2H), 4.70-4.55 (m, 1H), 4.26-4.06 (m, 1H), 2.93-2.70 (m, 1H), 2.27-1.73 (m, 4H).

EXAMPLE 12(22)

1-(4-benzyloxyphenylcarbamoyl)-1,2,3,4,5,6-hexahydro-1-benzazocine

TLC:Rf 0.32 (n-hexane:ethyl acetate=3:1);
NMR (CDCl$_3$):δ 7.45-7.21 (m, 9H), 7.18-7.11 (m, 2H), 6.89-6.81 (m, 2H), 5.81 (brs, 1H), 4.99 (s, 2H), 4.71-4.61 (m, 1H), 2.96-2.86 (m, 1H), 2.85-2.73 (m, 1H), 2.67-2.58 (m, 1H), 1.98-1.27 (m, 6H).

EXAMPLE 12(23)

1-(2-benzyloxyphenyl carbamoyl)-2,3,4,5-tetrahydro-1H-1-benzazepine

TLC:Rf 0.54 (n-hexane:ethyl acetate=3:1);
NMR (CDCl$_3$):δ 8.29 (dd, J=7.5 Hz, 1.8 Hz, 1H), 7.38-6.82 (m, 12H), 4.81 (s, 2H), 4.75-4.67 (m, 1H), 2.91-2.51 (m, 3H), 2.08-1.74 (m, 3H), 1.48-1.24 (m, 1H).

REFERENCE EXAMPLE 13

5-methyl-2-nitrobenzoate methyl

At temperature of −20° C. or less, 5-methyl-2-nitrobenzoic acid (18.1 g) was added to methanol (100 ml) to which thionyl chloride (10 ml) have been added was refluxed for 2 days. A crystal extracted from the radiationally cooled reactive mixture was removed by filtration followed to be washed in clear water. A title compound (13.1 g) having the following physical properties values was obtained.
TLC:Rf 0.46 (n-hexane:ethyl acetate=4:1);
NMR (CDCl$_3$):δ 7.87 (d, J=8.1 Hz, 1H), 7.48 (d, J=1.5 Hz, 1H), 7.40 (m, 1 H), 3.92 (s, 3H), 2.47 (s, 3H).

REFERENCE EXAMPLE 14

2-amino-5-methylbenzoate methyl

A mixture of which under argon gas 5% palladium carbon (1.55 g) has been added to the compound (5.85 g) prepared in Reference example 13, which ethyl acetate (150 ml) had been added, was stirred for 8 hours under hydrate gas. The reactive mixture filtered with celite was concentrated. A title compound (4.89 g) having the following physical properties values was obtained.
TLC:Rf 0.44 (n-hexane:ethyl acetate=6:1);
NMR (CDCl$_3$):δ 7.66 (dd, J=1.8 Hz, 0.6 Hz, 1H), 7.10 (m, 1H), 6.59 (d, J=8.7 Hz, 1H), 5.56 (bs, 1H), 3.86 (s, 3H), 2.23 (s, 3H).

REFERENCE EXAMPLE 15

5-methyl-2-toluenesulfonyl aminobenzoate methyl

A mixture of which tosyl chloride (7.022 g) has been added to pyridine (15 ml) solution of the compound (4.69 g) prepared in Reference example 14 during storage in ice was stirred at room temperature over night. The crystal extracted from the reactive mixture dissolved to water/2N hydrochloric acid was removed by filtration followed to be washed in clear water. A title compound (8.84 g) having the following physical properties values was obtained.
TLC:Rf 0.41 (n-hexane:ethyl acetate=4:1);
NMR (CDCl$_3$):δ 10.38 (s, 1H), 7.72-7.69 (m, 3H), 7.60 (d, J=8.1 Hz, 1H), 7.28-7.19 (m, 3H), 3.85 (s, 3H), 2.36 (s, 3H), 2.27 (s, 3H).

REFERENCE EXAMPLE 16

2-[N-(3-methoxycarbonylpropyl)-N-toluenesulfonylamino]-5-methyl-benzoate methyl

A mixture of which 4-bromobutanoic acid methyl (7.53 g) and potassium carbonate (7.66 g) are added to N, N-dimethylformamide (45 ml) solution of the compound (8.83 g) prepared in Reference example 15 was stirred at 80° C. over night. After radiationally cooling, the reactive mixture dissolved to ice water was extracted by ethyl acetate. The organic layer sequentially washed with water and saturated brine was concentrated after drying with sulfuric anhydride magnesium. The obtained residue was washed by n-hexane: ethyl acetate (4:1). A title compound (10.82 g) having the following physical properties values was obtained.
TLC:Rf 0.42 (n-hexane:ethyl acetate=2:1);
NMR (CDCl$_3$):δ 7.67 (d, J=2.1 Hz, 1H), 7.48-7.44 (m, 2H), 7.24-7.19 (m, 3H), 6.79 (d, J=8.4 Hz, 1H), 3.85-3.45 (br, 2H), 3.80 (s, 3H), 3.64 (s, 3H), 2.46 (t, J=7.5 Hz, 2H), 2.41 (s, 3H), 2.38 (s, 3H), 1.91-1.81 (m, 2H).

REFERENCE EXAMPLE 17

5-hydroxy-4-methoxycarbonyl-7-methyl-1-toluenesulfonyl-2,3-dihydro-1H-1-benzazepine A mixture of which N, N-dimethylformamide (30 ml) solution of the compound (4.20 g) prepared in Reference example 16 has been added to tetrahydrofuran (30 ml) solution of sodium hydride (2.31 g) during storage in ice was stirred at room temperature for 90 minutes. 1N hydrochloric acid was added to the reactive mixture to which acetate (3.5 ml) has been added during storage in ice, followed to be extracted by ethyl acetate. The organic layer sequentially washed with saturated sodium bicarbonate solution (4 times) and saturated brine was concentrated after drying with sulfuric anhydride magnesium. The obtained residue was washed by n-hexane:ethyl acetate (4:1). A title compound (2.85 g) having the following physical properties values was obtained.
TLC:Rf 0.39 (n-hexane:ethyl acetate=4:1);
NMR (CDCl$_3$):δ 11.87 (s, 1H), 7.45 (m, 1H), 7.38 (d, J=8.1 Hz, 2H), 7.33-7.29 (m, 2H), 7.16 (d, J=8.1 Hz, 2H), 4.07 (t, J=6.3 Hz, 2H), 3.71 (s, 3H), 2.39 (s, 6H), 2.32-2.22 (br, 2H).

REFERENCE EXAMPLE 18

7-methyl-1-toluenesulfonyl-5-oxo-2,3,4,5-tetrahydro-1H-1-benzazepine

A mixture of which water (0.2 ml) has been added to dimethyl sulphoxide (2 ml) solution of the compound (2.84 g) prepared in Reference example 17 was stirred at 125° C. over night. After radiationally cooling, the crystal extracted from the reactive mixture dissolved to ice water was removed by filtration followed to be washed in clear water. The obtained raw crystal was washed by methanol (7 ml). A title compound (1.94 g) having the following physical properties values was obtained.

TLC:Rf 0.24 (n-hexane:ethyl acetate=4:1);

NMR (CDCl$_3$): δ 7.59-7.55 (m, 2H), 7.49 (s, 1H), 7.37-7.31 (m, 2H), 7.28-7.25 (m, 2H), 3.83 (t, J=6.6 Hz, 2H), 2.42 (s, 3H), 2.38 (s, 3H), 2.37-2.33 (m, 2H), 1.95-1.87 (m, 2H).

REFERENCE EXAMPLE 19

7-methyl-1-toluenesulfonyl-2,3,4,5-tetrahydro-1H-1-benzazepine

A mixture of which hydrazine monohydrate (1.1 ml) and potassium hydroxide (3.09 g) have been added to ethylene glycol (30 ml) solution of the compound (1.87 g) prepared in Reference example 18 was stirred at 180° C. for 3 hours. The radiationally cooled reactive mixture, which ice water was added, was extracted by ethyl acetate after being adjusted to pH 7 with 2N hydrochloric acid. The organic layer sequentially washed with saturated sodium bicarbonate solution and saturated brine was concentrated after drying with sulfuric anhydride magnesium. The obtained residue was purified by silica gel column chromatography (n-hexane:ethyl acetate=6:1). A title compound (1.26 g) having the following physical properties values was obtained.

TLC:Rf 0.27 (n-hexane:ethyl acetate=9:1);

NMR (CDCl$_3$):δ 7.63-7.58 (m, 2H), 7.25-7.23 (m, 2H), 7.14 (d, J=7.8 Hz, 1H), 6.97-6.91 (m, 2H), 3.84-3.52 (br, 2H), 2.42 (s, 3H), 2.36-2.32 (m, 2H), 2.30 (s, 3H), 1.82-1.75 (m, 2H), 1.60-1.44 (br, 2H).

REFERENCE EXAMPLE 20

7-methyl-2,3,4,5-tetrahydro-1H-benzazepine

A mixture of which 48% hydrobromic acid solution (12 ml) has been added to acetate (18 ml) solution of the compound (1.21 g) prepared in Reference example 19 was refluxed for 3 days. The radiationally cooled reactive mixture, which ice water was added, was extracted by ethyl acetate twice after being neutralized with saturated sodium bicarbonate. The organic layer washed with saturated brine was concentrated after drying with sulfuric anhydride magnesium. The obtained residue was purified by silica gel column chromatography (n-hexane:ethyl acetate=9:1). A title compound (485 mg) having the following physical properties values was obtained.

TLC:Rf 0.26 (n-hexane:ethyl acetate=9:1);

NMR (CDCl$_3$): δ 6.92 (s, 1H), 6.84 (dd, J=7.8 Hz, 1.5 Hz, 1H), 6.64 (d, J=7.8 Hz, 1H), 3.94-3.34 (br, 1H), 3.03-2.99 (m, 2H), 2.75-2.71 (m, 2H), 2.25 (s, 3H), 1.83-1.75 (m, 2H), 1.66-1.58 (m, 2H).

EXAMPLE 13

7-methyl-1-phenylcarbamoyl-2,3,4,5-tetrahydro-1H-1-benzazepine

The present compound having the following physical properties values was obtained by operating as well as the method represented by Example 1 using the compound prepared in Reference example 20 instead of the compound prepared in Reference example 6.

TLC:Rf 0.22 (n-hexane:ethyl acetate=7:1);

NMR (CDCl$_3$):δ 7.32-7.06 (m, 7H), 7.00-6.94 (m, 1H), 6.25 (s, 1H), 4.78-4.57 (br, 1H), 2.95-2.54 (m, 3H), 2.38 (s, 3H), 2.10-1.72 (br, 3H), 1.48-1.20 (br, 1H).

EXAMPLE 13(1)-EXAMPLE 13(2)

The present compound having the following physical properties values was obtained by operating as well as a method sequentially represented by Reference examples 13, 14, 15, 16, 17, 18, 19, 20, and Example 13 using a corresponding compound instead of 5-methyl-2-nitrobenzoic acid.

EXAMPLE 13(1)

9-methyl-1-phenylcarbamoyl-2,3,4,5-tetrahydro-1H-benzazepine

TLC:Rf 0.37 (n-hexane:ethyl acetate=6:1);

NMR (CDCl$_3$):δ 7.30-7.14 (m, 7H), 6.98 (m, 1H), 6.04 (s, 1H), 4.66 (m, 1H), 2.87 (m, 1H), 2.74-2.58 (m, 2H), 2.28 (s, 3H), 2.15-1.96 (m, 2H), 1.79 (m, 1H), 1.36 (m, 1H).

EXAMPLE 13(2)

1-phenylcarbamoyl-2,3,4,5-tetrahydro-1H-pyrid[2,3-b]-1-azepine

TLC:Rf 0.32 (n-hexane:ethyl acetate=2:1);

NMR (CDCl$_3$):δ 9.48 (bs, 1H), 8.32 (dd, J=4.8 Hz, 1.8 Hz, 1H), 7.61 (dd, J=7.5 Hz, 1.8 Hz, 1H), 7.43-7.39 (m, 2H), 7.29-7.23 (m, 2H), 7.13 (dd, J=7.5 Hz, 4.8 Hz, 1H), 7.02-6.96 (m, 1H), 3.92-3.67 (br, 2H), 2.85-2.81 (m, 2H), 2.02-1.94 (m, 2H), 1.84-1.72 (m, 2H).

EXAMPLE 14

1-(4-hydroxyphenyl carbamoyl)-2,3,4,5-tetrahydro-1H-1-benzazepine

A mixture of which 10% palladium carbon (30 mg) has been added to ethanol (30 ml) solution of the compound (262 mg) prepared in Example 12(2) was stirred for 2 hours under hydrate gas. The filtrate obtained from the reactive mixture filtered with celite was concentrated. The obtained residue was purified by silica gel column chromatography (n-hexane:ethyl acetate=3:2). The present compound (169 mg) having the following physical properties values was obtained.

TLC:Rf 0.41 (n-hexane:ethyl acetate=1:1);

NMR (CDCl$_3$+CD$_3$OD):δ 7.35-7.26 (m, 4H), 7.08-7.02 (m, 2H), 6.75-6.69 (m, 2H), 6.12 (bs, 1H), 4.72-4.50 (m, 1H), 2.93-2.57 (m, 3H), 2.15-1.70 (m, 3H), 1.54-1.21 (m, 1H).

EXAMPLE 14(1)-EXAMPLE 14 (11)

The present compound having the following physical properties values was obtained by operating as well as the method represented by Example 9 using a corresponding compound instead of the compound prepared in example 12(2).

EXAMPLE 14(1)

8-fluoro-5-(4-fluorophenyl)-1-(4-hydroxyphenylcarbamoyl)-2,3,4,5-tetrahydro-1H-1-benzazepine TLC:Rf 0.38 (n-hexane:ethyl acetate=1:1);
NMR (CDCl$_3$):δ 7.42-6.55 (m, 11H), 6.10 (bs, 1H), 5.76 (bs, 1H), 4.72-4.56 (m, 1H), 4.24-4.12 (m, 1H), 2.95-2.76 (m, 1H), 2.26-2.06 (m, 2H), 1.96-1.78 (m, 2H).

EXAMPLE 14(2)

1-(4-hydroxyphenylcarbamoyl)-1, 2,3,4,5,6-hexahydro-1-benzazocine

TLC:Rf 0.24 (n-hexane:ethyl acetate=1:1);
NMR (CD$_3$OD):δ 7.40-7.34 (m, 3H), 7.29-7.23 (m, 1H), 7.03-6.96 (m, 2H), 6.69-6.62 (m, 2H), 4.59-4.43 (m, 1H), 3.03-2.85 (m, 1H), 2.78-2.65 (m, 2H), 2.01-1.23 (m, 6H).

EXAMPLE 14(3)

1-(4-fluorophenylcarbamoyl)-7-hydroxy-2,3,4,5-tetrahydro-1H-1benzazepine

TLC:Rf 0.44 (n-hexane:ethyl acetate=1:1);
NMR (CDCl$_3$):δ 7.28-7.21 (m, 2H), 7.15 (d, J=8.4 Hz, 1H), 6.97-6.89 (m, 2H), 6.79 (d, J=3.0 Hz, 1H), 6.73 (dd, J=8.4 Hz, 3.0 Hz, 1H), 6.20 (brs, 1H), 5.30 (brs, 1H), 4.66-4.57 (m, 1H) 2.85-2.58 (m, 3H), 2.05-1.92 (m, 2H), 1.86-1.73 (m, 1H), 1.44-1.32 (m, 1H).

EXAMPLE 14(4)

1-(3-hydroxyphenylcarbamoyl)-2,3,4,5-tetrahydro-1H-1-benzazepine

TLC: Rf 0.14 (n-hexane:ethyl acetate=3:1);
NMR (CDCl$_3$):δ 7.62-7.58 (m, 1H), 7.36-7.27 (m, 4H), 7.02 (t, J=8.1 Hz, 1 H), 7.00 (brs, 1H), 6.51 (ddd, J=8.1 Hz, 2.7 Hz, 0.6 Hz, 1H), 6.27 (ddd, J=8.1 Hz, 2.7 Hz, 0.9 Hz, 1H), 6.24 (brs, 1H), 4.72-4.59 (m, 1H) 2.91-2.63 (m, 3H), 2.08-1.74 (m, 3H), 1.49-1.24 (m, 1H).

EXAMPLE 14(5)

1-(2-hydroxyphenylcarbamoyl)-2,3,4,5-tetrahydro-1H-1-benzazepine

TLC:Rf 0.58 (n-hexane:ethyl acetate=3:1);
NMR (CDCl$_3$):δ 9.78 (s, 1H), 7.39-7.30 (m, 4H), 7.05-6.97 (m, 2H), 6.76-6.69 (m, 1H), 6.56-6.51 (m, 1H), 6.24 (brs, 1H), 4.70-4.59 (m, 1H), 2.95-2.68 (m, 3H), 2.10-1.93 (m, 2H), 1.89-1.78 (m, 1H), 1.44-1.30 (m, 1H).

EXAMPLE 14(6)

1-(3-hydroxy-4-methoxyphenylcarbamoyl)-2,3,4,5-tetrahydro-1H-1-benzazepine

TLC:Rf 0.50 (n-hexane:ethyl acetate=1:1);
NMR (CDCl$_3$):δ 7.41 (d, J=2.4 Hz, 1H), 7.35-7.26 (m, 4H), 6.73 (d, J=8.4 Hz, 1H), 6.33 (dd, J=8.4 Hz, 2.4 Hz, 1H) 6.09 (brs, 1H), 5.35 (s, 1H), 4.78-4.58 (m, 1H), 3.89 (s, 3H), 2.94-2.57 (m, 3H), 2.08-1.71 (m, 3H), 1.51-1.24 (m, 1H).

EXAMPLE 14(7)

1-(4-hydroxyphenylcarbamoyl)-7-methoxy-2,3,4,5-tetrahydro-1H-1-benzazepine

TLC:Rf 0.31(n-hexane:ethyl acetate=1:1);
NMR (CDCl$_3$):δ 7.21 (d, J=8.7 Hz, 1H), 7.08-7.02 (m, 2H), 6.83 (d, J=2.7 Hz, 1H), 6.78 (dd, J=8.7 Hz, 2.7 Hz, 1H), 6.69-6.63 (m, 2H), 6.07 (brs, 1H), 5.91 (brs, 1H), 4.68-4.56 (m, 1H), 3.83 (s, 3H), 2.90-2.58 (m, 3H), 2.04-1.69 (m, 3H), 1.49-1.25 (m, 1H).

EXAMPLE 14(8)

1-(4-hydroxyphenylcarbamoyl)-6-methoxy-2,3,4,5-tetrahydro-1H-1-benzazepine

TLC:Rf 0.51 (n-hexane:ethyl acetate=1:1);
NMR (CDCl$_3$):δ 7.22 (t, J=7.8 Hz, 1H), 7.06-6.99 (m, 2H), 6.92 (dd, J=7.8 Hz, 1.2 Hz, 1H), 6.87 (dd, J=7.8 Hz, 1.2 Hz, 1H), 6.68-6.61 (m, 2H), 6.33 (s, 1H), 6.10 (brs, 1H), 4.67-4.57 (m, 1H), 3.86 (s, 3H), 3.44-3.32 (m, 1H), 2.79-2.62 (m, 1H), 2.42-2.27 (m, 1H), 2.07-1.69 (m, 3H), 1.38-1.17 (m, 1H).

EXAMPLE 14(9)

1-(4-hydroxyphenylcarbamoyl)-8-methoxy-2,3,4,5-tetrahydro-1H-1-benzazepine

TLC:Rf 0.48 (n-hexane:ethyl acetate=1:1);
NMR (CDCl$_3$):δ 7.22 (d, J=8.4 Hz, 1H), 7.11-7.05 (m, 2H), 6.86 (d, J=2.4 Hz, 1H), 6.82 (dd, J=8.4 Hz, 2.4 Hz, 1H), 6.70-6.64 (m, 2H), 6.11 (brs, 1H), 5.60 (s, 1H), 4.77-4.51 (m, 1H), 3.81 (s, 3H), 2.84-2.58 (m, 3H), 2.09-1.69 (m, 3H), 1.49-1.20 (m, 1H).

EXAMPLE 14(10)

8-hydroxy-1-(4-hydroxyphenyl carbamoyl)-2,3,4,5-tetrahydro-1H-1-benzazepine

TLC:Rf 0.27 (n-hexane:ethyl acetate=1:1);
NMR (CDCl$_3$+CD$_3$OD):δ 7.16-7.12 (m, 1H), 7.09-7.03 (m, 2H), 6.78-6.69 (m, 4H), 6.34 (brs, 1H), 4.67-4.38 (m, 1H), 2.84-2.59 (m, 3H), 2.08-1.73 (m, 3H), 1.58-1.19 (m, 1H).

EXAMPLE 14(11)

1-(4-hydroxyphenylcarbamoyl)-8-methyl-2,3,4,5-tetrahydro-1H-1-benzazepine

TLC:Rf 0.40 (n-hexane:ethyl acetate=1:1);
NMR (DMSO-d6):δ 8.99 (s, 1H), 7.30 (s, 1H), 7.18-7.15 (m, 1H), 7.12-7.07 (m, 2H), 7.01-6.99 (m, 2H), 6.61-6.56 (m, 2H), 3.80-3.20 (br, 2H), 2.67-2.64 (m, 2H), 2.25 (s, 3H), 1.74-1.66 (m, 2H), 1.64-1.45 (br, 2H).

EXAMPLE 15

1-(4-hydroxy-3-nitrophenylcarbamoyl)-2,3,4,5-tetrahydro-1H-1-benzazepine

A mixture of which 2N hydrochloric acid (3.1 ml) has been added to methanol (10 ml) solution of compound (1.17 g) prepared in Example 12(5) was stirred at 65° C. for 3 hours. The reactive mixture radiationally cooled up to room temperature was extracted by dichloromethane after being neutralized with 2N sodium hydroxide solution. The organic layer was concentrated after drying with sulfuric anhydride magnesium. The obtained residue was recrystallized from n-hexane ethyl acetate after being purified by silica gel column chromatography (n-hexane:ethyl acetate=5:1). The present compound (136 mg) having the following physical properties values was obtained.

TLC:Rf 0.44 (n-hexane:ethyl acetate=2:1);

NMR (CDCl$_3$):δ 8.01 (d, J=2.7 Hz, 1H), 7.61 (dd, J=9.0 Hz, 2.7 Hz, 1H), 7.38-7.24 (m, 4H), 7.03 (d, J=9.0 Hz, 1H), 6.21 (brs, 1H), 4.77-4.58 (m, 1H), 2.97-2.61 (m, 3H), 2.04-1.70 (m, 3H), 1.49-1.22 (m, 1H).

EXAMPLE 15(1)-EXAMPLE 14 (11)

The present compound having the following physical properties values was obtained by operating as well as the method represented by Example 15 using a corresponding compound instead of the compound prepared in Example 12(5).

EXAMPLE 15(1)

8-hydroxy-1-phenylcarbamoyl-2,3,4,5-tetrahydro-1H-1-benzazepine

TLC:Rf 0.24 (n-hexane:ethyl acetate=2:1);

NMR (CD$_3$OD):δ 7.30-7.12 (m, 5H), 7.02-6.96 (m, 1H), 6.75-6.70 (m, 2H), 4.80-4.50 (b, 1H), 2.80-2.63 (m, 3H), 2.00-1.40 (m, 4H).

EXAMPLE 15(2)

1-(3-chloro-4-hydroxyphenylcarbamoyl)-2,3,4,5-tetrahydro-1H-1-benzazepine

TLC:Rf 0.26 (n-hexane:ethyl acetate=2:1);

NMR (CDCl$_3$):δ 7.48 (d, J=2.7 Hz, 1H), 7.35-7.27 (m, 4H), 6.93 (dd, J=8.7 Hz, 2.7 Hz, 1H), 6.85 (d, J=8.7 Hz, 1H), 6.07 (brs, 1H), 5.48 (brs, 1H), 4.74-4.57 (m, 1H), 2.93-2.56 (m, 3H), 2.06-1.68 (m, 3H), 1.50-1.28 (m, 1H).

EXAMPLE 15(3)

1-(2-chloro-4-hydroxyphenylcarbamoyl)-2,3,4,5-tetrahydro-1H-1-benzazepine

TLC:Rf 0.28 (n-hexane:ethyl acetate=2:1);

NMR (CDCl$_3$):δ 7.60 (d, J=8.7 Hz, 1H), 7.40-7.25 (m, 4H), 6.72 (d, J=2.7 Hz, 1H), 6.59 (dd, J=8.7 Hz, 2.7 Hz, 1H), 6.54 (s, 1H), 6.34 (brs, 1H), 4.70-4.59 (m, 1H), 2.98-2.66 (m, 3H), 2.10-1.77 (m, 3H), 1.53-1.29 (m, 1H).

EXAMPLE 15(4)

1-(4-hydroxyphenylcarbamoyl)-8-nitro-2,3,4,5-tetrahydro-1H-1-benzazepine

TLC:Rf 0.31 (ethyl acetate: n-hexane=3:2);

NMR (DMSO-d6):δ 9.05 (s, 1H), 8.07 (dd, J=8.4 Hz, 2.4 Hz, 1H), 8.00 (d, J=2.4 Hz, 1H), 7.87 (s, 1H), 7.60 (d, J=8.4 Hz, 1H), 7.18-7.10 (m, 2H), 6.66-6.59 (m, 2H), 3.75-3.47 (m, 2H), 2.90-2.80 (m, 2H), 1.85-1.50 (m, 4H).

EXAMPLE 15(5)

1-(4-hydroxy-2-methoxyphenylcarbamoyl)-2,3,4,5-tetrahydro-1H-1-benzazepine

TLC:Rf 0.32(n-hexane:ethyl acetate=1:1);

NMR (CDCl$_3$):δ 7.73 (bd, J=9.0 Hz, 1H), 7.36-7.23 (m, 4H), 6.49 (s, 1H), 6.35-6.15 (m, 3H), 4.77-4.52 (m, 1H), 3.57 (s, 3H), 2.95-2.55 (m, 3H), 2.13-1.70 (m, 3H), 1.50-1.20 (m, 1H)

EXAMPLE 15(6)

1-(2-fluoro-4-hydroxyphenylcarbamoyl)-2,3,4,5-tetrahydro-1H-1-benzazepine

TLC:Rf 0.48 (n-hexane:ethyl acetate=1:1);

NMR (CDCl$_3$):δ 7.37-7.24 (m, 6H), 6.46-6.38 (m, 2H), 5.96 (s, 1H), 4.72-4.56 (m, 1H), 3.00-2.60 (m, 3H), 2.12-1.75 (m, 3H), 1.50-1.30 (m, 1H).

EXAMPLE 15(7)

1-(4-hydroxy-2-methylphenylcarbamoyl)-2,3,4,5-tetrahydro-1H-1-benzazepine

TLC:Rf 0.31 (n-hexane:ethyl acetate=1:1);

NMR (CDCl$_3$):δ 7.38-7.22 (m, 4H), 7.10-7.03 (m, 2H), 6.45-6.40 (m, 2H), 5.78 (bs, 1H), 4.73-4.58 (m, 1H), 3.00-2.63 (m, 3H), 2.13-1.73 (m, 6H), 1.50-1.29 (m, 1H).

EXAMPLE 15(8)

1-(4-hydroxy-3-methylphenylcarbamoyl )-2,3,4,5-tetrahydro-1H-1-benzazepine

TLC:Rf 0.51 (n-hexane:ethyl acetate=1:1);

NMR (CDCl$_3$):δ 7.34-7.24 (m, 4H), 7.00-6.97 (m, 1H), 6.89 (dd, J=8.7 Hz, 2.7 Hz, 1H), 6.58 (d, J=8.7 Hz, 1H), 6.01 (s, 1H), 5.53-5.37 (m, 1H), 4.75-4.60 (m, 1H), 2.96-2.58 (m, 3H), 2.15 (s, 3H), 2.10-1.72 (m, 3H), 1.50-1.23 (m, 1H).

EXAMPLE 15(9)

1-(3-fluoro-4-hydroxyphenylcarbamoyl )-2,3,4,5-tetrahydro-1H-1-benzazepine

TLC:Rf 0.56 (n-hexane:ethyl acetate=1:1);

NMR (CDCl$_3$):δ 7.36-7.24 (m, 5H), 6.84-6.76 (m, 1H), 6.66 (ddd, J=8.4 Hz, 2.4 Hz, 1.5 Hz, 1H), 6.09 (s, 1H), 5.44 (bs, 1H), 4.74-4.58 (m, 1H), 2.94-2.65 (m, 3H), 2.10-1.72 (m, 3H), 1.50-1.28 (m, 1H)

EXAMPLE 15(10)

1-(4-hydroxyphenylcarbamoyl)-2,3,4,5-tetrahydro-1H-pyrid[2,3-b]-1-azepine

TLC: Rf 0.53 (chloroform: methanol=9:1);

NMR(DMSO-d6):δ 9.01 (s, 1H), 8.65 (s, 1H), 8.27 (dd, J=4.8 Hz, 1.8 Hz, 1H), 7.74 (dd, J=7.5 Hz, 1.8 Hz, 1H), 7.22-7.12 (m, 3H), 6.66-6.58 (m, 2H), 3.73-3.46 (br, 2H), 2.77-2.74 (m, 2H), 1.78-1.61 (m, 4H).

EXAMPLE 15(11)

1-(4-hydroxyphenylcarbamoyl)-7-methyl-2,3,4,5-tetrahydro-1H-1-benzazepine

TLC:Rf 0.18 (n-hexane:ethyl acetate=2:1);
NMR (DMSO-d6):δ 8.96 (bs, 1H), 7.24 (s, 1H), 7.11-6.99 (m, 5H), 6.60-6.55 (m, 2H), 3.80-3.00 (br, 2H), 2.68-2.64 (m, 2H), 2.27 (s, 3H), 1.77-1.43 (m, 4H).

EXAMPLE 16

1-(4-aminophenylcarbamoyl)-2,3,4,5-tetrahydro-1H-1-benzazepine

The present compound having the following physical properties values was obtained by operating as well as the method represented by Example 14 using the compound prepared in Example 7(23) instead of the compound prepared in Example 12(2).

TLC:Rf 0.20 (n-hexane:ethyl acetate=1:1);
NMR (CDCl$_3$):δ 7.36-7.23 (m, 4H), 7.09-7.02 (m, 2H), 6.62-6.56(m, 2H), 5.99 (brs, 1H), 4.78-4.54 (m, 1H), 3.49 (brs, 2H), 2.96-2.56 (m, 3H), 2.11-1.70 (m, 3H), 1.49-1.25 (m, 1H).

EXAMPLE 16(1)-EXAMPLE 16 (3)

The present compound having the following physical properties values was obtained by operating as well as the method represented by Example 16 using a corresponding compound.

EXAMPLE 16(1)

1-(3-amino-4-hydroxyphenylcarbamoyl)-2,3,4,5-tetrahydro-1H-1-benzazepine hydrochloride TLC:Rf 0.28 (dichloromethane: methanol=20:1);
NMR (CDCl$_3$+CD$_3$OD):δ 7.39 (d, J=2.4 Hz, 1H), 7.36-7.27 (m, 4H), 6.94 (dd, J=8.7 Hz, 2.4 Hz, 1H), 6.87 (d, J=8.7 Hz, 1H), 4.73-4.40 (m, 1H), 2.91-2.74 (m, 3H), 2.12-1.79 (m, 3H), 1.61-1.29 (m, 1H).

EXAMPLE 16(2)

8-amino-1-phenylcarbamoyl-2,3,4,5-tetrahydro-1H-1-benzazepine

TLC:Rf 0.56 (ethyl acetate: n-hexane=1:1);
NMR (CDCl$_3$):δ 7.34-7.28 (m, 2H), 7.27-7.19 (m, 2H), 7.08 (d, J=7.8 Hz, 1H), 7.01-6.94 (m, 1H), 6.62 (d, J=2.4 Hz, 1H), 6.60 (dd, J=7.8 Hz, 2.4 Hz, 1 H), 6.33 (bs, 1H), 4.73-4.50 (m, 1H), 3.70 (bs, 2H), 2.85-2.50 (m, 3H), 2.07-1.67 (m, 3H), 1.45-1.20 (m, 1H).

EXAMPLE 16(3)

8-amino-1-(4-hydroxyphenyl carbamoyl)-2,3,4,5-tetrahydro-1H-1-benzazepine

TLC:Rf 0.43 (ethyl acetate: n-hexane=3:1);
NMR (CDCl$_3$+CD$_3$OD):δ 7.12-7.03 (m, 3H), 6.76-6.69 (m, 2H), 6.68-6.52 (m, 2H), 4.65-4.40 (m, 1H), 2.80-2.60 (m, 3H), 2.10-1.75 (m, 3H), 1.53-1.20 (m, 1H).

EXAMPLE 17

1-(4-ethoxycarbonylmethyloxyphenylcarbamoyl)-2,3,4,5-tetrahydro-1H-1-benzazepine A mixture of which potassium carbonate (734 mg) and ethyl bromoacetate (0.59 ml) have been added to tetrahydrofuran-N,N-dimethylformamide (40 ml/40 ml) solution of the compound (1.5 g) prepared in Example 14 with stirring at room temperature was stirred with warming to 90° C. for 5 hours. The reactive mixture cooled to room temperature, which water was added, was extracted by ethyl acetate, followed to be concentrated. The crystal extracted from the residue to which water had been added was removed by filtration. The crystal was dried after being washed by clear water. The present compound (1.90 g) having the following physical properties values was obtained.

TLC:Rf 0.30 (n-hexane:ethyl acetate=2:1);
NMR (CDCl$_3$):δ 7.36-7.25 (m, 4H), 7.24-7.17 (m, 2H), 6.84-6.77 (m, 2H), 6.11 (brs, 1H), 4.77-4.57 (m, 1H), 4.56 (s, 2H), 4.25 (q, J=6.9 Hz, 2H), 2.92-2.57 (m, 3H), 2.09-1.71 (m, 3H), 1.58-1.20 (m, 4H).

EXAMPLE 18

1-(4-carboxymethyloxyphenylcarbamoyl)-2,3,4,5-tetrahydro-1H-1-benzazepine

A mixture of which 2N sodium hydroxide solution (5.16 ml) had been added to-methanol (100 ml) solution of the compound (1.9 g) prepared in Example 17 with stirring at room temperature was stirred over night. The reactive mixture to which 1 N hydrochloric acid had been added was adjusted to acidulous. Then, the organic layer extracted by methylene chloride was concentrated. The obtained residue was washed by n-hexane ethyl acetate (1:1). The present compound (1.57 g) having the following physical properties values was obtained.

TLC:Rf 0.20 (methylene chloride: methanol=9:1);
NMR (CDCl$_3$):δ 7.35-7.26 (m, 4H), 7.22-7.16 (m, 2H), 6.83-6.77 (m, 2H), 6.13 (brs, 1H), 4.78-4.50 (m, 1H), 4.58 (s, 2H), 2.96-2.57 (m, 3H), 2.11-1.69 (m, 3H), 1.49-1.20 (m, 1H).

EXAMPLE 19

1-(4-carbomethoxyphenylcarbamoyl)-2,3,4,5-tetrahydro-1H-1-benzazepine

A mixture of which tetrahydrofuran (3 ml) solution of triethylamine (2.5 ml) and 4-aminobenzoic acid methyl (151 mg) had been added to tetrahydrofuran (2 ml) solution of triphosgene (198 mg) with stirring under argon gas at 0° C. was stirred at room temperature for 10 minutes. The filtrate obtained by removing triethylamine hydrochloride by filtration was concentrated, then the yellow solid (370 mg) was obtained. A mixture of which toluene (3 ml) solution of 2,3,4,5-tetrahydro-1H-1-benzazepine (98 mg) had been added to this toluene (5 ml) solution was stirred at 120° C. over night. The obtained residue of which the reactive mixture had been concentrated was purified by silica gel column chromatography (n-hexane:ethyl acetate=5:1, 3:1, and 2:1 gradually). The present compound (71 mg) having the following physical properties values was obtained.

TLC:Rf 0.46 (n-hexane:ethyl acetate=2:1);
NMR (CDCl$_3$):δ 7.94-7.88 (m, 2H), 7.40-7.28 (m, 6H), 6.45 (brs, 1H), 4.77-4.63 (m, 1H), 3.85 (s, 3H), 2.91-2.64 (m, 3H), 2.09-1.74 (m, 3H), 1.49-1.27 (m, 1H).

EXAMPLE 19(1)-EXAMPLE 19(4)

The present compound having the following physical properties values was obtained by operating as well as the method represented by Example 19 using a corresponding compound.

EXAMPLE 19(1)

1-(4-benzyloxy-2-nitrophenylcarbamoyl )-2,3,4,5-tetrahydro-1H-1-benzazepine

TLC:Rf 0.46 (n-hexane:ethyl acetate=4:1);
NMR (CDCl$_3$):δ 9.48 (bs, 1H), 8.66 (d, J=9.3 Hz, 1H), 7.64 (d, J=3.0 Hz, 1H), 7.46-7.23 (m, 10H), 5.05 (s, 2H), 4.68-4.55 (m, 1H), 2.90-2.68 (m, 3H), 2.10-1.74 (m, 3H), 1.50-1.30 (m, 1H).

EXAMPLE 19(2)

1-(2-fluoro-4-methoxymethyloxyphenylcarbamoyl)-2,3,4,5-tetrahydro-1H-1-benzazepine TLC:Rf 0.50 (n-hexane:ethyl acetate=2:1);
NMR (CDCl$_3$):δ 7.97 (t, J=9.0 Hz, 1H), 7.34-7.24 (m, 4H), 6.78 (ddd, J=9.0 Hz, 2.4 Hz, 1.5 Hz, 1H), 6.71 (dd, J=9.0 Hz, 2.4 Hz, 1H), 6.26 (bs, 1H), 5.09 (s, 2H), 4.8-4.6 (m, 1H), 3.44 (s, 3H), 2.9-2.6 (m, 3H), 2.1-1.7 (m, 3H), 1.5-1.2 (m, 1H).

EXAMPLE 19(3)

1-(4-methoxymethyloxy-2-methyl phenylcarbamoyl)-2,3,4,5-tetrahydro-1H-1benzazepine TLC:Rf 0.38 (n-hexane:ethyl acetate=2:1);
NMR (CDCl$_3$):δ 7.63 (d, J=8.4 Hz, 1H), 7.38-7.26 (m, 4H), 6.85 (dd, J=8.4 Hz, 3.0 Hz, 1H), 6.77 (d, J=3.0 Hz, 1H), 5.89 (bs, 1H), 5.10 (s, 2H), 4.75-4.55 (m, 1H), 3.44 (s, 3H), 2.95-2.60 (m, 3H), 2.10-1.70 (m, 3H), 1.89 (s, 3H), 1.50-1.20 (m, 1H).

EXAMPLE 19(4)

1-(4-methoxymethyloxy-2-methylphenylcarbamoyl) 2,3,4,5-tetrahydro-1H-1-benzazepine TLC: Rf 0.43 (n-hexane:ethyl acetate=2:1);
NMR (CDCl$_3$):δ 7.34-7.25 (m, 4H), 7.12 (d, J=2.7 Hz, 1H), 7.00 (dd, J=8.7 Hz, 2.7 Hz, 1H), 6.91 (d, J=8.7 Hz, 1H), 6.05 (bs, 1H), 5.12 (s, 2H), 4.8-4.6 (m, 1H), 3.45 (s, 3H), 2.9-2.6 (m, 3H), 2.19 (s, 3H), 2.1-1.7 (m, 3H), 1.5-1.2 (m, 1H).

EXAMPLE 20

1-(4-carboxyphenylcarbamoyl)-2,3,4,5-tetrahydro-1H-1-benzazepine

A mixture of which 2N sodium hydroxide solution (1 ml) had been added to methanol (20 ml) solution of the compound (382 mg) prepared in Example 19 was stirred with stirring at room temperature for 2 hours. Tetrahydrofuran (10 ml) and 2N sodium hydroxide solution (3 ml) were sequentially added to the mixture, which was stirred at room temperature for 2 days. The reactive mixture was adjusted to pH 3 with 1N hydrochloric acid, and was extracted by ethyl acetate. The residue obtained from a concentrated organic layer was washed to dichloromethane/methanol (50/1) and was recrystallized from methanol:water (7:1.5). The present compound (189 mg) having the following physical properties values was obtained.
TLC:Rf 0.46 (dichloromethane: methanol=9:1);
NMR (CDCl$_3$) 8.00-7.94 (m, 2H), 7.42-7.36 (m, 2H), 7.35-7.28 (m, 4H), 6.47 (brs, 1H), 4.76-4.60 (m, 1H), 2.95-2.63 (m, 3H), 2.09-1.77 (m, 3H), 1.49-1.26 (m, 1H).

EXAMPLE 21

1-(4-hydroxymethylphenylcarbamoyl )-2,3,4,5-tetrahydro-1H-1-benzazepine

A mixture of which lithium borohydride (29 mg) had been added to tetrahydrofuran (9 ml) solution of the compound (294 mg) prepared in Example 18 with stirring at room temperature was slowly heated up to 75° C. and was stirred at the same temperature for 3 hours. The reactive mixture to which 1N hydrochloric acid (3 ml) had been added was extracted by ethyl acetate. The residue obtained from a concentrated organic layer was purified by silica gel column chromatography (n-hexane:ethyl acetate=1:1), and was washed by hexane. The present compound (183 mg) having the following physical properties values was obtained.
TLC:Rf 0.22 (n-hexane:ethyl acetate=1:1);
NMR (CDCl$_3$):δ 7.35-7.21 (m, 8H), 6.24 (brs, 1H), 4.79-4.58 (m, 1H), 4.59 (d, J=5.4 Hz, 2H), 2.95-2.58 (m, 3H), 2.11-1.71 (m, 3H), 1.52-1.23 (m, 1H).

EXAMPLE 21(1)

1-[4-(2-hydroxyethyloxy)phenylcarbamoyl]-2,3,4,5-tetrahydro-1H-1-benzazepine

The present compound having the following physical properties values was obtained by operating as well as the method represented by Example 21 using a corresponding compound.
TLC:Rf 0.11 (n-hexane:ethyl acetate=1:1);
NMR (CDCl$_3$):δ 7.34-7.26 (m, 4H), 7.23-7.17 (m, 2H), 6.84-6.78 (m, 2H), 6.09 (brs, 1H), 4.80-4.56 (m, 1H), 4.05-4.01 (m, 2H), 3.96-3.89 (m, 2H), 2.93-2.58 (m, 3H), 2.07-1.74 (m, 3H), 2.01 (t, J=6.0 Hz, 1H), 1.53-1.24 (m, 1H).

EXAMPLE 22

6-hydroxy-1-phenylcarbamoyl-2,3,4,5-tetrahydro-1H-1-benzazepine

A mixture of which tribromoboron (1.0M, 2.5 ml) had been added to methylene chlorid (2 ml) solution of the compound (250 mg) prepared in Example 7(7) at −78° C. was stirred at the same temperature. The reactive mixture to which saturated sodium bicarbonate solution had been added was extracted by ethyl acetate. The organic layer washed with saturated brine was concentrated after drying with sulfuric anhydride sodium. The obtained residue was purified by silica gel column chromatography (n-hexane:ethyl acetate=2:1) and was recrystallized from n-hexane:ethyl acetate. The present compound (23 mg) having the following physical properties values was obtained.
TLC:Rf 0.31 (n-hexane:ethyl acetate=2:1);
NMR (CDCl$_3$+CD$_3$OD):δ 7.31-7.20 (m, 4H), 7.12-7.06 (m, 1H), 7.02-6.96 (m, 1H), 6.85-6.80 (m, 2H), 6.41 (bs, 1H), 4.70-4.45 (m, 1H), 3.42-3.20 (m, 1H), 2.82-2.52 (m, 1H), 2.45-2.27 (m, 1H), 2.10-1.70 (m, 3H), 1.45-1.20 (m, 1H).

EXAMPLE 22(1)-EXAMPLE 22(3)

The present compound having the following physical properties values was obtained by operating as well as the method represented by Example 22 using a corresponding compound instead of the compound prepared in Example 7(7).

EXAMPLE 22(1)

7-hydroxy-1-phenylcarbamoyl-2,3,4,5-tetrahydro-1H-1-benzazepine

TLC:Rf 0.20 (n-hexane:ethyl acetate=3:1);
NMR (CDCl$_3$+CD$_3$OD):δ 7.29-7.20 (m, 4H), 7.11 (d, J=8.4 Hz, 1H), 7.03-6.96 (m, 1H), 6.78 (d, J=2.7 Hz, 1H), 6.73 (dd, J=8.4 Hz, 2.7 Hz, 1H), 6.40 (bs, 1H), 4.63-4.40 (m, 1H), 2.85-2.56 (m, 3H), 2.06-1.72 (m, 3H), 1.46-1.29 (m, 1H).

EXAMPLE 22(2)

7-hydroxy-1-(4-hydroxyphenylcarbamoyl)-2,3,4,5-tetrahydro-1H-1-benzazepine

TLC:Rf 0.44 (methylene chloride: methanol=9:1);
NMR(CD$_3$OD):δ 7.08 (d, J=8.1 Hz, 1H), 7.06-7.01 (m, 2H), 6.74 (d, J=2.7 Hz, 1H), 6.71-6.64 (m, 3H), 4.60-4.38 (m, 1H), 2.83-2.54 (m, 3H), 2.11-1.68 (m, 3H), 1.62-1.22 (m, 1H)

EXAMPLE 22(3)

6-hydroxy-1-(4-hydroxyphenylcarbamoyl)-2,3,4,5-tetrahydro-1H-1-benzazepine

TLC:Rf 0.54 (methylene chloride: methanol=9:1);
NMR (CD$_3$OD):δ 7.08 (t, J=7.5 Hz, 1H), 7.07-7.01 (m, 2H), 6.80 (dd, J=7.5 Hz, 1.2 Hz, 1H), 6.76 (dd, J=7.5 Hz, 1.2 Hz, 1H), 6.69-6.64 (m, 2H), 4.70-4.16 (m, 1H), 2.97-2.12 (m, 3H), 2.01-1.64 (m, 3H), 1.49-1.10 (m, 1H).

EXAMPLE 23

1-(4-dimethylaminophenylcarbamoyl)-2,3,4,5-tetrahydro-1H-1-benzazepine

A mixture of which 35% formaldehyde solution (0.6 ml) and cyano sodium borohydride (130 mg) had been added to acetonitrile (5 ml) solution of the compound (196 mg) prepared in Example 16 with stirring at room temperature was stirred at room temperature for 10 minutes. The solution slowly neutralized with 2N hydrochloric acid was stirred at room temperature for 3 hours. The reactive mixture to which 2N sodium hydroxide solution had been added was extracted by methylene chloride. The organic layer was concentrated after drying with sulfuric anhydride sodium. The obtained residue was purified by silica gel column chromatography (n-hexane:ethyl acetate=5:1, 3:1, and 2:1 gradually), which the oil was obtained. 4N hydrochloric acid-ethyl acetate solution was added to the oil dissolved to diethyl ether (3 ml), and hydrochloride (120 mg) as a target was obtained by filtration of the extracted white crystal. 2N sodium hydroxide solution was added to this hydrochloride, which was converted into a free body. The present compound (68 mg) having the following physical properties values was obtained.
TLC:Rf 0.55 (n-hexane:ethyl acetate=1:1);
NMR (CDCl$_3$):δ 7.33-7.24 (m, 4H), 7.18-7.11 (m, 2H), 6.69-6.63 (m, 2H), 6.00 (brs, 1H), 4.81-4.49 (m, 1H), 3.03-2.58 (m, 9H), 2.11-1.74 (m, 3H), 1.56-1.23 (m, 1H).

EXAMPLE 24

1-[4-(2-nitrophenylsulphonylamino)phenylcarbamoyl]-2,3,4,5-tetrahydro-1H-1-benzazepine A mixture of which triethylamine (0.2 ml) and 2-nitro sulfonyl chloride (441 mg) had been added to tetrahydrofuran (1 ml) solution of the compound (169 mg) prepared in Example 16 was stirred at room temperature for 2 hours. The reactive mixture to which water had been added was extracted by ethyl acetate. The organic layer sequentially washed with 1N hydrochloric acid, saturated sodium bicarbonate solution, and saturated brine was concentrated after drying with sulfuric anhydride magnesium. The obtained residue was purified by silica gel column chromatography (n-hexane:ethyl acetate=3:2 to 2:1). The present compound (237 mg) having the following physical properties values was obtained.
TLC:Rf 0.38 (n-hexane:ethyl acetate=1:1);
NMR (CDCl$_3$):δ 7.83 (dd, J=7.8 Hz, 1.5 Hz, 1H), 7.74 (dd, J=7.8 Hz, 1.5 Hz, 1H), 7.67 (dt, J=1.5 Hz, 7.8 Hz, 1H), 7.54 (dt, J=7.8 Hz, 1.5 Hz, 1H), 7.35-7.16 (m, 6H), 7.14 (bs, 1H), 7.07-7.00 (m, 2H), 6.21 (bs, 1H), 4.74-4.53 (m, 1H), 2.90-2.55 (m, 3H), 2.07-1.73 (m, 3H), 1.48-1.20 (m, 1H).

EXAMPLE 25

1-[4-(N-methyl-N-2-nitrophenylsulphonylamino)phenylcarbamoyl]-2,3,4,5-tetrahydro-1H-1-benzazepine A mixture of which potassium carbonate (82 mg) and methyl iodide (37 μl) had been added to N, N-dimethylformamide (1 ml) solution of the compound (230 mg) prepared in Example 24 was stirred at room temperature over night. The reactive mixture to which water had been added was extracted by ethyl acetate. The organic layer washed with saturated brine was concentrated after drying with sulfuric anhydride magnesium. The obtained residue was purified by silica gel column chromatography (n-hexane:ethyl acetate=3:2 to 2:1). The present compound (231 mg) having the following physical properties values was obtained.
TLC:Rf 0.40 (n-hexane:ethyl acetate=1:1);
NMR (CDCl$_3$):δ 7.68-7.61 (m, 1H), 7.60-7.55 (m, 1H), 7.52-7.45 (m, 2H), 7.36-7.24 (m, 6H), 7.10-7.04 (m, 2H), 6.29 (bs, 1H), 4.73-4.58 (m, 1H), 3.33 (s, 3H), 2.90-2.60 (m, 3H), 2.10-1.73 (m, 3H), 1.50-1.20 (m, 1H).

EXAMPLE 26

1-(4-methylaminophenylcarbamoyl)-2,3,4,5-tetrahydro-1H-1-benzazepine

A mixture of which 2-mercaptoacetic acid (61 μl) and lithium hydroxide monohydrate (74 mg) had been added to N, N-dimethylformamide (2 ml) solution of the compound (211 mg) prepared in Example 25 was stirred at room temperature for 3 hours. The reactive mixture to which water had been added was extracted by ethyl acetate. The organic layer sequentially washed with saturated sodium bicarbonate solution and saturated brine was concentrated after drying with sulfuric anhydride magnesium. The obtained residue was recrystallized from n-hexane:ethyl acetate. The present compound (83 mg) having the following physical properties values was obtained.

TLC:Rf 0.33 (n-hexane:ethyl acetate=1:1);

NMR (CDCl$_3$):δ 7.33-7.24 (m, 4H), 7.13-7.06 (m, 2H), 6.55-6.49 (m, 2H), 5.98 (bs, 1H), 4.78-4.55 (m, 1H), 3.65-3.42 (m, 1H), 2.93-2.50 (m, 6H), 2.12-1.73 (m, 3H), 1.50-1.20 (m, 1H).

EXAMPLE 27

A mixture of which anisole (1.8 ml) and methanesulfonyl chloride (1.1 ml) had been added to toluene (5 ml) solution of the compound (629 mg) prepared in Example 12(7) was stirred at room temperature for 30 minutes. The reactive mixture to which water had been added was extracted by ethyl acetate. The organic layer sequentially washed with saturated sodium bicarbonate solution and saturated brine was concentrated after drying with sulfuric anhydride magnesium. The obtained residue was purified by silica gel column chromatography (n-hexane:ethyl acetate=3:2). The present compound (Example 27(a): 295 mg and Examples 27(b): 87 mg) having the following physical properties values was obtained.

EXAMPLE 27(a)

4-(4-hydroxyphenylcarbamoyl)-5, 6, 7, 8-tetrahydro-4H-thieno[2,3-f]azepine

TLC:Rf 0.38 (n-hexane:ethyl acetate=1:1);

NMR (CDCl$_3$):δ 7.14-7.04 (m, 3H), 6.97 (d, J=5.1 Hz, 1H), 6.72-6.65 (m, 2H), 6.35 (bs, 1H), 5.77 (s, 1H), 4.00-3.35 (b, 2H), 2.90-2.80 (m, 2H), 1.99-1.89 (m, 2H), 1.78-1.60 (m, 2H).

EXAMPLE 27(b)

4-(3-benzyl-4-hydroxyphenylcarbamoyl)-5, 6, 7, 8-tetrahydro-4H-thieno[2,3-f]azepine TLC:Rf 0.58 (n-hexane:ethyl acetate=1:1);

NMR (CDCl$_3$):δ 7.30-7.10 (m, 5H), 7.10-7.02 (m, 3H), 6.96 (d, J=5.4 Hz, 1H), 6.66 (d, J=8.4 Hz, 1H), 6.32 (bs, 1H), 5.05 (s, 1H), 4.0-3.4 (b, 2H), 3.93 (s, 2H), 2.88-2.80 (m, 2H), 1.98-1.88 (m, 2H), 1.76-1.63 (m, 2H).

EXAMPLE 27(1)

1-(4-hydroxy-2-nitrophenylcarbamoyl)-2,3,4,5-tetrahydro-1H-1-benzazepine

A present compound having the following physical properties values was obtained by operating as well as the method represented in Example 27, using the corresponding compound instead of the compound prepared in Example 12(7).

TLC:Rf 0.37 (n-hexane:ethyl acetate=3:2);

NMR (CDCl$_3$):δ 9.18 (bs, 1H), 8.35 (d, J=9.3 Hz, 1H), 7.51 (d, J=3.0 Hz, 1H), 7.38-7.28 (m, 4H), 7.09 (dd, J=9.3 Hz, 3.0 Hz, 1H), 6.70-6.58 (m, 1H), 4.67-4.52 (m, 1H), 2.93-2.67 (m, 3H), 2.10-1.85 (m, 3H), 1.50-1.30 (m, 1H).

EXAMPLE 28(1)-EXAMPLE 28 (15)

Compounds of the present invention having the following physical properties values were obtained by operating as well as the method represented in Example 12, using the corresponding compound.

EXAMPLE 28(1)

N-(4-methoxymethoxyphenyl)-7-methyl-2,3,4,5-tetrahydro-1H-1-benzazepine-1-carboxamide TLC: Rf 0.24 (n-hexane:ethyl acetate=4:1);

NMR(CDCl$_3$):δ 7.23-7.06 (m, 5H), 6.94-6.89 (m, 2H), 6.13 (s, 1H), 5.10 (s, 2H), 4.76-4.57 (br, 1H), 3.45 (s, 3H), 2.92-2.52 (br, 3H), 2.37 (s, 3H), 2.10-1.70 (br, 3H), 1.50-1.21 (br, 1H).

EXAMPLE 28(2)

N-(4-benzyloxyphenyl)-5-(t-butyldimethylsilyloxy)-2,3,4,5-tetrahydro-1H-1-benzazepine-1-carboxamide TLC:Rf 0.43 (n-hexane: Ethyl acetate=3:1).

EXAMPLE 28(3)

N-(4-benzyloxyphenyl)-8-fluoro-2,3,4,5-tetrahydro-1H-1-benzazepine-1-carboxamide TLC:Rf 0.25 (n-hexane:ethyl acetate=3:1);

NMR(CDCl$_3$):δ 7.44-7.25 (m, 6H), 7.24-7.17 (m, 2H), 7.07-6.95 (m, 2H), 6.91-6.84 (m, 2H), 6.04 (brs, 1H), 5.02 (s, 2H), 4.90-4.29 (m, 1H), 2.97-2.41 (m, 3H), 2.19-1.70 (m, 3H), 1.65-1.19 (m, 1H).

EXAMPLE 28(4)

N-(4-benzyloxyphenyl)-9-methyl-2,3,4,5-tetrahydro-1H-1-benzazepine-1-carboxamide TLC:Rf 0.30 (n-hexane:ethyl acetate=4:1);

NMR(CDCl$_3$):δ7.42-7.27 (m, 5H), 7.21-7.12 (m, 5H), 6.88-6.83 (m, 2H), 5.91 (s, 1H), 5.01 (s, 2H), 4.65 (m, 1H), 2.87 (m, 1H), 2.73-2.57 (m, 2H), 2.28 (s, 3H), 2.14-1.96 (m, 2H), 1.77 (m, 1H), 1.35 (m, 1H).

EXAMPLE 28(5)

N-(4-benzyloxyphenyl)-6-methyl-2,3,4,5-tetrahydro-1H-1-benzazepine-1-carboxamide TLC:Rf 0.28 (n-hexane:ethyl acetate=4:1);

NMR(CDCl$_3$):δ 7.42-7.27 (m, 5H), 7.23-7.12 (m, 5H), 6.88-6.83 (m, 2H), 6.12 (s, 1H), 5.01 (s, 2H), 4.61 (d, J=13.8 Hz, 1H), 2.99 (dd, J=13.8, 6.0 Hz, 1H), 2.76-2.56 (m, 2H), 2.39 (s, 3H), 2.08-1.96 (m, 2H), 1.74 (m, 1H), 1.30 (m, 1H).

EXAMPLE 28(6)

7-nitro-N-(4-methoxymethoxyphenyl)-2,3,4,5-tetrahydro-1H-1-benzazepine-1-carboxamide TLC:Rf 0.45 (n-hexane:ethyl acetate=1:1);

NMR(CDCl$_3$):δ 8.20 (d, J=2.4 Hz, 1H), 8.15 (dd, J=8.1, 2.4 Hz, 1H), 7.51 (d, J=8.1 Hz, 1H), 7.22-7.16 (m, 2H), 6.98-6.92 (m, 2H), 5.95 (brs, 1H), 5.12 (s, 2H), 3.45 (s, 3H), 2.96-2.89 (m, 3H), 1.99-1.80 (m, 4H).

EXAMPLE 28(7)

7-benzyloxy-N-(4-benzyloxyphenyl)-2,3,4,5-tetrahydro-1H-1-benzazepine-1-carboxamide TLC:Rf 0.18 (n-hexane:ethyl acetate=4:1);
NMR(CDCl$_3$):δ 1.37 (m, 1H), 1.91 (m, 3H), 2.73 (m, 3H), 4.64 (d, J=15.11 Hz, 1H), 5.01 (s, 2H), 5.08 (s, 2H), 6.11 (s, 1H), 6.87 (m, 4H), 7.20 (m, 3H), 7.36 (m, 10H)

EXAMPLE 28(8)

7-benzyloxy-N-(2-methoxy-4-methoxymethoxyphenyl)-2,3,4,5-tetrahydro-1H-1-benzazepine-1-carboxamide TLC:Rf 0.23 (n-hexane:ethyl acetate=3:1);
NMR(CDCl$_3$):δ 1.39 (m, 1H), 1.88 (m, 3H), 2.75 (m, 3H), 3.46 (s, 3H), 3.57 (s, 3H), 4.64 (d, J=12.36 Hz, 1H), 5.10 (s, 4H), 6.48 (d, J=2.75 Hz, 1H), 6.61 (dd, J=8.79, 2.75 Hz, 1H), 6.75 (s, 1H), 6.85 (dd, J=8.65, 2.88 Hz, 1H), 6.93 (d, J=2.75 Hz, 1H), 7.21 (d, J=8.52 Hz, 1H), 7.41 (m, 5H), 8.05 (d, J=8.79 Hz, 1H).

EXAMPLE 28(9)

N-(4-benzyloxyphenyl)-5-(t-butyldimethylsilyloxy)-2,3,4,5-tetrahydro-1H-1-benzazepine-1-carboxamide TLC:Rf 0.43 (n-hexane:ethyl acetate=3:1);
NMR(CDCl$_3$):δ 7.78-7.70 (m, 1H), 7.46-7.25 (m, 8H), 7.22-7.11 (m, 2H), 6.91-6.82 (m, 2H), 6.06 (brs, 1H), 5.01 (s, 2H), 4.89-4.81 (m, 1H), 4.62-4.50 (m, 1H), 2.70-2.57 (m, 1H), 2.16-1.98 (m, 2H), 1.74-1.47 (m, 2H), 0.91 (s, 9H), 0.07 (s, 6H).

EXAMPLE 28(10)

N-(4-benzyloxyphenyl)-7-fluoro-2,3,4,5-tetrahydro-1H-1-benzazepine-1-carboxamide TLC:Rf 0.29 (n-hexane:ethyl acetate=3:1);
NMR(CDCl$_3$):δ 1.36 (m, 1H), 1.91 (m, 3H), 2.72 (m, 3H), 4.67 (m, 1H), 5.01 (s, 2H), 6.01 (s, 1H), 6.87 (m, 2H), 6.96 (td, J=8.24, 3.02 Hz, 1H), 7.03 (dd, J=8.93, 2.88 Hz, 1H), 7.19 (m, 2H), 7.34 (m, 6H).

EXAMPLE 28(11)

N-(4-methoxymethoxyphenyl)-5-methyl-2,3-dihydro-1H-1-benzazepine-1-carboxamide

TLC:Rf 0.36 (n-hexane:ethyl acetate=2:1).

EXAMPLE 28(12)

N-(4-benzyloxyphenyl)-6-fluoro-2,3,4,5-tetrahydro-1H-1-benzazepine-1-carboxamide TLC:Rf 0.35 (n-hexane:ethyl acetate=4:1);
NMR(CDCl$_3$):δ 1.34 (m, 1H), 1.95 (m, 3H), 2.85 (m, 3H), 4.65 (m, 1H), 6.27 (s, 1H), 7.30 (m, 5H), 8.00 (m, 2H)

EXAMPLE 28(13)

7-benzyloxy-N-(3-fluoro-4-methoxymethoxyphenyl)-2,3,4,5-tetrahydro-1H-1-benzazepine-1-carboxamide TLC:Rf 0.38 (n-hexane:ethyl acetate=2:1);
NMR(CDCl$_3$):δ 1.36 (m, 1H), 1.92 (m, 3H), 2.72 (m, 3H), 3.49 (s, 3H), 4.63 (d, J=13.46 Hz, 1H), 5.09 (s, 2H), 5.12 (s, 2H), 6.17 (s, 1H), 6.79 (m, 1H), 6.86 (dd, J=8.52, 2.75 Hz, 1H), 6.93 (d, J=3.02 Hz, 1H), 7.02 (t, J=8.93 Hz, 1H), 7.18 (d, J=8.52 Hz, 1H), 7.38 (m, 6H).

EXAMPLE 28(14)

N-(2-chloropyridin-5-yl)-2,3,4,5-tetrahydro-1H-1-benzazepine-1-carboxamide

TLC: Rf 0.15 (n-hexane:ethyl acetate=5:1);
NMR(CDCl$_3$):δ 1.39 (m, 1H), 1.95 (m, 3H), 2.77 (m, 3H), 4.67 (m, 1H), 6.05 (s, 1H), 6.74 (d, J=9.07 Hz, 1H), 7.32 (m, 7H), 7.42 (m, 2H), 7.77 (dd, J=8.93, 2.88 Hz, 1H), 7.89 (d, J=2.20 Hz, 1H).

EXAMPLE 28(15)

N-(4-benzyloxyphenyl)-2,3-dihydrospiro[1-benzazepine-4,2'-[1,3]dioxolane]-1(5H)-carboxamide TLC:Rf 0.35 (n-hexane:ethyl acetate=1:1);
NMR(CDCl$_3$):δ 1.82 (m, 1H), 2.34 (m, 1H), 3.04 (m, 3H), 3.94 (m, 4H), 4.59 (m, 1H), 5.02 (s, 2H), 6.17 (s, 1H), 6.87 (m, 2H), 7.20 (m, 2H), 7.35 (m, 9H).

EXAMPLE 29(1)-EXAMPLE 29 (26)

Compounds of the present invention having the following physical properties values were obtained by operating as well as the method represented in Example 1, using the corresponding compound.

EXAMPLE 29(1)

N-phenyl-6-methyl-2,3,4,5-tetrahydro-1H-1-benzazepine-1-carboxamide

TLC:Rf 0.46 (n-hexane:ethyl acetate=4:1);
NMR(CDCl$_3$):δ 7.32-7.11 (m, 7H), 6.97 (m, 1H), 6.26 (s, 1H), 4.63 (d, J=14.1 Hz, 1H), 3.00 (dd, J=14.1, 6.0 Hz, 1H), 2.77-2.56 (m, 2H), 2.39 (s, 3H), 2.09-1.95 (m, 2H), 1.75 (m, 1H), 1.30 (m, 1H).

EXAMPLE 29(2)

7-fluoro-N-phenyl-2,3,4,5-tetrahydro-1H-1-benzazepine-1-carboxamide

TLC:Rf 0.32 (n-hexane:ethyl acetate=5:1);
NMR(CDCl$_3$):δ 1.40 (m, 1H), 1.92 (m, 3H), 2.72 (m, 3H), 4.66 (s, 1H), 6.15 (s, 1H), 7.00 (m, 3H), 7.28 (m, 5H).

EXAMPLE 29(3)

6-fluoro-N-phenyl-2,3,4,5-tetrahydro-1H-1-benzazepine-1-carboxamide

TLC:Rf 0.41 (n-hexane:ethyl acetate=4:1);
NMR(CDCl$_3$):δ 1.34 (m, 1H), 1.95 (m, 3H), 2.59 (m, 2H), 3.23 (m, 1H), 4.70 (m, 1H), 6.22 (s, 1H), 7.04 (m, 3H), 7.27 (m, 5H).

EXAMPLE 29(4)

7-nitro-N-phenyl-2,3,4,5-tetrahydro-1H-1-benzazepine-1-carboxamide

TLC:Rf 0.42 (ethyl acetate: n-hexane=1:2);
NMR (CDCl$_3$):δ 1.75 (s, 2H), 1.91 (m, 2H), 2.93 (m, 2H), 3.72 (m, 2H), 6.07 (s, 1H), 7.04 (m, 1H), 7.29 (m, 4H), 7.49 (d, J=8.52 Hz, 1H), 8.16 (dd, J=8.52, 2.75 Hz, 1H), 8.23 (d, J=2.47 Hz, 1H).

EXAMPLE 29(5)

8-fluoro-N-(4-fluorobenzyl)-2,3,4,5-tetrahydro-1H-1-benzazepine-1-carboxamide

TLC:Rf 0.29 (n-hexane:ethyl acetate=3:1);
NMR (DMSO-d$_6$):δ 1.58 (m, 2H), 1.72 (m, 2H), 2.67 (m, 2H), 3.50 (m, 2H), 4.22 (d, J=5.77 Hz, 2H), 6.07 (m, 1H), 6.99 (m, 4H), 7.27 (m, 3H).

EXAMPLE 29(6)

N-benzyl-8-fluoro-2,3,4,5-tetrahydro-1H-1-benzazepine-1-carboxamide

TLC:Rf 0.74 (n-hexane:ethyl acetate=2:1);
NMR (DMSO-d$_6$):δ 1.59 (m, 2H), 1.73 (m, 2H), 2.69 (m, 2H), 3.52 (m, 2H), 4.26 (d, J=5.77 Hz, 2H), 6.06 (m, 1H), 6.98 (m, 2H), 7.24 (m, 6H).

EXAMPLE 29(7)

N-benzyl-7-fluoro-2,3,4,5-tetrahydro-1H-1-benzazepine-1-carboxamide

TLC:Rf 0.29 (n-hexane:ethyl acetate=2:1);
NMR (DMSO-d$_6$):δ 1.58 (m, 2H), 1.72 (m, 2H), 2.69 (m, 2H), 3.48 (m, 2H), 4.22 (d, J=6.04 Hz, 2H), 5.90 (m, 1H), 6.99 (td, J=8.52, 3.02 Hz, 1H), 7.09 (dd, J=9.48, 3.16 Hz, 1H), 7.24 (m, 6H).

EXAMPLE 29(8)

7-fluoro-N-(4-fluorobenzyl)-2,3,4,5-tetrahydro-1H-1-benzazepine-1-carboxamide

TLC:Rf 0.23 (n-hexane: Ethyl acetate=2:1);
NMR (DMSO-d$_6$):δ 1.61 (m, 2H), 1.71 (m, 2H), 2.67 (m, 2H), 3.47 (m, 2H), 4.19 (d, J=6.32 Hz, 2H), 5.96 (m, 1H), 7.11 (m, 7H).

EXAMPLE 29(9)

N-(1-benzylpiperidin-4-yl)-2,3,4,5-tetrahydro-1H-1-benzazepine-1-carboxamide

TLC:Rf 0.33 (dichloromethane: methanol=19:1);
NMR (CDCl$_3$):δ 1.25 (m, 3H), 2.04 (m, 7H), 2.69 (m, 5H), 3.43 (s, 2H), 3.68 (m, 1H), 4.08 (d, J=8.24 Hz, 1H), 4.57 (m, 1H), 7.21 (m, 9H).

EXAMPLE 29(10)

7-fluoro-N-[4-(trifluoromethyl)phenyl]-2,3,4,5-tetrahydro-1H-1-benzazepine-1-carboxamide TLC: Rf 0.61 (n-hexane:ethyl acetate=2:1);
NMR (CDCl$_3$):δ 1.44 (m, 1H), 1.98 (m, 3H), 2.76 (m, 3H), 4.64 (m, 1H), 6.32 (m, 1H), 7.00 (td, J=8.24, 3.02 Hz, 1H), 7.06 (dd, J=8.93, 2.88 Hz, 1H), 7.27 (dd, J=8.52, 5.22 Hz, 1H), 7.45 (m, 4H).

EXAMPLE 29(11)

7-fluoro-N-[4-(fluoromethoxy)phenyl]-2,3,4,5-tetrahydro-1H-1-benzazepine-1-carboxamide TLC:Rf 0.73 (n-hexane:ethyl acetate=2:1);
NMR (CDCl$_3$):δ 1.40 (m, 1H), 1.93 (m, 3H), 2.73 (m, 3H), 4.64 (m, 1H), 6.18 (s, 1H), 6.99 (td, J=8.24, 3.02 Hz, 1H), 7.05 (dd, J=8.79, 3.02 Hz, 1H), 7.10 (m, 2H), 7.27 (dd, J=8.93, 4.81 Hz, 1H), 7.32 (m, 2H).

EXAMPLE 29(12)

N-[4-(difluoromethoxy)phenyl]-7-fluoro-2,3,4,5-tetrahydro-1H-1-benzazepine-1-carboxamide TLC:Rf 0.55 (n-hexane:ethyl acetate=2:1);
NMR (CDCl$_3$):δ 1.39 (m, 1H), 1.95 (m, 3H), 2.78 (m, 3H), 4.64 (m, 1H), 6.14 (m, 1H), 6.41 (t, J=74.31 Hz, 1H), 7.01 (m, 4H), 7.28 (m, 3H).

EXAMPLE 29(13)

N-[4-(dimethylamino)phenyl]-7-fluoro-2,3,4,5-tetrahydro-1H-1-benzazepine-1-carboxamide TLC:Rf 0.50 (n-hexane:ethyl acetate=1:1);
NMR(CDCl$_3$):δ 1.45 (m, 1H), 2.01 (m, 3H), 2.83 (m, 3H), 2.87 (s, 6H), 4.66 (m, 1H), 5.93 (m, 1H), 6.66 (m, 2H), 6.96 (td, J=8.24, 3.02 Hz, 1H), 7.02 (dd, J=8.79, 3.02 Hz, 1H), 7.14 (m, 2H), 7.28 (dd, J=8.52, 5.22 Hz, 1H).

EXAMPLE 29(14)

9-bromo-7-methyl-N-phenyl-2,3,4,5-tetrahydro-1H-1-benzazepine-1-carboxamide

TLC: Rf 0.49 (n-hexane:ethyl acetate=3:1);
NMR(CDCl$_3$):δ7.38 (m, 1H), 7.33-7.20 (m, 4H), 7.06 (m, 1H), 7.00 (m, 1H), 6.01 (s, 1H), 4.63 (m, 1H), 2.89 (m, 1H), 2.73-2.57 (m, 2H), 2.36 (s, 3H), 2.13-1.97 (m, 2H), 1.78 (m, 1H), 1.32 (m, 1H).

EXAMPLE 29(15)

7-methyl-N-(4-nitrophenyl)-2,3,4,5-tetrahydro-1H-1-benzazepine-1-carboxamide

TLC:Rf 0.35 (n-hexane:ethyl acetate=4:1);
NMR(CDCl$_3$):δ1.39 (m, 1H), 1.93 (m, 3H), 2.39 (s, 3H), 2.76 (m, 3H), 4.66 (d, J=13.46 Hz, 1H), 6.63 (s, 1H), 7.13 (m, 3H), 7.46 (m, 2H), 8.11 (m, 2H).

EXAMPLE 29(16)

7-methoxy-N-(4-nitrophenyl)-2,3,4,5-tetrahydro-1H-1-benzazepine-1-carboxamide

TLC:Rf 0.19 (n-hexane:ethyl acetate=4:1);
NMR(CDCl$_3$):δ1.39 (m, 1H), 1.94 (m, 3H), 2.74 (m, 3H), 3.86 (s, 3H), 4.64 (m, 1H), 6.63 (s, 1H), 6.82 (m, 1H), 6.87 (d, J=2.75 Hz, 1H), 7.20 (d, J=8.24 Hz, 1H), 7.47 (m, 2H), 8.12 (m, 2H).

EXAMPLE 29(17)

7-benzyloxy-N-(4-nitrophenyl)-2,3,4,5-tetrahydro-1H-1-benzazepine-1-carboxamide

TLC:Rf 0.49 (n-hexane:ethyl acetate=2:1);
NMR(CDCl$_3$):δ1.39 (m, 1H), 1.94 (m, 3H), 2.74 (m, 3H), 4.64 (d, J=13.46 Hz, 1H), 5.10 (s, 2H), 6.63 (s, 1H), 6.89 (dd, J=8.52, 3.02 Hz, 1H), 6.96 (d, J=3.02 Hz, 1H), 7.20 (d, J=8.52 Hz, 1H), 7.41 (m, 7H), 8.12 (m, 2H).

EXAMPLE 29(18)

N-benzyl-7-benzyloxy-2,3,4,5-tetrahydro-1H-1-benzazepine-1-carboxamide

TLC:Rf 0.39 (n-hexane:ethyl acetate=1:1);
NMR(CDCl$_3$):δ 1.26 (m, 1H), 1.79 (m, 1H), 2.01 (m, 2H), 2.70 (m, 3H), 4.39 (m, 2H), 4.63 (m, 2H), 5.03 (s, 2H), 6.78 (dd, J=8.65, 2.88 Hz, 1H), 6.86 (d, J=2.75 Hz, 1H), 7.12 (d, J=8.52 Hz, 1H), 7.32 (m, 10H)

EXAMPLE 29(19)

7-benzyloxy-N-(4-fluorobenzyl)-2,3,4,5-tetrahydro-1H-1-benzazepine-1-carboxamide TLC:Rf 0.44 (n-hexane:ethyl acetate=1:1);
NMR(CDCl$_3$):δ1.30 (m, 1H), 1.78 (m, 1H), 2.01 (m, 2H), 2.59 (m, 3H), 4.34 (m, 2H), 4.62 (m, 2H), 5.03 (s, 2H), 6.78 (dd, J=8.52, 3.02 Hz, 1H), 6.87 (d, J=2.75 Hz, 1H), 7.16 (m, 10H).

EXAMPLE 29(20)

N-phenyl-2,3,4,5-tetrahydro-1H-1-benzazepine-1-carbothioamide

TLC:Rf 0.46 (n-hexane:ethyl acetate=3:1);
NMR(CDCl$_3$):δ 1.41 (m, 1H), 1.84 (m, 1H), 2.05 (m, 1H), 2.34 (m, 1H), 2.80 (m, 2H), 3.04 (m, 1H), 5.44 (m, 1H), 6.94 (m, 1H), 7.28 (m, 9H).

EXAMPLE 29(21)

N-methyl-2,3,4,5-tetrahydro-1H-1-benzazepine-1-carbothioamide

TLC:Rf 0.38 (n-hexane:ethyl acetate=3:1);
NMR(CDCl$_3$):δ 1.38 (m, 1H), 1.79 (m, 1H), 2.00 (m, 1H), 2.27 (m, 1H), 2.67 (m, 2H), 2.93 (m, 1H), 3.05 (d, J=4.58 Hz, 3H), 5.35 (m, 2H), 7.17 (m, 1H), 7.28 (m, 3H).

EXAMPLE 29(22)

N-(4-chlorobenzyl)-2,3,4,5-tetrahydro-1H-1-benzazepine-1-carbothioamide

TLC:Rf 0.53 (n-hexane:ethyl acetate=3:1);
NMR(CDCl$_3$):δ 1.40 (m, 1H), 1.82 (m, 1H), 2.03 (m, 1H), 2.30 (m, 1H), 2.70 (m, 2H), 2.98 (m, 1H), 4.81 (m, 2H), 5.38 (m, 1H), 5.62 (m, 1H), 7.23 (m, 8H).

EXAMPLE 29(23)

N-(4-methoxybenzyl)-2,3,4,5-tetrahydro-1H-1-benzazepine-1-carbothioamide

TLC:Rf 0.36 (n-hexane:ethyl acetate=3:1);
NMR(CDCl$_3$):δ 1.40 (m, 1H), 1.82 (m, 1H), 2.05 (m, 1H), 2.28 (m, 1H), 2.70 (m, 2H), 2.97 (m, 1H), 3.77 (s, 3H), 4.76 (m, 2H), 5.38 (m, 1H), 5.56 (m, 1H), 6.81 (m, 2H), 7.21 (m, 6H).

EXAMPLE 29(24)

N-(2-benzyloxypyridin-5-yl)-2,3,4,5-tetrahydro-1H-1-benzazepine-1-carboxamide

TLC:Rf 0.16 (n-hexane:ethyl acetate=4:1);
NMR(CDCl$_3$):δ 1.39 (m, 1H), 1.95 (m, 3H), 2.77 (m, 3H), 4.67 (m, 1H), 5.31 (s, 2H), 6.05 (s, 1H), 6.74 (d, J=9.07 Hz, 1H), 7.32 (m, 7H), 7.42 (m, 2H), 7.77 (dd, J=8.93, 2.88 Hz, 1H), 7.89 (d, J=2.20 Hz, 1H)

EXAMPLE 29(25)

4-(2,3,4,5-tetrahydro-1H-1-benzazepin-1-ylcarbonylaminomethyl)phenoxyacetic acid methyl ester TLC:Rf 0.31 (n-hexane:ethyl acetate=1:1);
NMR(CDCl$_3$):δ 1.63 (s, 1H), 1.97 (m, 3H), 2.64 (m, 4H), 3.78 (m, 3H), 4.34 (m, 2H), 4.55 (m, 1H), 4.60 (s, 2H), 6.82 (m, 2H), 7.20 (m, 6H).

EXAMPLE 29(26)

N-(1-methyl-2-oxo-12-dihydropyridin-5-yl)-2,3,4,5-tetrahydro-1H-1-benzazepine-1-carboxamide TLC:Rf 0.34 (methanol: ethyl acetate=1:9).

EXAMPLE 30

7-methoxy-N-(4-methylaminophenyl)-2,3,4,5-tetrahydro-1H-1-benzazepine-1-carboxamide A present compound having the following physical properties values was obtained by operating as well as the method sequentially represented in Examples 24, 25, and 26, using a corresponding compound.

TLC:Rf 0.15 (n-hexane:ethyl acetate=1:1);
NMR (CDCl₃):δ 7.21 (d, J=8.7 Hz, 1H), 7.13-7.08 (m, 2H), 6.83 (d, J=3.0 Hz, 1H), 6.77 (dd, J=8.7, 3.0 Hz, 1H), 6.55-6.49 (m, 2H), 6.01 (s, 1H), 4.64 (m, 1H), 3.83 (s, 3H), 3.70-3.35 (br, 1H), 2.87-2.59 (m, 6H), 2.10-1.70 (br, 3H), 1.35 (m, 1H).

EXAMPLE 31(1)-EXAMPLE 31(2)

Compounds of the present invention having the following physical properties values were obtained by operating as well as the method represented in Example 15, using the corresponding compound instead of the compound prepared in Example 12(5).

EXAMPLE 31(1)

N-(4-hydroxyphenyl)-7-nitro-2,3,4,5-tetrahydro-1H-1-benzazepine-1-carboxamide

TLC:Rf 0.30 (ethyl acetate: n-hexane=1:1);
NMR (DMSO-d₆):δ 1.67 (m, 4H), 2.87 (m, 2H), 3.60 (m, 2H), 6.61 (m, 2H), 7.13 (m, 2H), 7.42 (d, J=8.79 Hz, 1H), 7.96 (s, 1H), 8.05 (dd, J=8.65, 2.88 Hz, 1H), 8.23 (d, J=2.75 Hz, 1H), 9.04 (s, 1H).

EXAMPLE 31(2)

N-(4-hydroxyphenyl)-2,3-dihydro-1H-1-benzazepine-1-carboxamide

TLC:Rf 0.35 (ethyl acetate: n-hexane=1:1);
NMR (CD₃OD):δ 2.63 (m, 2H), 3.74 (m, 2H), 6.03 (dt, J=12.09, 4.12 Hz, 1H), 6.48 (dt, J=12.29, 2.09 Hz, 1H), 6.67 (m, 2H), 7.07 (m, 2H), 7.31 (m, 4H)

REFERENCE EXAMPLE 21

2,3,4,5-tetrahydro-1H-1-benzazepine-1-carbonyl chloride

A mixture of which tetrahydrofuran (60 ml) solution of 2,3,4,5-tetrahydro 1H-1-benzazepine (5.89 g) and pyridine (9.7 ml) had been dropped to tetrahydrofuran (60 ml) solution of triphosgene (5.93 g) during storage in ice was stirred at room temperature for 2 hours. The reactive mixture to which 1N hydrochloric acid had been added was extracted by ethyl acetate. The organic layer washed with saturated brine was concentrated after drying with sulfuric anhydride magnesium. The obtained residue was recrystallized by a mixture solvent containing n-hexane:ethyl acetate=9:1. A title compound (6.77 g) having the following physical properties values was obtained.

TLC:Rf (n-hexane:ethyl acetate=9:1);
NMR(CDCl₃):δ 1.40 (m, 1H), 1.84 (m, 1H), 2.06 (m, 2H), 2.83 (m, 3H), 4.46 (m, 1H), 7.26 (m, 4H).

EXAMPLE 32

N-(4-fluorobenzyl)-2,3,4,5-tetrahydro-1H-1-benzazepine-1-carboxamide

A mixture of which 4-fluorobenzyl amine (196 mg) had been added to tetrahydrofuran (2.5 ml) solution of the compound (108 mg) prepared in reference example 21 was stirred at room temperature for 1 hour. The reactive mixture to which 1N hydrochloric acid had been added was extracted by ethyl acetate. The organic layer washed with saturated brine was concentrated after drying with sulfuric anhydride magnesium. The obtained residue was purified by silica gel column chromatography (n-hexane:ethyl acetate=2:1). The present compound (152 mg) having the following physical properties values was obtained.

TLC:Rf 0.29 (n-hexane:ethyl acetate=2:1);
NMR (CDCl₃):δ7.28-7.15 (m, 6H), 7.01-6.93 (m, 2H), 4.78-4.50 (br, 2H), 4.34 (bs, 2H), 2.85-2.50 (br, 3H), 2.10-1.70 (br, 3H), 1.50-1.15 (br, 1H).

EXAMPLE 31(1)-EXAMPLE 31(2)

Compounds of the present invention having the following physical properties values were obtained by operating as well as the method represented in Example 32, using the corresponding compound.

EXAMPLE 32(1)

N-(4-methoxybenzyl)-2,3,4,5-tetrahydro-1H-1-benzazepine-1-carboxamide

TLC:Rf 0.23 (n-hexane:ethyl acetate=2:1);
NMR (CDCl₃):δ 7.25-7.12 (m, 6H), 6.84-6.79 (m, 2H), 4.80-4.52 (br, 2H), 4.32 (bs, 2H), 3.77 (s, 3H), 2.90-2.55 (br, 3H), 2.15-1.70 (br, 3H), 1.50-1.20 (br, 1H).

EXAMPLE 32(2)

N-[2-[ethyl(3-methylphenyl)amino]ethyl]-2,3,4,5-tetrahydro-1H-1-benzazepine-1-carboxamide TLC: Rf 0.41 (n-hexane:ethyl acetate=2:1);
NMR (CDCl₃):δ 7.25-7.04 (m, 5H), 6.50-6.46 (m, 3H), 4.75-4.40 (br, 2H), 3.35-3.24 (m, 6H), 2.80-2.50 (br, 3H), 2.27 (s, 3H), 2.10-1.70 (br, 3H), 1.46-1.20 (br, 1H), 1.06 (t, J=7.2 Hz, 3H).

EXAMPLE 32(3)

N-cycloheptyl-2,3,4,5-tetrahydro-1H-1-benzazepine-1-carboxamide

TLC:Rf 0.32 (n-hexane:ethyl acetate=3:1);
NMR (CDCl₃):δ 7.28-7.16 (m, 4H), 4.85-4.35 (br, 1H), 4.15 (d, J=7.8 Hz, 1H), 3.83 (m,1H), 2.84-2.40 (br, 3H), 2.10-1.70 (br, 5H), 1.56-1.26 (m, 11H).

EXAMPLE 32(4)

N-cyclooctyl-2,3,4,5-tetrahydro-1H-1-benzazepine-1-carboxamide

TLC:Rf 0.35 (n-hexane:ethyl acetate=3:1);
NMR (CDCl₃):δ 7.28-7.15 (m, 4H), 4.80-4.40 (br, 1H), 4.15 (d, J=8.1 Hz, 1H), 3.87 (m, 1H), 2.85-2.40 (br, 3H), 2.06-1.68 (br, 6H), 1.60-1.24 (br, 12H).

EXAMPLE 32(5)

N-(4-t-butylbenzyl)-2,3,4,5-tetrahydro-1H-1-benzazepine-1-carboxamide

TLC:Rf 0.45 (n-hexane:ethyl acetate=2:1);
NMR (CDCl$_3$):δ 7.33-7.29 (m, 2H), 7.25-7.12 (m, 6H), 4.80-4.50 (br, 2H), 4.37 (d, J=5.7 Hz, 2H), 2.90-2.50 (br, 3H), 2.15-1.70 (br, 3H), 1.36-1.22 (m, 10H).

EXAMPLE 32(6)

N-(4-hydroxybutyl)-2,3,4,5-tetrahydro-1H-1-benzazepine-1-carboxamide

TLC: Rf 0.47 (chloroform: methanol=9:1);
NMR (CDCl$_3$):δ 7.28-7.17 (m, 4H), 4.90-4.20 (br, 2H), 3.63 (t, J=6.0 Hz, 2H), 3.34-3.04 (br, 2H), 2.86-2.40 (br, 3H), 2.18-1.66 (br, 4H), 1.58-1.28 (m, 5H).

EXAMPLE 32(7)

N-(2,6-dimethoxypyridin-3-yl)-2,3,4,5-tetrahydro-1H-1-benzazepine-1-carboxamide

TLC:Rf 0.38 (n-hexane:ethyl acetate=3:1);
NMR (CDCl$_3$):δ 8.30 (d, J=8.7 Hz, 1H), 7.34-7.27 (m, 4H), 6.48 (s, 1H), 6.27 (d, J=8.7 Hz, 1H), 4.85-4.50 (br, 1H), 3.83 (s, 3H), 3.76 (s, 3H), 3.00-2.50 (br, 3H), 2.20-1.70 (br, 3H), 1.54-1.24 (br, 1H).

EXAMPLE 32(8)

N-[2-[ethyl(3-methylphenyl)amino]ethyl]-8-fluoro-2,3,4,5-tetrahydro-1H-1-benzazepine-1-carboxamide TLC:Rf 0.69 (n-hexane:ethyl acetate=2:1);
NMR (DMSO-d$_6$):δ 1.06 (t, J=7.00 Hz, 3H), 1.56 (m, 2H), 1.71 (m, 2H), 2.22 (s, 3H), 2.64 (m, 2H), 3.24 (m, 6H), 3.48 (m, 2H), 5.57 (m, 1H), 6.39 (d, J=7.42 Hz, 1H), 6.53 (m, 2H), 6.88 (m, 2H), 6.98 (m, 1H), 7.26 (dd, J=8.24, 6.59 Hz, 1H).

EXAMPLE 32(9)

N-[2-[ethyl(phenyl)amino]ethyl]-2,3,4,5-tetrahydro-1H-1-benzazepine-1-carboxamide TLC:Rf 0.34 (n-hexane:ethyl acetate=2:1);
NMR (CDCl$_3$):δ 1.07 (t, J=7.14 Hz, 3H), 1.30 (m, 1H), 1.89 (m, 3H), 2.68 (m, 3H), 3.31 (m, 6H), 4.53 (m, 2H), 6.65 (m, 3H), 7.16 (m, 6H).

EXAMPLE 32(10)

N-(2-anilinoethyl)-2,3,4,5-tetrahydro-1H-1-benzazepine-1-carboxamide

TLC: Rf 0.18 (n-hexane:ethyl acetate=2:1);
NMR (CDCl$_3$):δ 1.33 (m, 1H), 1.86 (m, 3H), 2.67 (m, 3H), 3.19 (t, J=5.77 Hz, 2H), 3.40 (m, 2H), 4.17 (s, 1H), 4.53 (m, 2H), 6.62 (m, 3H), 7.17 (m, 6H).

EXAMPLE 32(11)

N-[3-methyl(phenyl)amino]propyl]-2,3,4,5-tetrahydro-1H-1-benzazepine-1-carboxamide TLC: Rf 0.19 (n-hexane:ethyl acetate=2:1);
NMR (CDCl$_3$):δ 1.32 (m, 1H), 1.71 (m, 5H), 2.74 (m, 6H), 3.25 (m, 4H), 4.46 (m, 2H), 6.64 (m, 3H), 7.19 (m, 6H).

EXAMPLE 32(12)

N-[2-(benzylamino)ethyl]-2,3,4,5-tetrahydro-1H-1-benzazepine-1-carboxamide

TLC:Rf 0.51 (dichloromethane: methanol=9:1);
NMR (CDCl$_3$):δ 1.33 (m, 1H), 1.94 (m, 3H), 2.68 (m, 5H), 3.30 (m, 2H), 3.71 (s, 2H), 4.72 (m, 2H), 7.24 (m, 9H).

EXAMPLE 32(13)

N-[2-[methyl(phenyl)amino]ethyl]-2,3,4,5-tetrahydro-1H-1-benzazepine-1-carboxamide TLC:Rf 0.48 (n-hexane:ethyl acetate=1:1);
NMR (CDCl$_3$):δ 1.32 (m, 1H), 1.85 (m, 3H), 2.68 (m, 3H), 2.87 (s, 3H), 3.41 (m, 4H), 4.47 (m, 2H), 6.67 (m, 3H), 7.14 (m, 6H).

EXAMPLE 32(14)

N-[2-(3-methylphenylamino)ethyl]-2,3,4,5-tetrahydro-1H-1-benzazepine-1-carboxamide TLC:Rf 0.42 (n-hexane:ethyl acetate=1:1);
NMR (CDCl$_3$):δ 1.34 (m, 1H), 1.89 (m, 3H), 2.25 (s, 3H), 2.68 (s, 3H), 3.18 (t, J=5.63 Hz, 2H), 3.40 (s, 2H), 4.10 (s, 1H), 4.52 (m, 2H), 6.45 (m, 3H), 7.14 (m, 5H).

EXAMPLE 32(15)

N-{2-ethyl(3-methylphenyl)amino]ethyl}-7-fluoro-2,3,4,5-tetrahydro-1H-1-benzazepine-1-carboxamide TLC:Rf 0.47 (n-hexane:ethyl acetate=1:1);
NMR (CDCl$_3$):δ 1.06 (t, J=7.00 Hz, 3H), 1.27 (m, 1H), 1.84 (m, 3H), 2.28 (s, 3H), 2.63 (m, 3H), 3.28 (q, J=6.87 Hz, 2H), 3.37 (m, 4H), 4.49 (m, 2H), 6.48 (m, 3H), 6.80 (td, J=8.38, 3.02 Hz, 1H), 6.92 (dd, J=8.93, 2.88 Hz, 1H), 6.98 (dd, J=8.52, 5.22 Hz, 1H), 7.07 (t, J=7.97 Hz, 1H).

EXAMPLE 32(16)

7-fluoro-N-(5-hydroxypentyl)-2,3,4,5-tetrahydro-1H-1-benzazepine-1-carboxamide

TLC:Rf 0.44 (ethyl acetate);
NMR (CDCl$_3$):δ 1.40 (m, 8H), 1.80 (m, 3H), 2.69 (m, 3H), 3.18 (m, 2H), 3.62 (t, J=6.46 Hz, 2H), 4.21 (m, 1H), 4.57 (m, 1H), 6.91 (td, J=8.24, 3.02 Hz, 1H), 6.98 (dd, J=8.93, 2.88 Hz, 1H), 7.16 (dd, J=8.52, 5.22 Hz, 1H).

EXAMPLE 32(17)

1-(4-phenylpiperazin-1-ylcarbonyl)-2,3,4,5-tetrahydro-1H-1-benzazepine

TLC:Rf 0.39 (n-hexane:ethyl acetate=2:1);
NMR (CDCl$_3$):δ 1.73 (m, 4H), 2.79 (m, 2H), 2.93 (m, 4H), 3.25 (m, 4H), 3.69 (s, 2H), 6.83 (m, 3H), 7.14 (m, 6H).

EXAMPLE 32(18)

N-{3-[ethyl(phenyl)amino]propyl}-2,3,4,5-tetrahydro-1H-1-benzazepine-1-carboxamide TLC:Rf 0.33 (n-hexane:ethyl acetate=2:1);
NMR (CDCl$_3$):δ 1.08 (t, J=7.14 Hz, 3H), 1.35 (m,1H), 1.75 (m, 5H), 2.66 (m, 3H), 3.24 (m, 6H), 4.35 (t, J=5.22 Hz, 1H), 4.60 (s, 1H), 6.61 (m, 3H), 7.20 (m, 6H).
Hydrochloride:
TLC:Rf 0.42 (n-hexane:ethyl acetate=1:1);
NMR(CDCl$_3$):δ 1.25 (m, 3H), 1.81 (m, 6H), 2.69 (m, 3H), 3.63 (m, 6H), 4.66 (m, 2H), 7.27 (m, 4H), 7.51 (m, 3H), 7.71 (m, 2H).

EXAMPLE 32(19)

N-(3-phenylaminopropyl)-2,3,4,5-tetrahydro-1H-1-benzazepine-1-carboxamide

TLC:Rf 0.43 (n-hexane:ethyl acetate=1:1);
NMR (CDCl$_3$):δ 1.31 (m, 1H), 1.74 (m, 5H), 2.65 (m, 3H), 3.13 (t, J=6.59 Hz, 2H), 3.27 (m, 2H), 4.03 (s,1H), 4.38 (t, J=5.49 Hz, 1H), 4.60 (s, 1H), 6.57 (m, 2H), 6.67 (m, 1H), 7.20 (m, 6H).

EXAMPLE 32(20)

N-phenyl-1-(2,3,4,5-tetrahydro-1H-1-benzazepin-1-ylcarbonyl)piperidine-4-amine

TLC:Rf 0.46 (n-hexane:ethyl acetate=2:1);
NMR (CDCl$_3$):δ 1.12 (m, 2H), 1.75 (m, 6H), 2.71 (m, 4H), 3.31 (m, 2H), 3.61 (m, 4H), 6.52 (m, 2H), 6.66 (m, 1H), 7.11 (m, 6H).

EXAMPLE 32(21)

4-(2,3,4,5-tetrahydro-1H-1-benzazepin-1-ylcarbonylaminomethyl)benzoic acid

TLC:Rf 0.63 (ethyl acetate);
NMR (DMSO-d$_6$):δ 1.62 (m, 2H), 1.73 (m, 2H), 2.71 (m, 2H), 3.50 (m, 2H), 4.29 (d, J=6.04 Hz, 2H), 5.82 (m, 1H), 7.23 (m, 6H), 7.86 (m, 2H).

EXAMPLE 32(22)

N-(2-phenoxyethyl)-2,3,4,5-tetrahydro-1H-1-benzazepine-1-carboxamide

TLC: Rf 0.16 (n-hexane:ethyl acetate=3:1);
NMR (CDCl$_3$):δ 1.30 (m, 1H), 1.83 (m, 3H), 2.63 (m, 3H), 3.56 (m, 2H), 4.00 (t, J=5.08 Hz, 2H), 4.58 (s, 1H), 4.76 (t, J=5.36 Hz, 1H), 6.80 (m, 2H), 6.94 (m, 1H), 7.21 (m, 6H).

EXAMPLE 32(23)

N-(3-phenylpropyl)-2,3,4,5-tetrahydro-1H-1-benzazepine-1-carboxamide

TLC:Rf 0.24 (n-hexane:ethyl acetate=3:1);
NMR (CDCl$_3$):δ 1.35 (m, 1H), 1.75 (m, 5H), 2.59 (m, 5H), 3.18 (m, 2H), 4.24 (t, J=5.36 Hz, 1H), 4.60 (s, 1H), 7.19 (m, 9H).

EXAMPLE 32(24)

N-(4-phenyl butyl)-2,3,4,5-tetrahydro-1H-1-benzazepine-1-carboxamide

TLC:Rf 0.26 (n-hexane:ethyl acetate=3:1);
NMR (CDCl$_3$):δ 1.49 (m, 5H), 1.86 (m, 3H), 2.61 (m, 5H), 3.18 (m, 2H), 4.21 (t, J=5.49 Hz, 1H), 4.60 (s, 1H), 7.20 (m, 9H).

EXAMPLE 32(25)

N-(3-phenoxypropyl)-2,3,4,5-tetrahydro-1H-1-benzazepine-1-carboxamide

TLC:Rf 0.28 (n-hexane:ethyl acetate=2:1);
NMR (CDCl$_3$):δ 1.38 (m, 1H), 1.87 (m, 5H), 2.65 (m, 3H), 3.39 (m, 2H), 3.95 (t, J=6.04 Hz, 2H), 4.61 (m, 2H), 6.69 (m, 2H), 6.91 (m, 1H), 7.21 (m, 6H).

EXAMPLE 32(26)

N-(2-benzyloxyethyl)-2,3,4,5-tetrahydro-1H-1-benzazepine-1-carboxamide

TLC:Rf 0.26 (n-hexane:ethyl acetate=2:1);
NMR (CDCl$_3$):δ 1.36 (m, 1H), 1.89 (m, 3H), 2.68 (m, 3H), 3.47 (m, 4H), 4.42 (s, 2H), 4.65 (m, 2H), 7.23 (m, 9H).

EXAMPLE 32(27)

N-[2-[ethyl(phenyl)amino]ethyl]-5,6,7,8-tetrahydro-9H-pyrid[2,3-b]azepine-9-carboxamide TLC:Rf 0.26 (n-hexane:ethyl acetate=1:1);
NMR (CDCl$_3$):δ 1.11 (t, J=7.00 Hz, 3H), 1.73 (m, 2H), 1.91 (m, 2H), 2.75 (m, 2H), 3.41 (m, 6H), 3.70 (s, 2H), 6.66 (m, 3H), 6.85 (s, 1H), 7.05 (dd, J=7.55, 4.81 Hz, 1H), 7.17 (m, 2H), 7.55 (dd, J=7.55, 1.79 Hz, 1H), 8.16 (dd, J=4.81, 1.79 Hz, 1H).

EXAMPLE 32(28)

N-[3-[ethyl(phenyl)amino]propyl]-5,6,7,8-tetrahydro-9H-pyrid[2,3-b]azepine-9-carboxamide TLC:Rf 0.23 (n-hexane:ethyl acetate=1:1);
NMR (CDCl$_3$):δ 1.10 (t, J=7.14 Hz, 3H), 1.82 (m, 6H), 2.77 (m, 2H), 3.30 (m, 6H), 3.70 (s, 2H), 6.62 (m, 3H), 6.78 (s, 1H), 7.12 (m, 3H), 7.57 (dd, J=7.42, 1.92 Hz, 1H), 8.22 (dd, J=4.67, 1.92 Hz, 1H).

EXAMPLE 32(29)

N-(cis-4-anilinocyclohexyl)-2,3,4,5-tetrahydro-1H-1-benzazepine-1-carboxamide

TLC:Rf 0.26 (n-hexane:ethyl acetate=2:1);
NMR (CDCl$_3$):δ 1.38 (m, 5H), 1.73 (m, 7H), 2.70 (m, 3H), 3.42 (m, 2H), 3.82 (m, 1H), 4.24 (d, J=7.97 Hz, 1H), 4.60 (s, 1H), 6.54 (m, 2H), 6.65 (m, 1H), 7.20 (m, 6H).

EXAMPLE 32(30)

N-(trans-4-anilinocyclohexyl)-2,3,4,5-tetrahydro-1H-1-benzazepine-1-carboxamide

TLC: Rf 0.18 (n-hexane:ethyl acetate=2:1);
NMR (CDCl$_3$):δ 1.17 (m, 5H), 1.99 (m, 7H), 2.65 (m, 3H), 3.14 (m, 1H), 3.44 (s, 1H), 3.68 (m, 1H), 4.06 (d, J=7.97 Hz, 1H), 4.59 (s, 1H), 6.53 (d, J=7.4 Hz, 2H), 6.65 (t, J=7.28 Hz, 1H), 7.20 (m, 6H).

EXAMPLE 32(31)

N-{3-[ethyl(4-fluorophenyl)amino]propyl}-2,3,4,5-tetrahydro-1H-1-benzazepine-1-carboxamide TLC:Rf 0.44 (n-hexane:ethyl acetate=1:1);
NMR (CDCl$_3$):δ 1.03 (t, J=7.00 Hz, 3H), 1.25 (m, 1H), 1.66 (m, 2H), 1.93 (m, 3H), 2.70 (m, 3H), 3.21 (m, 6H), 4.40 (m, 1H), 4.60 (m, 1H), 6.50 (m, 2H), 6.86 (m, 2H), 7.21 (m, 4H).

EXAMPLE 32(32)

N-(3-phenylpentyl)-2,3,4,5-tetrahydro-1H-1-benzazepine-1-carboxamide

TLC:Rf 0.31 (n-hexane:ethyl acetate=3:1);
NMR (CDCl$_3$):δ 0.73 (t, J=7.42 Hz, 3H), 1.52 (m, 4H), 1.85 (m, 4H), 2.34 (m, 1H), 2.63 (m, 3H), 3.01 (s, 2H), 4.12 (m, 1H), 4.57 (s, 1H), 7.01 (d, J=6.87 Hz, 2H), 7.19 (m, 7H).

EXAMPLE 32(33)

N-[3-[ethyl(3-fluorophenyl)amino]propyl]-2,3,4,5-tetrahydro-1H-1-benzazepine-1-carboxamide TLC:Rf 0.72 (n-hexane:ethyl acetate=1:1);
NMR (CDCl$_3$):δ 1.09 (t, J=7.00 Hz, 3H), 1.30 (m, 1H), 1.71 (m, 5H), 2.71 (m, 3H), 3.24 (m, 6H), 4.32 (m, 1H), 4.59 (m, 1H), 6.28 (m, 3H), 7.07 (m, 1H), 7.23 (m, 4H).

EXAMPLE 32(34)

N-[3-[ethyl(2-fluorophenyl)amino]propyl]-2,3,4,5-tetrahydro-1H-1-benzazepine-1-carboxamide TLC:Rf 0.55 (n-hexane:ethyl acetate=1:1);
NMR (CDCl$_3$):δ 0.97 (t, J=7.14 Hz, 3H), 1.32 (m, 1H), 1.63 (m, 2H), 1.86 (m, 3H), 2.71 (m, 3H), 3.07 (m, 4H), 3.22 (q, J=6.41 Hz, 2H), 4.42 (m, 1H), 4.61 (m, 1H), 6.90 (m, 4H), 7.21 (m, 4H).

EXAMPLE 32(35)

N-[3-(2,3-dihydro-1H-indol-1-yl)propyl]-2,3,4,5-tetrahydro-1H-1-benzazepine-1-carboxamide TLC:Rf 0.23 (n-hexane:ethyl acetate=2:1);
NMR (CDCl$_3$):δ 1.32 (s, 1H), 1.81 (m, 5H), 2.74 (m, 5H), 3.01 (m, 2H), 3.26 (m, 4H), 4.59 (m, 2H), 6.32 (d, J=7.69 Hz, 1H), 6.63 (t, J=7.28 Hz, 1H), 7.11 (m, 6H).

EXAMPLE 32(36)

N-[3-[isopropyl(phenyl)amino]propyl]-2,3,4,5-tetrahydro-1H-1-benzazepine-1-carboxamide TLC:Rf 0.30 (n-hexane:ethyl acetate=2:1);
NMR (CDCl$_3$):δ 1.09 (d, J=6.59 Hz, 6H), 1.31 (s, 1H), 1.69 (m, 5H), 2.60 (m, 3H), 3.09 (m, 2H), 3.25 (q, J=6.59 Hz, 2H), 3.91 (m, 1H), 4.37 (t, J=5.49 Hz, 1H), 4.60 (s, 1H), 6.66 (m, 3H), 7.21 (m, 6H).

EXAMPLE 32(37)

N-[2-(2,3-dihydro-1H-indol-1-yl)ethyl]-2,3,4,5-tetrahydro-1H-1-benzazepine-1-carboxamide TLC:Rf 0.25 (n-hexane:ethyl acetate=2:1);
NMR (CDCl$_3$):δ 1.31 (s, 1H), 1.85 (m, 3H), 2.58 (m, 3H), 2.87 (t, J=8.38 Hz, 2H), 3.13 (t, J=6.04 Hz, 2H), 3.31 (m, 4H), 4.58 (m, 2H), 6.42 (d, J=7.69 Hz, 1H), 6.62 (m, 1H), 7.11 (m, 6H).

EXAMPLE 32(38)

N-(3-diphenylaminopropyl)-2,3,4,5-tetrahydro-1H-1-benzazepine-1-carboxamide

TLC:Rf 0.37 (n-hexane:ethyl acetate=2:1);
NMR (CDCl$_3$):δ 1.32 (s, 1H), 1.80 (m, 5H), 2.60 (m, 3H), 3.24 (m, 2H), 3.68 (m, 2H), 4.27 (t, J=5.49 Hz, 1H), 4.59 (s, 1H), 6.90 (m, 6H), 7.20 (m, 8H).

EXAMPLE 32(39)

N-(1-phenylpiperidin-4-yl)-2,3,4,5-tetrahydro-1H-1-benzazepine-1-carboxamide

TLC:Rf 0.27 (n-hexane:ethyl acetate=2:1);
NMR (CDCl$_3$):δ 1.34 (m, 3H), 1.91 (m, 5H), 2.80 (m, 5H), 3.50 (m, 2H), 3.83 (m, 1H), 4.13 (d, J=7.97 Hz, 1H), 4.60 (s, 1H), 6.81 (t, J=7.28 Hz, 1H), 6.88 (d, J=7.97 Hz, 2H), 7.21 (m, 6H).

EXAMPLE 32(40)

N-(1-phenylpiperidin-4-ylmethyl)-2,3,4,5-tetrahydro-1H-1-benzazepine-1-carboxamide TLC:Rf 0.34 (n-hexane:ethyl acetate=1:1);
NMR (CDCl$_3$):δ 1.27 (m, 3H), 1.63 (m, 6H), 2.67 (m, 5H), 3.09 (m, 2H), 3.66 (d, J=12.36 Hz, 2H), 4.35 (t, J=5.63 Hz, 1H), 4.61 (s, 1H), 6.81 (t, J=7.28 Hz, 1 H), 6.91 (d, J=7.69 Hz, 2H), 7.24 (m, 6H).

EXAMPLE 32(41)

N-[ethyl (4-fluorophenyl)aminocarbonylmethyl]-2,3,4,5-tetrahydro-1H-1-benzazepine-1-carboxamide TLC:Rf 0.33 (ethyl acetate: n-hexane=1:1);
NMR (CDCl$_3$):δ 1.07 (t, J=7.14 Hz, 3H), 1.35 (m, 1H), 1.90 (m, 3H), 2.70 (m, 3H), 3.65 (m, 4H), 4.55 (m, 1H), 5.10 (t, J=4.40 Hz, 1H), 7.21 (m, 8H).

EXAMPLE 32(42)

N-{2-[ethyl(4-fluorophenyl)amino]ethyl}-2,3,4,5-tetrahydro-1H-1-benzazepine-1-carboxamide TLC:Rf 0.31 (ethyl acetate: n-hexane=1:2);
NMR (CDCl$_3$):δ 1.03 (t, J=7.00 Hz, 3H), 1.33 (m, 1H), 1.89 (m, 3H), 2.68 (m, 3H), 3.24 (m, 6H), 4.59 (m, 2H), 6.61 (m, 2H), 6.88 (m, 2H), 7.18 (m, 4H).

EXAMPLE 32(43)

N-(1-phenylpyrrolidin-3-yl)-2,3,4,5-tetrahydro-1H-1-benzazepine-1-carboxamide

TLC:Rf 0.45 (n-hexane:ethyl acetate=2:1);
NMR (CDCl$_3$):δ 1.32 (s, 1H), 1.89 (m, 4H), 2.26 (m, 1H), 2.64 (m, 3H), 2.99 (s, 1H), 3.25 (t, J=7.00 Hz, 2H), 3.58 (dd, J=9.61, 6.59 Hz, 1H), 4.38 (d, J=7.14 Hz, 1H), 4.54 (m, 2H), 6.51 (d, J=7.97 Hz, 2H), 6.67 (t, J=7.28 Hz, 1H), 7.22 (m, 6H).

EXAMPLE 32(44)

N-[ethyl (3-fluorophenyl)aminocarbonylmethyl]-2,3,4,5-tetrahydro-1H-1-benzazepine-1-carboxamide TLC:Rf 0.44 (n-hexane:ethyl acetate=1:1);
NMR (CDCl$_3$):δ 1.08 (t, J=7.14 Hz, 3H), 1.35 (m, 1H), 1.83 (m, 3H), 2.71 (m, 3H), 3.64 (m, 4H), 4.53 (m, 1H), 5.10 (m, 1H), 6.90 (m, 1H), 6.98 (m, 1H), 7.09 (m, 1H), 7.26 (m, 4H), 7.40 (m, 1H).

EXAMPLE 32(45)

N-{2-[ethyl(3-fluorophenyl)amino]ethyl}-2,3,4,5-tetrahydro-1H-1-benzazepine-1-carboxamide TLC:Rf 0.44 (n-hexane:ethyl acetate=1:1);
NMR (CDCl$_3$):δ 1.08 (t, J=7.14 Hz, 3H), 1.32 (m, 1H), 1.79 (m, 3H), 2.63 (m, 3H), 3.30 (m, 6H), 4.43 (m, 1H), 4.59 (m, 1H), 6.32 (m, 2H), 6.43 (m, 1H), 7.16 (m, 5H).

EXAMPLE 32(46)

N-[[isopropyl(phenyl)aminocarbonylmethyl]-2,3,4,5-tetrahydro-1H-1-benzazepine-1-carboxamide TLC:Rf 0.49 (ethyl acetate: n-hexane=1:1);
NMR (CDCl$_3$):δ 1.02 (d, J=6.87 Hz, 6H), 1.37 (m, 1H), 1.88 (m, 3H), 2.67 (m, 3H), 3.54 (m, 2H), 4.54 (m, 1H), 4.92 (m, 1H), 5.17 (t, J=4.26 Hz, 1H), 7.10 (m, 2H), 7.25 (m, 4H), 7.41 (m, 3H).

EXAMPLE 32(47)

N-[benzyl(phenyl)aminocarbonylmethyl]-2,3,4,5-tetrahydro-1H-1-benzazepine-1-carboxamide TLC:Rf 0.45 (ethyl acetate: n-hexane=1:1);
NMR (CDCl$_3$):δ 1.26 (m, 1H), 2.04 (m, 3H), 2.74 (m, 3H), 3.69 (m, 2H), 4.54 (m, 1H), 4.84 (s, 2H), 5.15 (t, J=4.81 Hz, 1H), 6.98 (m, 2H), 7.12 (m, 2H), 7.28 (m, 10H).

EXAMPLE 32(48)

N-[2-[isopropyl(phenyl )amino]ethyl]-2,3,4,5-tetrahydro-1H-1-benzazepine-1-carboxamide TLC:Rf 0.39 (ethyl acetate: n-hexane=1:2);
NMR (CDCl$_3$):δ 1.07 (d, J=6.59 Hz, 6H), 1.34 (m, 1H), 1.90 (m, 3H), 2.64 (m, 3H), 3.24 (m, 4H), 3.87 (m, 1H), 4.63 (m, 2H), 6.75 (m, 3H), 7.21 (m, 6H).

EXAMPLE 32(49)

N-[2-[benzyl(phenyl)amino]ethyl]-2,3,4,5-tetrahydro-1H-1-benzazepine-1-carboxamide TLC:Rf 0.38 (ethyl acetate: n-hexane=1:2);
NMR (CDCl$_3$):δ 1.32 (m, 1H), 1.89 (m, 3H), 2.62 (m, 3H), 3.37 (m, 2H), 3.53 (t, J=6.46 Hz, 2H), 4.46 (m, 3H), 4.62 (m, 1H), 6.69 (m, 3H), 7.16 (m, 11H).

EXAMPLE 32(50)

N-[ethyl(2-fluorophenyl)aminocarbonylmethyl]-2,3,4,5-tetrahydro-1H-1-benzazepine-1-carboxamide TLC:Rf 0.42 (n-hexane:ethyl acetate=1:1);
NMR (DMSO-d$_6$):δ 1.01 (t, J=7.14 Hz, 3H), 1.58 (s, 2H), 1.69 (m, 2H), 2.71 (m, 2H), 3.58 (m, 6H), 5.22 (m, 1H), 7.33 (m, 8H).

EXAMPLE 32(51)

N-{2-[ethyl(2-fluorophenyl)amino]ethyl}-2,3,4,5-tetrahydro-1H-1-benzazepine-1-carboxamide TLC:Rf 0.69 (n-hexane:ethyl acetate=1:1);
NMR (CDCl$_3$):δ 0.94 (t, J=7.14 Hz, 3H), 1.34 (m, 1H), 1.88 (m, 3H), 2.63 (m, 3H), 3.11 (m, 6H), 4.67 (m, 2H), 6.91 (m, 4H), 7.19 (m, 4H).

EXAMPLE 32(52)

N-[1-(4-methoxyphenyl)piperidin-4-yl]-2,3,4,5-tetrahydro-1H-1-benzazepine-1-carboxamide TLC:Rf 0.37 (n-hexane:ethyl acetate=1:1);
NMR (CDCl$_3$):δ 1.40 (m, 3H), 1.93 (m, 5H), 2.74 (m, 5H), 3.33 (d, J=11.54 Hz, 2H), 3.80 (m, 4H), 4.14 (d, J=8.24 Hz, 1H), 4.59 (s, 1H), 6.83 (m, 4H), 7.23 (m, 4H).

EXAMPLE 32(53)

N-[1-(3-methoxyphenyl)piperidine4-yl]-2,3,4,5-tetrahydro-1H-1-benzazepine-1-carboxamide TLC:Rf 0.30 (n-hexane:ethyl acetate=3:2);
NMR (CDCl$_3$):δ 1.31 (m, 3H), 1.92 (m, 5H), 2.81 (m, 5H), 3.51 (d, J=12.64 Hz, 2H), 3.83 (m, 4H), 4.12 (d, J=7.69 Hz, 1H), 4.59 (s, 1H), 6.37 (m, 1H), 6.41 (t, J=2.34 Hz, 1H), 6.49 (m, 1H), 7.20 (m, 5H).

EXAMPLE 32(54)

N-[1-(4-fluorophenyl)piperidin-4-yl]-2,3,4,5-tetrahydro-1H-1-benzazepine-1-carboxamide TLC:Rf 0.27 (n-hexane:ethyl acetate=3:2);
NMR (CDCl$_3$):δ 1.35 (m, 3H), 1.94 (m, 5H), 2.76 (m, 5H), 3.37 (d, J=11.81 Hz, 2H), 3.80 (m, 1H), 4.13 (d, J=7.97 Hz, 1H), 4.60 (s, 1H), 6.88 (m, 4H), 7.23 (m, 4H).

EXAMPLE 32(55)

N-[1-(3-fluorophenyl)piperidin-4-yl]-2,3,4,5-tetrahydro-1H-1-benzazepine-1-carboxamide TLC:Rf 0.31 (n-hexane:ethyl acetate=3:2);
NMR (CDCl$_3$):δ 1.30 (m, 3H), 1.92 (m, 5H), 2.80 (m, 5H), 3.53 (d, J=12.36 Hz, 2H), 3.85 (m, 1H), 4.12 (d, J=7.69 Hz, 1H), 4.60 (s, 1H), 6.53 (m, 3H), 7.20 (m, 5H).

EXAMPLE 32(56)

N-{3-[ethyl(4-fluorophenyl)amino]propyl}-7-fluoro-2,3,4,5-tetrahydro-1H-1-benzazepine-1-carboxamide TLC:Rf 0.41 (n-hexane:ethyl acetate=1:1);
NMR (CDCl$_3$):δ 1.03 (t, J=7.14 Hz, 3H), 1.31 (m, 1H), 1.68 (m, 2H), 1.88 (m, 3H), 2.65 (m, 3H), 3.18 (m, 4H), 3.25 (m, 2H), 4.39 (m, 1H), 4.57 (m, 1H), 6.52 (m, 2H), 6.86 (m, 3H), 6.95 (dd, J=8.79, 3.02 Hz, 1H), 7.11 (dd, J=8.52, 5.49 Hz, 1H).

EXAMPLE 32(57)

N-[ethyl(4-fluorophenyl)aminocarbonylmethyl]-7-fluoro-2,3,4,5-tetrahydro-1H-1-benzazepine-1-carboxamide TLC:Rf 0.34 (n-hexane:ethyl acetate=1:1);
NMR (CDCl$_3$):δ 1.07 (t, J=7.28 Hz, 3H), 1.25 (m, 1H), 1.82 (m, 3H), 2.65 (m, 3H), 3.65 (m, 4H), 4.52 (m, 1H), 5.06 (m, 1H), 7.11 (m, 7H).

EXAMPLE 32(58)

N-(2,6-dimethylbenzyl)-2,3,4,5-tetrahydro-1H-1-benzazepine-1-carboxamide

TLC:Rf 0.46 (ethyl acetate: n-hexane=1:2);
NMR (CDCl$_3$):δ 1.34 (m, 1H), 1.91 (m, 3H), 2.29 (s, 6H), 2.67 (m, 3H), 4.12 (m, 1H), 4.42 (d, J=4.67 Hz, 2H), 4.72 (m, 1H), 7.01 (m, 3H), 7.17 (m, 4H).

EXAMPLE 32(59)

N-(1-methyl-1-phenylethyl)-2,3,4,5-tetrahydro-1H-1-benzazepine-1-carboxamide

TLC:Rf 0.53 (ethyl acetate: n-hexane=1:2);
NMR (CDCl$_3$):δ 1.29 (m, 1H), 1.57 (s, 6H), 1.93 (m, 3H), 2.61 (m, 3H), 4.57 (m, 2H), 7.25 (m, 9H).

EXAMPLE 32(60)

N-[1-(4-chlorophenyl)-1-methylethyl]-2,3,4,5-tetrahydro-1H-1-benzazepine-1-carboxamide TLC:Rf 0.36 (ethyl acetate: n-hexane=1:3);
NMR (CDCl$_3$):δ 1.29 (m, 1H), 1.53 (s, 6H), 1.93 (m, 3H), 2.67 (m, 3H), 4.52 (m, 2H), 7.27 (m, 8H).

EXAMPLE 32(61)

N-{2-[ethyl(4-fluorophenyl)amino]ethyl}-7-fluoro-2,3,4,5-tetrahydro-1H-1-benzazepine-1-carboxamide TLC:Rf 0.50 (n-hexane:ethyl acetate=1:1);
NMR (CDCl$_3$):δ 1.03 (t, J=7.00 Hz, 3H), 1.30 (m, 1H), 1.88 (m, 3H), 2.63 (m, 3H), 3.24 (m, 6H), 4.42 (m, 1H), 4.55 (m, 1H), 6.61 (m, 2H), 6.88 (m, 4H), 7.02 (dd, J=8.52, 5.22 Hz, 1H).

EXAMPLE 32(62)

N-[1-(2-fluorophenyl)piperidin-4-yl]-2,3,4,5-tetrahydro-1H-1-benzazepine-1-carboxamide TLC:Rf 0.43 (n-hexane:ethyl acetate=3:2);
NMR (CDCl$_3$):δ 1.36 (m, 3H), 1.90 (m, 5H), 2.75 (m, 5H), 3.29 (d, J=11.26 Hz, 2H), 3.81 (m, 1H), 4.15 (d, J=7.97 Hz, 1H), 4.61 (s, 1H), 6.95 (m, 4H), 7.22 (m, 4H).

EXAMPLE 32(63)

7-fluoro-N-(1-phenylpiperidin-4-yl)-2,3,4,5-tetrahydro-1H-1-benzazepine-1-carboxamide TLC:Rf 0.47 (n-hexane:ethyl acetate=3:2);
NMR (CDCl$_3$):δ 1.33 (m, 3H), 1.93 (m, 5H), 2.79 (m, 5H), 3.52 (d, J=12.36 Hz, 2H), 3.82 (m, 1H), 4.07 (d, J=7.97 Hz, 1H), 4.57 (s, 1H), 6.90 (m, 5H), 7.20 (m, 3H).

EXAMPLE 32(64)

N-[1-(2-methoxyphenyl)piperidin-4-yl]-2,3,4,5-tetrahydro-1H-1-benzazepine-1-carboxamide hydrochloride TLC:Rf 0.45 (n-hexane:ethyl acetate=3:2);
NMR (CDCl$_3$):δ 1.35 (s, 1H), 1.91 (m, 5H), 2.66 (m, 5H), 3.53 (d, J=10.99 Hz, 2H), 4.07 (m, 6H), 4.52 (m, 2H), 7.03 (m, 2H), 7.15 (m, 1H), 7.26 (m, 3H), 7.40 (t, J=7.83 Hz, 1H), 8.50 (d, J=7.14 Hz, 1H).

EXAMPLE 32(65)

N-{(1S)-1-ethyl(4-fluorophenyl)aminocarbonyl]ethyl}-2,3,4,5-tetrahydro-1H-1-benzazepine-1-carboxamide TLC:Rf 0.66 (n-hexane:ethyl acetate=1:1);
NMR (DMSO-d$_6$):δ 0.99 (m, 6H), 1.69 (m, 4H), 2.71 (m, 2H), 3.61 (m, 4H), 4.21 (m, 1H), 5.00 (m, 1H), 7.27 (m, 8H).

EXAMPLE 32(66)

N-{2-[ethyl(4-fluorophenyl)aminocarbonyl]ethyl}-2,3,4,5-tetrahydro-1H-1-benzazepine-1-carboxamide TLC:Rf 0.35 (ethyl acetate: n-hexane=3:1);
NMR (CDCl$_3$):δ 1.05 (t, J=7.14 Hz, 3H), 1.43 (m, 1H), 1.84 (m, 3H), 2.15 (t, J=5.91 Hz, 2H), 2.61 (m, 3H), 3.35 (m, 2H), 3.64 (q, J=7.14 Hz, 2H), 4.54 (m, 1H), 4.92 (t, J=5.77 Hz, 1H), 7.18 (m, 8H).

EXAMPLE 32(67)

N-{(1S)-2-[ethyl(4-fluorophenyl)amino]-1-methylethyl}-2,3,4,5-tetrahydro-1H-1-benzazepine-1-carboxamide TLC:Rf 0.56 (n-hexane:ethyl acetate=1:1);
NMR (DMSO-d$_6$):δ 1.01 (m, 6H), 1.57 (m, 2H), 1.67 (m, 2H), 2.62 (m, 2H), 3.04 (m, 1H), 3.24 (m, 3H), 3.45 (m, 2H), 3.94 (m, 1H), 4.84 (m, 1H), 6.70 (m, 2H), 6.90 (m, 2H), 7.15 (m, 4H).

EXAMPLE 32(68)

N-(2-benzyloxybenzyl)-2,3,4,5-tetrahydro-1H-1-benzazepine-1-carboxamide

TLC:Rf 0.27 (ethyl acetate: n-hexane=1:3);
NMR (CDCl$_3$):δ 1.35 (m, 1H), 1.85 (m, 3H), 2.66 (m, 3H), 4.42 (m, 2H), 4.61 (m, 1H), 4.89 (t, J=5.68 Hz, 1H), 4.95 (s, 2H), 6.85 (d, J=8.06 Hz, 1H), 6.92 (t, J=6.96 Hz, 1H), 7.21 (m, 11H).

EXAMPLE 32(69)

N-[(1R)-1-[ethyl(4-fluorophenyl)aminocarbonyl]ethyl]-2,3,4,5-tetrahydro-1H-1-benzazepine-1-carboxamide TLC:Rf 0.54 (n-hexane:ethyl acetate=1:1);
NMR (DMSO-d$_6$):δ 0.96 (d, J=6.77 Hz, 3H), 1.01 (t, J=7.14 Hz, 3H), 1.65 (m, 4H), 2.70 (m, 2H), 3.62 (m, 4H), 4.23 (m, 1H), 5.01 (m, 1H), 7.28 (m, 8H).

EXAMPLE 32(70)

N-{2-[methyl(phenyl)amino]benzyl}-2,3,4,5-tetrahydro-1H-1-benzazepine-1-carboxamide TLC:Rf 0.39 (ethyl acetate: n-hexane=1:2);
NMR (CDCl$_3$):δ 1.36 (m, 1H), 1.80 (m, 3H), 2.68 (m, 3H), 3.08 (s, 3H), 4.25 (d, J=5.86 Hz, 2H), 4.54 (m, 1H), 4.65 (t, J=5.68 Hz, 1H), 6.41 (d, J=7.69 Hz, 2H), 6.68 (t, J=7.14 Hz, 1H), 7.18 (m, 9H), 7.41 (m, 1H).

EXAMPLE 32(71)

N-(2,3,4,5-tetrahydro-1H-1-benzazepin-1-ylcarbonyl)phenylalanine methyl ester

TLC:Rf 0.55 (n-hexane:ethyl acetate=1:1);
NMR (CDCl$_3$):δ 1.26 (m, 1H), 1.88 (m, 3H), 2.80 (m, 5H), 3.69 (s, 3H), 4.68 (m, 3H), 7.14 (m, 9H).

EXAMPLE 32(72)

N-{[t-butyl(4-fluorophenyl)amino]carbonylmethyl}-2,3,4,5-tetrahydro-1H-1-benzazepine-1-carboxamide TLC:Rf 0.48 (ethyl acetate: n-hexane=1:1);
NMR (CDCl$_3$):δ 1.23 (m, 1H), 1.31 (s, 9H), 1.88 (m, 3H), 2.68 (m, 3H), 3.43 (m, 2H), 4.52 (m, 1H), 5.13 (t, J=4.49 Hz, 1H), 7.07 (m, 4H), 7.26 (m, 4H).

EXAMPLE 32(73)

N-{2-[t-butyl(4-fluorophenyl)amino]ethyl}-2,3,4,5-tetrahydro-1H-1-benzazepine-1-carboxamide TLC:Rf 0.21 (ethyl acetate: n-hexane=1:2);
NMR (CDCl$_3$):δ 0.85 (s, 9H), 1.35 (m, 1H), 1.84 (m, 3H), 2.64 (m, 3H), 2.94 (m, 4H), 4.55 (m, 1H), 4.95 (m, 1H), 6.74 (m, 2H), 6.86 (m, 2H), 7.30 (m, 4H).

EXAMPLE 32(74)

N-{2-[cyclopropyl(4-fluorophenyl)aminocarbonyl]ethyl}-2,3,4,5-tetrahydro-1H-1-benzazepine-1-carboxamide TLC:Rf 0.33 (n-hexane:ethyl acetate=1:2);
NMR (DMSO-d$_6$):δ 0.41 (m, 2H), 0.76 (m, 2H), 1.65 (m, 4H), 2.44 (t, J=6.50 Hz, 2H), 2.66 (m, 2H), 3.09 (m, 1H), 3.26 (q, J=6.16 Hz, 2H), 3.45 (m, 2H), 5.17 (m, 1H), 7.18 (m, 8H).

EXAMPLE 32(75)

N-{3-[cyclopropyl(4-fluorophenyl)amino]propyl}-2,3,4,5-tetrahydro-1H-1-benzazepine-1-carboxamide TLC:Rf 0.42 (n-hexane:ethyl acetate=1:1);
NMR (CDCl$_3$):δ0.48 (m, 2H), 0.74 (m, 2H), 1.26 (m, 1H), 1.65 (m, 2H), 1.99 (m, 3H), 2.31 (m, 1H), 2.72 (m, 3H), 3.18 (m, 2H), 3.31 (m, 2H), 4.25 (m, 1H), 4.61 (m, 1H), 6.83 (m, 4H), 7.22 (m, 4H).

EXAMPLE 32(76)

N-{1-ethyl(4-fluorophenyl)aminocarbonyl]-2-phenylethyl}-2,3,4,5,-tetrahydro-1H-1-benzazepine-1-carboxamide TLC:Rf0.33 (n-hexane: ethyl acetate=2:1);
NMR (DMSO-d$_6$):δ 1.00 (m, 3H), 1.62 (m, 4H), 2.66 (m, 4H), 3.41 (m, 2H), 3.60 (m, 2H), 4.44 (m, 1H), 4.90 (d, J=8.24 Hz, 1H), 7.14 (m, 13H).

EXAMPLE 32(77)

Cyclopropyl(4-fluorophenyl)aminocarbonylmethyl-2,3,4,5-tetrahydro-1H-1-benzazepine-1-carboxamide TLC: Rf 0.42 (n-hexane:ethyl acetate=1:1);
NMR (DMSO-d$_6$):δ 0.63 (m, 4H), 1.67 (m, 4H), 2.72 (m, 2H), 3.13 (m, 1H), 3.48 (m, 2H), 3.86 (d, J=5.13 Hz, 2H), 5.21 (m, 1H), 7.22 (m, 8H).

EXAMPLE 32(78)

[(2R)-ethyl(4-fluorophenyl)amino-2-propylamino]-2,3,4,5-tetrahydro-1H-1-benzazepine-1-carboxamide TLC:Rf 0.71 (n-hexane:ethyl acetate=1:1);
NMR (CDCl$_3$):δ 1.06 (m, 6H), 1.25 (m, 1H), 1.92 (m, 3H), 2.61 (m, 3H), 2.91 (dd, J=14.46, 7.51 Hz, 1H), 3.28 (m, 3H), 4.06 (m, 1H), 4.18 (m, 1H), 4.58 (m, 1H), 7.10 (m, 8H).

EXAMPLE 32(79)

N-{2-[cyclopropyl(4-fluorophenyl)amino]ethyl}-2,3,4,5-tetrahydro-1H-1-benzazepine-1-carboxamide TLC:Rf 0.69 (n-hexane:ethyl acetate=1:1);
NMR (CDCl$_3$):δ 0.46 (m, 2H), 0.75 (m, 2H), 1.26 (m, 1H), 1.91 (m, 3H), 2.34 (m, 1H), 2.62 (m, 3H), 3.42 (m, 4H), 4.31 (m, 1H), 4.56 (m, 1H), 7.08 (m, 8H).

EXAMPLE 32(80)

N-[3-[ethyl(phenyl)aminocarbonyl]propyl]-2,3,4,5-tetrahydro-1H-1-benzazepine-1-carboxamide TLC:Rf 0.20 (ethyl acetate: n-hexane=3:1);
NMR (CDCl$_3$):δ 1.07 (t, J=7.14 Hz, 3H), 1.38 (m, 1H), 1.69 (m, 5H), 1.97 (t, J=7.23 Hz, 2H), 2.54 (m, 3H), 3.09 (m, 2H), 3.69 (q, J=7.14 Hz, 2H), 4.31 (m, 1H), 4.61 (m, 1H), 7.24 (m, 9H).

EXAMPLE 32(81)

N-{4-[ethyl(phenyl)amino]butyl}-2,3,4,5-tetrahydro-1H-1-benzazepine-1-carboxamide TLC:Rf 0.31 (ethyl acetate: n-hexane=2:3);
NMR (CDCl$_3$):δ 1.11 (t, J=7.05 Hz, 3H), 1.45 (m, 5H), 1.93 (m, 3H), 2.61 (m, 3H), 3.23 (m, 4H), 3.32 (q, J=7.02 Hz, 2H), 4.25 (t, J=5.49 Hz, 1H), 4.63 (m, 1H), 6.63 (m, 3H), 7.20 (m, 6H).

EXAMPLE 32(82)

N-(2-phenoxybenzyl)-2,3,4,5-tetrahydro-1H-1-benzazepine-1-carboxamide

TLC:Rf 0.21 (n-hexane:ethyl acetate=3:1);
NMR(CDCl$_3$):δ 1.31 (s, 1H), 1.88 (m, 3H), 2.66 (m, 3H), 4.39 (s, 2H), 4.60 (s, 1H), 4.83 (t, J=6.04 Hz, 1H), 6.79 (m, 3H), 7.16 (m, 9H), 7.40 (dd, J=7.32, 1.46 Hz, 1H).

EXAMPLE 32(83)

N-[1-[ethyl(4-fluorophenyl)amino]cyclopropan-1-yl methyl]-2,3,4,5-tetrahydro-1H-1-benzazepine-1-carboxamide TLC:Rf 0.27 (n-hexane:ethyl acetate=2:1);
NMR(CDCl$_3$):δ 0.84 (m, 4H), 1.03 (t, J=7.05 Hz, 3H), 1.32 (m, 1H), 1.89 (m, 3H), 2.60 (m, 3H), 3.31 (q, J=7.02 Hz, 2H), 3.38 (d, J=6.04 Hz, 2H), 4.35 (t, J=5.95 Hz, 1H), 4.58 (m, 1H), 6.66 (m, 2H), 6.85 (m, 2H), 7.00 (m, 1H), 7.19 (m, 3H).

EXAMPLE 32(84)

N-(4-benzyloxybenzyl)-2,3,4,5-tetrahydro-1H-1-benzazepine-1-carboxamide

TLC:Rf 0.29 (n-hexane:ethyl acetate=2:1);
NMR(CDCl$_3$):δ 1.36 (m, 1H), 1.92 (m, 3H), 2.60 (m, 3H), 4.32 (s, 2H), 4.56 (m, 2H), 5.03 (s, 2H), 6.89 (m, 2H), 7.14 (m, 2H), 7.30 (m, 9H).

EXAMPLE 32(85)

N-(2-fluorobenzyl)-2,3,4,5-tetrahydro-1H-1-benzazepine-1-carboxamide

TLC:Rf 0.38 (n-hexane:ethyl acetate=2:1).

EXAMPLE 32(86)

N-(3-fluorobenzyl)-2,3,4,5-tetrahydro-1H-1-benzazepine-1-carboxamide

TLC:Rf 0.31(n-hexane:ethyl acetate=2:1).

EXAMPLE 32(87)

N-(2-chlorobenzyl)-2,3,4,5-tetrahydro-1H-1-benzazepine-1-carboxamide

TLC:Rf 0.39(n-hexane:ethyl acetate=2:1).

EXAMPLE 32(88)

N-(3-chlorobenzyl)-2,3,4,5-tetrahydro-1H-1-benzazepine-1-carboxamide

TLC:Rf 0.33(n-hexane:ethyl acetate=2:1).

EXAMPLE 32(89)

N-(4-chlorobenzyl)-2,3,4,5-tetrahydro-1H-1-benzazepine-1-carboxamide

TLC:Rf 0.32(n-hexane:ethyl acetate=2:1).

EXAMPLE 32(90)

N-(2-methoxybenzyl)-2,3,4,5-tetrahydro-1H-1-benzazepine-1-carboxamide

TLC:Rf 0.29(n-hexane:ethyl acetate=2:1).

EXAMPLE 32(91)

N-(3-methoxybenzyl)-2,3,4,5-tetrahydro-1H-1-benzazepine-1-carboxamide

TLC:Rf 0.23(n-hexane:ethyl acetate=2:1).

EXAMPLE 32(92)

N-(2-methylbenzyl)-2,3,4,5-tetrahydro-1H-1-benzazepine-1-carboxamide

TLC:Rf 0.36(n-hexane:ethyl acetate=2:1).

EXAMPLE 32(93)

N-(3-methylbenzyl)-2,3,4,5-tetrahydro-1H-1-benzazepine-1-carboxamide

TLC:Rf 0.36(n-hexane:ethyl acetate=2:1).

EXAMPLE 32(94)

N-(4-methylbenzyl)-2,3,4,5-tetrahydro-1H-1-benzazepine-1-carboxamide

TLC:Rf 0.36(n-hexane:ethyl acetate=2:1).

EXAMPLE 32(95)

N-(2-trifluoromethylbenzyl)-2,3,4,5-tetrahydro-1H-1-benzazepine-1-carboxamide

TLC:Rf 0.44(n-hexane:ethyl acetate=2:1).

EXAMPLE 32(96)

N-(2-aminobenzyl)-2,3,4,5-tetrahydro-1H-1-benzazepine-1-carboxamide

TLC: Rf 0.18(n-hexane:ethyl acetate=2:1).

EXAMPLE 32(97)

N-(2-trifluoromethoxybenzyl)-2,3,4,5-tetrahydro-1H-1-benzazepine-1-carboxamide

TLC:Rf 0.44(n-hexane:ethyl acetate=2:1).

EXAMPLE 32(98)

N-(2-difluoromethoxybenzyl)-2,3,4,5-tetrahydro-1H-1-benzazepine-1-carboxamide

TLC: Rf 0.36(n-hexane:ethyl acetate=2:1).

EXAMPLE 32(99)

N-(2-trifluoromethylthiobenzyl)-2,3,4,5-tetrahydro-1H-1-benzazepine-1-carboxamide TLC: Rf 0.44(n-hexane:ethyl acetate=2:1).

EXAMPLE 32(100)

N-(biphenyl-2-ylmethyl)-2,3,4,5-tetrahydro-1H-1-benzazepine-1-carboxamide

TLC:Rf 0.42(n-hexane:ethyl acetate=2:1).

EXAMPLE 32(101)

N-(2,3-difluorobenzyl)-2,3,4,5-tetrahydro-1H-1-benzazepine-1-carboxamide

TLC: Rf 0.36(n-hexane:ethyl acetate=2:1).

EXAMPLE 32(102)

N-(2,4-difluorobenzyl)-2,3,4,5-tetrahydro-1H-1-benzazepine-1-carboxamide

TLC:Rf 0.42(n-hexane:ethyl acetate=2:1).

EXAMPLE 32(103)

N-(2,5-difluorobenzyl)-2,3,4,5-tetrahydro-1H-1-benzazepine-1-carboxamide

TLC:Rf 0.47(n-hexane:ethyl acetate=2:1).

EXAMPLE 32(104)

N-(2,6-difluorobenzyl)-2,3,4,5-tetrahydro-1H-1-benzazepine-1-carboxamide

TLC:Rf 0.41(n-hexane:ethyl acetate=2:1).

EXAMPLE 32(105)

N-(3,5-difluorobenzyl)-2,3,4,5-tetrahydro-1H-1-benzazepine-1-carboxamide

TLC: Rf 0.41 (n-hexane:ethyl acetate=2:1).

EXAMPLE 32(106)

N-(3,4-difluorobenzyl)-2,3,4,5-tetrahydro-1H-1-benzazepine-1-carboxamide

TLC:Rf 0.31(n-hexane:ethyl acetate=2:1).

EXAMPLE 32(107)

N-[2-ethyl(3-methylphenyl)aminoethyl]-7-benzyloxy-2,3,4,5-tetrahydro-1H-1-benzazepine-1-carboxamide TLC:Rf 0.49(n-hexane:ethyl acetate=1:1);
NMR(CDCl$_3$):δ 1.06 (m, 3H), 1.28 (m, 1H), 1.80 (m, 1H), 1.91 (m, 2H), 2.29 (m, 3H), 2.61 (m, 3H), 3.28 (q, J=7.05 Hz, 2H), 3.36 (m, 4H), 4.48 (m, 2H), 5.03 (s, 2H), 6.48 (m, 3H), 6.71 (dd, J=8.52, 3.02 Hz, 1H), 6.84 (d, J=3.02 Hz, 1H), 6.96 (d, J=8.52 Hz, 1H), 7.06 (m, 1H), 7.38 (m, 5H).

EXAMPLE 32(108)

N-(4-benzyloxybenzyl)-8-fluoro-2,3,4,5-tetrahydro-1H-1-benzazepine-1-carboxamide TLC:Rf 0.74(n-hexane:ethyl acetate=2:1);
NMR(DMSO-$d_6$):δ 1.58 (m, 2H), 1.72 (m, 2H), 2.66 (m, 2H), 3.50 (m, 2H), 4.17 (d, J=6.04 Hz, 2H), 5.07 (s, 2H), 5.97 (m, 1H), 6.94 (m, 4H), 7.14 (m, 2H), 7.35 (m, 6H).

EXAMPLE 32(134)

N-(4-benzyloxybenzyl)-7-fluoro-2,3,4,5-tetrahydro-1H-1-benzazepine-1-carboxamide TLC:Rf 0.58 (n-hexane:ethyl acetate=1:1);
NMR(CDCl$_3$):δ 1.26 (m, 1H), 1.98 (m, 3H), 2.57 (m, 3H), 4.34 (m, 2H), 4.48 (m, 1H), 4.62 (m, 1H), 5.03 (s, 2H), 6.90 (m, 4H), 7.13 (m, 3H), 7.35 (m, 5H).

EXAMPLE 32(135)

N-(4-benzyloxybenzyl)-2,3,4,5-tetrahydro-1H-1-benzazepine-1-carboxamide

TLC:Rf 0.31 (n-hexane:ethyl acetate=2:1);
NMR(CDCl$_3$):δ 1.26 (m, 1H), 1.93 (m, 3H), 2.76 (m, 3H), 4.32 (m, 2H), 4.60 (m, 2H), 5.03 (s, 2H), 6.89 (m, 2H), 7.28 (m, 11H).

EXAMPLE 32(136)

N-[1-(2-methoxyphenyl)piperidin-4-yl]-2,3,4,5-tetrahydro-1H-1-benzazepine-1-carboxamide TLC: Rf 0.31 (n-hexane:ethyl acetate=3:2);
NMR(CDCl$_3$):δ 1.43 (m, 3H), 1.94 (m, 5H), 2.68 (m, 5H), 3.29 (d, J=11.26 Hz, 2H), 3.80 (m, 4H), 4.16 (d, J=8.24 Hz, 1H), 4.59 (s, 1H), 6.91 (m, 4H), 7.23 (m, 4H).

EXAMPLE 32(137)

1-[(2R)-6,6-dimethylbicyclo[3.1.1]heptan-2-ylmethylcarbamoyl]-2,3,4,5-tetrahydro-1H-1-benzazepine TLC:Rf 0.26(n-hexane:ethyl acetate=4:1).

EXAMPLE 32(138)

1-(2-methylcyclohexylcarbamoyl)-2,3,4,5-tetrahydro-1H-1-benzazepine

TLC:Rf 0.22(n-hexane:ethyl acetate=4:1).

EXAMPLE 32(139)

1-(3-methylcyclohexylcarbamoyl)-2,3,4,5-tetrahydro-1H-1-benzazepine

TLC:Rf 0.22(n-hexane:ethyl acetate=4:1).

EXAMPLE 32(140)

1-(4-methylcyclohexylcarbamoyl)-2,3,4,5-tetrahydro-1H-1-benzazepine

TLC:Rf 0.22 and 0.16(n-hexane:ethyl acetate=4:1).

EXAMPLE 32(141)

1-(2-furylmethylcarbamoyl)-2,3,4,5-tetrahydro-1H-1-benzazepine

TLC:Rf 0.11(n-hexane:ethyl acetate=4:1).

EXAMPLE 32(142)

1-(1-naphthyl methylcarbamoyl)-2,3,4,5-tetrahydro-1H-1-benzazepine

TLC:Rf 0.11(n-hexane:ethyl acetate=4:1).

EXAMPLE 32(143)

1-(tetrahydrofuran-2-ylmethylcarbamoyl)-2,3,4,5-tetrahydro-1H-1-benzazepine

TLC:Rf 0.61(chloroform: methanol=9:1).

EXAMPLE 32(144)

1-(2-hydroxy-2-phenylethylcarbamoyl)-2,3,4,5-tetrahydro-1H-1-benzazepine

TLC:Rf 0.48(chloroform: methanol=9:1).

EXAMPLE 32(145)

1-(1-propylbutylcarbamoyl)-2,3,4,5-tetrahydro-1H-1-benzazepine

TLC:Rf 0.30(n-hexane:ethyl acetate=4:1).

EXAMPLE 32(146)

1-(5-methylfuran-2-ylmethylcarbamoyl)-2,3,4,5-tetrahydro-1H-1-benzazepine

TLC:Rf 0.13(n-hexane:ethyl acetate=4:1).

EXAMPLE 32(147)

1-(1-methyl-3-phenylpropylcarbamoyl)-2,3,4,5-tetrahydro-1H-1-benzazepine

TLC:Rf 0.18(n-hexane:ethyl acetate=4:1).

EXAMPLE 32(148)

1-(2-methylbutylcarbamoyl)-2,3,4,5-tetrahydro-1H-1-benzazepine

TLC:Rf 0.30(n-hexane:ethyl acetate=3:1).

EXAMPLE 32(149)

1-(3-methylbutylcarbamoyl)-2,3,4,5-tetrahydro-1H-1-benzazepine

TLC:Rf 0.31(n-hexane:ethyl acetate=3:1).

EXAMPLE 32(150)

1-heptylcarbamoyl-2,3,4,5-tetrahydro-1H-1-benzazepine

TLC:Rf 0.31(n-hexane:ethyl acetate=3:1).

EXAMPLE 32(151)

1-[(1R)-1-(4-methylphenyl )ethylcarbamoyl]-2,3,4,5-tetrahydro-1H-1-benzazepine

TLC:Rf 0.24(n-hexane:ethyl acetate=3:1).

EXAMPLE 32(152)

1-[1-(4-fluorophenyl)ethylcarbamoyl]-2,3,4,5-tetrahydro-1H-1-benzazepine

TLC:Rf 0.18(n-hexane:ethyl acetate=3:1).

EXAMPLE 32(153)

1-(2-thienylmethylcarbamoyl)-2,3,4,5-tetrahydro-1H-1-benzazepine

TLC:Rf 0.17(n-hexane:ethyl acetate=3:1).

EXAMPLE 32(154)

1-(4-aminosulfonylbenzylcarbamoyl)-2,3,4,5-tetrahydro-1H-1-benzazepine

TLC:Rf 0.22(chloroform: methanol=9:1).

EXAMPLE 32(155)

1-(triazol-3-ylcarbamoyl)-2,3,4,5-tetrahydro-1H-1-benzazepine

TLC:Rf 0.53(chloroform: methanol=9:1).

EXAMPLE 32(156)

1-(benzimidazol-2-ylcarbamoyl)-2,3,4,5-etrahydro-1H-1-benzazepine

TLC:Rf 0.45(chloroform: methanol=9:1).

EXAMPLE 32(157)

1-[5-methylthio(triazol-3-yl)carbamoyl]-2,3,4,5-tetrahydro-1H-1-benzazepine

TLC:Rf 0.14(n-hexane:ethyl acetate=3:1).

EXAMPLE 32(158)

1-[1-methyl4-oxo(4,5-dihydroimidazol)-2-ylcalbamoyl]-2,3,4,5-tetrahydro-1H-1-benzazepine TLC:Rf 0.55(chloroform: methanol=9:1).

EXAMPLE 32(159)

1-[5-phenyl(pyrazol-3-yl)carbamoyl]-2,3,4,5-tetrahydro-1H-1-benzazepine

TLC:Rf 0.31(n-hexane:ethyl acetate=3:1).

EXAMPLE 32(160)

1-[4-methoxycarbonyl(thiophen-3-yl )carbamoyl]-2,3,4,5-tetrahydro-1H-1-benzazepine TLC:Rf 0.42(n-hexane:ethyl acetate=3:1).

EXAMPLE 32(161)

1-[4-methyl(pyrimidin-2-yl)carbamoyl]-2,3,4,5-tetrahydro-1H-1-benzazepine

TLC:Rf 0.52(chloroform: methanol=9:1).

EXAMPLE 32(162)

1-(quinolin-3-ylcalbamoyl)-2,3,4,5-tetrahydro-1H-1-benzazepine

TLC:Rf 0.69(chloroform: methanol=9:1).

EXAMPLE 33(1)-EXAMPLE 33(8)

Compounds of the present invention having the following physical properties values were obtained by operating as well as the method represented in Example 19, using the corresponding compound.

EXAMPLE 33(1)

N-(4,6-dimethylpyridin-2-yl)-2,3,4,5-tetrahydro-1H-1-benzazepine-1-carboxamide

TLC:Rf 0.36 (n-hexane:ethyl acetate=3:1);
NMR (CDCl$_3$):δ 7.83 (s, 1H), 7.31-7.22 (m, 4H), 6.88 (bs, 1H), 6.59 (s, 1H), 4.80-4.60 (br, 1H), 2.95-2.63 (br, 3H), 2.29 (s, 3H), 2.28 (s, 3H), 2.10-1.76 (br, 3H), 1.52-1.26 (br, 1H).

EXAMPLE 33(2)

N-(6-chloro-1,3-benzothiazol-2-yl)-2,3,4,5-tetrahydro-1H-1-benzazepine-1-carboxamide TLC:Rf 0.44 (n-hexane:ethyl acetate=3:1);
NMR (CDCl$_3$):δ 7.93 (bs, 1H), 7.75 (d, J=2.1 Hz, 1H), 7.49 (d, J=8.4 Hz, 1H), 7.35-7.27 (m, 5H), 4.68 (m, 1H), 2.88-2.72 (m, 3H), 2.09-1.85 (m, 3H), 2.40 (m, 1H).

EXAMPLE 33(3)

7-benzyloxy-N-(4-methoxymethoxy-2-methylphenyl)-2,3,4,5-tetrahydro-1H-1-benzazepine-1-carboxamide TLC:Rf 0.20(n-hexane:ethyl acetate=2:1);
NMR(CDCl$_3$):δ1.37 (m, 1H), 1.90 (m, 6H), 2.75 (m, 3H), 3.44 (s, 3H), 4.63 (d, J=12.64 Hz, 1H), 5.07 (m, 4H), 5.93

(s, 1H), 6.77 (d, J=2.75 Hz, 1H), 6.85 (m, 2H), 6.94 (d, J=3.02 Hz, 1H), 7.24 (m, 1H), 7.38 (m, 5H), 7.64 (d, J=8.79 Hz, 1H).

EXAMPLE 33(4)

7-benzyloxy-N-(4-methoxymethoxy-3-methylphenyl)-2,3,4,5-tetrahydro-1H-1-benzazepine-1-carboxamide TLC:Rf 0.30(n-hexane:ethyl acetate=2:1);
NMR(CDCl$_3$):δ 1.37 (m, 1H), 1.90 (m, 3H), 2.19 (s, 3H), 2.73 (m, 3H), 3.46 (s, 3H), 4.64 (d, J=13.46 Hz, 1H), 5.08 (s, 2H), 5.12 (s, 2H), 6.08 (s, 1H), 6.88 (m, 3H), 7.01 (m, 1H), 7.13 (d, J=2.75 Hz, 1H), 7.19 (d, J=8.52 Hz, 1H), 7.41 (m, 5H).

EXAMPLE 33(5)

7-methoxy-N-(4-methoxymethoxy-2-methylphenyl)-2,3,4,5-tetrahydro-1H-1-benzazepine-1-carboxamide TLC:Rf 0.26(n-hexane:ethyl acetate=2:1);
NMR(CDCl$_3$):δ 1.39 (m, 1H), 1.90 (m, 6H), 2.75 (m, 3H), 3.44 (s, 3H), 3.83 (s, 3H), 4.63 (d, J=13.74 Hz, 1H), 5.10 (s, 2H), 5.94 (s, 1H), 6.82 (m, 4H), 7.25 (d, J=7.69 Hz, 1H), 7.63 (d, J=8.79 Hz, 1H).

EXAMPLE 33(6)

7-methoxy-N-(4-methoxymethoxy-3-methylphenyl)-2,3,4,5-tetrahydro-1H-1-benzazepine-1-carboxamide TLC:Rf 0.31(n-hexane:ethyl acetate=2:1);
NMR(CDCl$_3$):δ1.37 (m, 1H), 1.84 (m, 3H), 2.19 (s, 3H), 2.71 (m, 3H), 3.46 (s, 3H), 3.84 (s, 3H), 4.64 (d, J=13.46 Hz, 1H), 5.12 (s, 2H), 6.08 (s, 1H), 6.78 (m, 1H), 6.84 (d, J=2.75 Hz, 1H), 6.91 (d, J=8.79 Hz, 1H), 7.01 (m, 1H), 7.13 (d, J=2.47 Hz, 1H), 7.20 (d, J=8.52 Hz, 1H).

EXAMPLE 33(7)

7-benzyloxy-N-(2-fluoro-4-methoxymethoxyphenyl)-2,3,4,5-tetrahydro-1H-1-benzazepine-1-carboxamide TLC:Rf 0.26(n-hexane:ethyl acetate=3:1);
NMR(CDCl$_3$):δ 1.40 (m, 1H), 1.89 (m, 3H), 2.75 (m, 3H), 3.44 (s, 3H), 4.63 (d, J=13.74 Hz, 1H), 5.08 (s, 2H), 5.09 (s, 2H), 6.29 (d, J=2.47 Hz, 1H), 6.72 (m, 1H), 6.78 (m, 1H), 6.86 (dd, J=8.52, 3.02 Hz, 1H), 6.93 (d, J=2.75 Hz, 1H), 7.22 (d, J=8.52 Hz, 1H), 7.41 (m, 5H), 7.97 (t, J=9.07 Hz, 1H).

EXAMPLE 33(8)

N-(5-methyl-1,3-thiazol-2-yl)-2,3,4,5-tetrahydro-1H-1-benzazepine-1-carboxamide

TLC:Rf 0.38(n-hexane:ethyl acetate=1:1);
NMR(CDCl$_3$):δ1.36 (m, 1H), 1.86 (m, 3H), 2.35 (m, 3H), 2.78 (m, 3H), 4.66 (d, J=14.01 Hz, 1H), 6.90 (d, J=1.37 Hz, 1H), 7.29 (m, 5H).

EXAMPLE 34

4-(2,3,4,5-tetrahydro-1H-1-benzazepin-1-ylcarbonylaminomethyl)phenoxyacetic acid A present compound having the following physical properties values was obtained by operating as well as the method sequentially represented in Example 14, 17, and 18, using the compound prepared in Example 32(135) instead of the compound prepared in Example 12(2).

TLC:Rf 0.39 (chloroform: methanol=5:1);
NMR(DMSO-d$_6$):δ 1.61 (m, 2H), 1.73 (m, 2H), 2.69 (m, 2H), 3.49 (m, 2H), 4.16 (d, J=6.04 Hz, 2H), 4.57 (m, 2H), 5.60 (m, 1H), 6.83 (m, 2H), 7.19 (m, 6H).

EXAMPLE 35

N-(2,3,4,5-tetrahydro-1H-1-benzazepin-1-ylcarbonyl)phenylalanine

A present compound having the following physical properties values was obtained by operating as well as the method represented in Example 18, using the compound prepared in Example 32(71) instead of the compound prepared in Example 17.

TLC:Rf 0.42 (ethyl acetate);
NMR (DMSO-d$_6$):δ 1.63 (m, 4H), 2.60 (m, 2H), 2.89 (dd, J=13.64, 7.96 Hz, 1H), 2.99 (m, 1H), 3.37 (m, 2H), 4.36 (m, 1H), 5.14 (m, 1H), 7.17 (m, 9H), 12.47 (m, 1H).

EXAMPLE 36(1)-EXAMPLE 36(8)

Compounds of the present invention having the following physical properties values were obtained by operating as well as the method represented in Example 11, using the compound prepared in Example 32(71) instead of 2,3,4,5-tetrahydro-1H-1-benzazepine.

EXAMPLE 36(1)

N-benzyl-2,3,4,5-tetrahydro-1H-1-benzazepine-1-carbothioamide

TLC:Rf 0.37 (ethyl acetate: n-hexane=1:4);
NMR (CDCl$_3$):δ1.41 (m, 1H), 1.80 (m, 1H), 2.01 (m, 1H), 2.32 (m, 1H), 2.71 (m, 2H), 2.98 (m, 1H), 4.76 (dd, J=15.11, 5.22 Hz, 1H), 4.94 (m, 1H), 5.41 (m, 1H), 5.62 (m, 1H), 7.24 (m, 9H).

EXAMPLE 36(2)

N-(4-fluorobenzyl)-2,3,4,5-tetrahydro-1H-1-benzazepine-1-carbothioamide

TLC:Rf 0.30 (ethyl acetate: n-hexane=1:4);
NMR (CDCl$_3$):δ 1.40 (m, 1H), 1.79 (m, 1H), 2.01 (m, 1H), 2.31 (m, 1H), 2.69 (m, 2H), 2.98 (m, 1H), 4.70 (dd, J=15.11, 4.94 Hz, 1H), 4.91 (m, 1H), 5.39 (m, 1H), 5.61 (m, 1H), 6.97 (m, 2H), 7.24 (m, 6H).

EXAMPLE 36(3)

N-(2-benzyloxybenzyl)-2,3,4,5-tetrahydro-1H-1-benzazepine-1-carbothioamide

TLC:Rf 0.68 (ethyl acetate: n-hexane=1:3);

NMR (CDCl$_3$):δ 1.33 (m, 1H), 1.74 (m, 1H), 1.94 (m, 1H), 2.25 (m, 1H), 2.60 (m, 2H), 2.90 (m, 1H), 4.80 (dd, J=13.91, 4.76 Hz, 1H), 4.91 (s, 2H), 4.99 (m, 1 H), 5.36 (m, 1H), 6.02 (m, 1H), 6.82 (d, J=8.42 Hz, 1H), 6.92 (t, J=6.96 Hz, 1H), 7.17 (m, 11H).

EXAMPLE 36(4)

N-(2-phenoxybenzyl)-2,3,4,5-tetrahydro-1H-1-benzazepine-1-carbothioamide

TLC:Rf 0.28 (n-hexane:ethyl acetate=9:1);

NMR (CDCl$_3$):δ 1.34 (m, 1H), 1.76 (m, 1H), 1.95 (m, 1H), 2.26 (m, 1H), 2.63 (m, 2H), 2.92 (t, J=12.63 Hz, 1H), 4.78 (dd, J=14.83, 5.31 Hz, 1H), 4.93 (m, 1H), 5.35 (d, J=13.55 Hz, 1H), 5.98 (t, J=4.94 Hz, 1H), 6.75 (m, 3H), 7.17 (m, 9H), 7.44 (dd, J=7.51, 1.65 Hz, 1H).

EXAMPLE 36(5)

N-(2-benzyloxy-4-chlorobenzyl)-2,3,4,5-tetrahydro-1H-1-benzazepine-1-carbothioamide TLC:Rf 0.30 (n-hexane:ethyl acetate=9:1);

NMR(CDCl$_3$):δ 1.33 (m, 1H), 1.75 (m, 1H), 1.96 (m, 1H), 2.23 (m, 1H), 2.61 (m, 2H), 2.90 (t, J=12.82 Hz, 1H), 4.72 (dd, J=14.83, 5.31 Hz, 1H), 4.94 (m, 3H), 5.34 (d, J=13.18 Hz, 1H), 5.92 (t, J=5.13 Hz, 1H), 6.83 (d, J=1.83 Hz, 1H), 6.91 (dd, J=7.87, 2.01 Hz, 1H), 7.19 (m, 10H).

EXAMPLE 36(6)

N-(2-chloro-4-fluorobenzyl)-2,3,4,5-tetrahydro-1H-1-benzazepine-1-carbothioamide TLC:Rf 0.40 (n-hexane:ethyl acetate=9:1);

NMR (CDCl$_3$):δ 1.36 (m, 1H), 1.79 (m, 1H), 1.99 (m, 1H), 2.27 (m, 1H), 2.70 (m, 2H), 2.96 (m, 1H), 4.68 (dd, J=15.01, 5.49 Hz, 1H), 4.96 (m, 1H), 5.33 (d, J=13.91 Hz, 1H), 5.85 (t, J=5.49 Hz, 1H), 6.94 (m, 1H), 7.05 (dd, J=8.42, 2.56 Hz, 1H), 7.13 (m, 1H), 7.28 (m, 3H), 7.45 (dd, J=8.42, 6.22 Hz, 1H).

EXAMPLE 36(7)

N-(4-benzyloxy-2-chlorobenzyl)-2,3,4,5-tetrahydro-1H-1-benzazepine-1-carbothioamide TLC:Rf 0.29 (n-hexane:ethyl acetate=9:1);

NMR (CDCl$_3$):δ 1.37 (m, 1H), 1.78 (m, 1H), 1.99 (m, 1H), 2.26 (m, 1H), 2.69 (m, 2H), 2.94 (t, J=12.45 Hz, 1H), 4.65 (dd, J=15.01, 5.49 Hz, 1H), 4.92 (m, 1H), 5.01 (s, 2H), 5.3 5 (d, J=13.55 Hz, 1H), 5.81 (t, J=5.68 Hz, 1H), 6.82 (dd, J=8.42, 2.56 Hz, 1H), 6.93 (d, J=2.20 Hz, 1H), 7.13 (m, 1H), 7.30 (m, 9H).

EXAMPLE 36(8)

N-{2-[methyl(phenyl)amino]benzyl}-2,3,4,5-tetrahydro-1H-1-benzazepine-1-carbothioamide TLC:Rf 0.69 (ethyl acetate: n-hexane=1:2);

NMR (CDCl$_3$):δ 1.33 (m, 1H), 1.76 (m, 1H), 1.95 (m, 1H), 2.26 (m, 1H), 2.63 (m, 2H), 2.91 (m, 1H), 3.03 (m, 3H), 4.74 (m, 2H), 5.37 (m, 1H), 5.83 (m, 1H), 6.38 (m, 2H), 6.70 (m, 1H), 7.06 (m, 4H), 7.24 (m, 5H), 7.42 (m, 1H).

EXAMPLE 37

N-(4-hydroxyphenyl)-5-hydroxy-2,3,4,5-tetrahydro-1H-1-benzazepine-1-carboxamide

A present compound having the following physical properties values was obtained by operating as well as the method sequentially represented in examples 12, 14, and 2, using the compound prepared in Reference example 6 instead of 2,3,4,5-1H-tetrahydro benzazepine and 4-benzyloxy benzoic acid instead of 3-cyclohexyl propionate.

TLC:Rf 0.39 (methylene chloride: methanol=10:1);

NMR(CDCl$_3$+CD$_3$OD):δ 7.80-7.68 (m, 1H), 7.49-7.26 (m, 3H), 7.08-7.01 (m, 2H), 6.75-6.68 (m, 2H), 6.25 (brs, 1H), 4.90-4.83 (m, 1H), 4.64-4.41 (m, 1H), 2.81-2.57 (m, 1H), 2.12-1.96 (m, 2H), 1.83-1.49 (m, 2H).

EXAMPLE 38

2,3,4,5-tetrahydro-1H-1-benzazepine-1-carboxamide

A present compound having the following physical properties values was obtained by operating as well as the method represented in Example 9, using 2,3,4,5-tetrahydro-1H-1-benzazepine instead of the compound preparred in Reference example 12.

TLC:Rf 0.29 (ethyl acetate);

NMR (CDCl$_3$):δ 1.34 (m, 1H), 1.90 (m, 3H), 2.75 (m, 3H), 4.34 (m, 2H), 4.59 (m, 1H), 7.25 (m, 4H).

REFERENCE EXAMPLE 22

1-toluenesulfonyl-2H,3H,4H,1aH,8bH-benzo[f]oxirane[2,3-d]azaperhydroepine

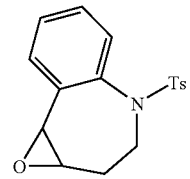

A mixture of which 3-chloroperbenzoic acid (2.89 g) had been added to methylene chloride (10 ml) solution of 1-toluenesulfonyl-2,3,4,5-tetrahydrobenzazepine (2.0 g) during storage in ice was stirred at room temperature for 5 hours. The reactive mixture to which water had been added was extracted by ethyl acetate. The organic layer sequentially washed with saturated sodium thiosulfate solution, saturated sodium bicarbonate solution, and saturated brine was concentrated after drying with sulfuric anhydride magnesium. A title compound (2.395 g) having the following physical properties values was obtained.

TLC:Rf 0.43 (n-hexane:ethyl acetate=2:1).

REFERENCE EXAMPLE 23

4-hydroxy-1-toluenesulfonyl-2,3,4,5-tetrahydro-1H-1-benzazepine

A mixture of which the compound (2.29 g) prepared in above Reference example 22 had been added to tetrahydrofuran (10 ml) suspension of lithium aluminum hydride (254 mg) during storage in ice was stirred at room temperature for 1 hour. Saturated sodium sulfate solution (1.25 ml) was added to the reactive mixture stored in ice. The filtrate was concentrated after remove of the deposit by filtration. A title compound (2.351 g) having the following physical properties values was obtained.

TLC:Rf 0.15 (n-hexane:ethyl acetate=2:1).

REFERENCE EXAMPLE 24

4-oxo-1-toluenesulfonyl-2,3,4,5-tetrahydro-1H-1-benzazepine

A mixture of which triethylamine (2.8 ml) and sulfur trioxide/pyridine complex (3.19 g) had been added to dichloromethane (7 ml)-dimethyl sulphoxide (7 ml) solution of the compound (2.35 g) prepared in above Reference example 23 during storage in ice was stirred at room temperature for 90 minutes. The reactive mixture to which water had been added was extracted by ethyl acetate. The organic layer sequentially washed with 1 N hydrochloric acid, saturated sodium bicarbonate solution, and saturated brine was concentrated after drying with sulfuric anhydride magnesium. The obtained residue was purified by silica gel column chromatography (n-hexane:ethyl acetate=3:1 to 2:1). A title compound (1.58 g) having the following physical properties values was obtained.

TLC:Rf 0.43 (n-hexane:ethyl acetate=2:1);
NMR(CDCl$_3$):δ 2.44 (s, 3H), 2.67 (m, 2H), 3.34 (s, 2H), 3.96 (dd, J=7.14, 5.49 Hz, 2H), 7.16 (m, 1H), 7.29 (m, 5H), 7.65 (d, J=8.52 Hz, 2H).

REFERENCE EXAMPLE 25

1-toluenesulfonyl-2,3,4,5-tetrahydro-1H-1-benzazepine-4-oxideethylene ketal

A mixture of which ethylene glycol (0.28 ml) and toluenesulfonic acid (24 mg) had been added to benzene (10 ml) solution of the compound (787 mg) prepared in above Reference example 24 was refluxed for 90 minutes. The reactive mixture to which water had been added at room temperature was extracted by ethyl acetate. The organic layer sequentially washed with saturated sodium bicarbonate solution and saturated brine was concentrated after drying with sulfuric anhydride magnesium. A title compound having the following physical properties values was obtained.

TLC:Rf 0.41 (n-hexane:ethyl acetate=2:1);
NMR(CDCl$_3$):δ 1.96 (m, 2H), 2.41 (s, 3H), 2.54 (s, 2H), 3.89 (m, 6H), 7.22 (m, 6H), 7.59 (d, J=8.52 Hz, 2H).

REFERENCE EXAMPLE 26

2,3,4,5-tetrahydro-1H-1-benzazepine-4-oxide ethylene ketal

The mixture of which magnesium powder (304 mg) had been added to methanol (10 ml) suspension of the compound (921 mg) prepared in the above Reference example 25 at 70° C. was stirred over night. The mixture to which magnesium powder (150 mg) had been added was stirred for 3 hours. In addition, magnesium powder (150 mg) was added, and was stirred for 3 hours. The residue obtained from the concentrated reactive mixture was suspended in methylene chloride, and was filtered. The filtrate was concentrated. A title compound (488 mg) having the following physical properties values was obtained.

TLC:Rf 0.56 (n-hexane:ethyl acetate=1:1).

EXAMPLE 39

N-(4-fluorobenzyl)-2,3-dihydrospiro[1-benzazepine-4,2'-[1,3]dioxolane]-1(5H)-carboxamide

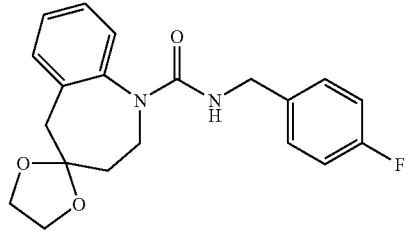

A present compound having the following physical properties values was obtained by operating as well as the method represented in Example 1, using the compound prepared in the above Reference example 26.

TLC:Rf 0.30 (n-hexane:ethyl acetate=1:1);
NMR(DMSO-d$_6$): δ 1.84 (m, 2H), 2.87 (s, 2H), 3.89 (m, 4H), 4.16 (d, J=5.77 Hz, 2H), 6.33 (t, J=5.91 Hz, 1H), 7.19 (m, 8H).

EXAMPLE 40

N-(4-fluorobenzyl)-4-oxo-2,3,4,5-tetrahydro-1H-1-benzazepine-1-carboxamide

A mixture of which 2N hydrochloric acid (1 ml) had been added to methanol (5 ml) solution of the compound (120 mg) prepared in above Example 39 at room temperature was stirred at room temperature over night. The reactive mixture to which ice water had been added was extracted by ethyl acetate. The organic layer sequentially washed with 1N hydrochloric acid, saturated sodium bicarbonate solution, and saturated brine was concentrated after drying with sulfuric anhydride magnesium. The obtained residue was recrystallized from n-hexane/ethyl acetate. The present compound having the following physical properties values was obtained.

TLC:Rf 0.27 (n-hexane:ethyl acetate=1:1);
NMR(CDCl$_3$): δ 2.74 (m, 2H), 3.68 (m, 2H), 4.37 (d, J=5.77 Hz, 2H), 4.74 (t, J=5.91 Hz, 1H), 6.99 (m, 2H), 7.27 (m, 6H).

EXAMPLE 41

N-(4-fluorobenzyl)-4-hydroxy-2,3,4,5-tetrahydro-1H-1-benzazepine-1-carboxamide

A mixture of which 2N hydrochloric acid had been added to methanol (1 ml) solution of the compound (47 mg) prepared in above Example 40 at room temperature was stirred at room temperature over night. The reactive mixture to which ice water had been added was extracted by ethyl acetate. The organic layer sequentially washed with 1N hydrochloric acid, saturated sodium bicarbonate solution, and saturated brine was concentrated after drying with sulfuric anhydride magnesium. The obtained residue was purified by silica gel column chromatography (n-hexane: ethyl acetate=1:3 to 1:4). The present compound having the following physical properties values was obtained.

TLC:Rf 0.29 (ethyl acetate: n-hexane=3:1);
NMR (DMSO-$d_6$): δ 1.72 (m, 1H), 1.87 (m, 1H), 2.78 (m, 2H), 3.19 (m, 1H), 3.69 (m, 1H), 3.84 (m, 1H), 4.21 (d, J=6.04 Hz, 2H), 4.36 (s, 1H), 5.82 (s, 1H), 7.15 (m, 8H).

EXAMPLE 42(1)-EXAMPLE 42(33)

Compounds of the present invention having the following physical properties values were obtained by operating as well as the method represented in Example 14, using the corresponding compound instead of the compound prepared in Example 12(2).

EXAMPLE 42(1)

N-(4-hydroxyphenyl)-8-fluoro-2,3,4,5-tetrahydro-1H-1-benzazepine-1-carboxamide

TLC: Rf 0.41 (n-hexane:ethyl acetate=1:1);
NMR(DMSO-$d_6$):δ 9.01 (s, 1H), 7.65 (s, 1H), 7.35-7.28 (m, 1H), 7.16-7.09 (m, 2H), 7.07-6.99 (m, 2H), 6.63-6.57 (m, 2H), 3.74-3.36 (m, 2H), 2.75-2.64 (m, 2H), 1.76-1.64 (m, 2H), 1.63-1.49 (m, 2H).

EXAMPLE 42(2)

N-(4-hydroxyphenyl)-9-methyl-2,3,4,5-tetrahydro-1H-1-benzazepine-1-carboxamide

TLC:Rf 0.37 (n-hexane:ethyl acetate=1:1);
NMR(CDCl$_3$):δ 7.21-7.12 (m, 3H), 7.00-6.95 (m, 2H), 6.75 (s, 1H), 6.66-6.60 (m, 2H), 5.88 (s, 1H), 4.63 (m, 1H), 2.87 (m, 1H), 2.74-2.59 (m, 2H), 2.31 (s, 3H), 2.14-1.99 (m, 2H), 1.77 (m, 1H), 1.35 (m, 1H).

EXAMPLE 42(3)

N-(4-hydroxyphenyl)-6-methyl-2,3,4,5-tetrahydro-1H-1-benzazepine-1-carboxamide

TLC:Rf 0.38 (n-hexane:ethyl acetate=1:1);
NMR(CDCl$_3$):δ 7.17-7.13 (m, 3H), 7.05-7.00 (m, 2H), 6.70-6.62 (m, 2H), 6.44 (s, 1H), 6.07 (s, 1H), 4.59 (d, J=13.8 Hz, 1H), 3.00 (dd, J=13.8, 6.0 Hz, 1H), 2.77-2.56 (m, 2H), 2.39 (s, 3H), 2.08-1.98 (m, 2H), 1.74 (m, 1H), 1.30 (m, 1H).

EXAMPLE 42(4)

7-fluoro-N-(4-hydroxyphenyl)-2,3,4,5-tetrahydro-1H-1-benzazepine-1-carboxamide

TLC:Rf 0.38 (n-hexane:ethyl acetate=1:1);
NMR(CDCl$_3$):δ 1.37 (m, 1H), 1.92 (m, 3H), 2.74 (m, 3H), 4.64 (m, 1H), 5.98 (s, 1H), 6.40 (s, 1H), 6.65 (m, 2H), 7.00 (m, 4H), 7.28 (dd, J=8.52, 5.22 Hz, 1H).

EXAMPLE 42(5)

N-(4-hydroxyphenyl)-5-methyl-2,3,4,5-tetrahydro-1H-1-benzazepine-1-carboxamide

TLC:Rf 0.37 (ethyl acetate: n-hexane=1:1);
NMR (CD$_3$OD):δ 1.33 (m, 3H), 2.00 (m, 4H), 2.88 (m, 2H), 4.49 (m, 1H), 6.67 (m, 2H), 7.04 (m, 2H), 7.31 (m, 4H).

EXAMPLE 42(6)

N-(4-aminophenyl)-7-methyl-2,3,4,5-tetrahydro-1H-1-benzazepine-1-carboxamide

TLC: Rf 0.26 (dichloromethane:ethyl acetate=1:1);
NMR (CDCl$_3$):δ 7.17 (d, J=8.7 Hz, 1H), 7.11-7.05 (m, 4H), 6.60-6.57 (m, 2H), 6.03 (s, 1H), 4.83-4.48 (br, 1H), 3.48 (bs, 2H), 2.95-2.50 (br, 3H), 2.36 (s, 3H), 2.10-1.70 (br, 3H), 1.48-1.22 (br, 1H).

EXAMPLE 42(7)

N-(4-aminophenyl)-7-hydroxy-2,3,4,5-tetrahydro-1H-1-benzazepine-1-carboxamide

TLC:Rf 0.38 (ethyl acetate);
NMR (CDCl$_3$:CD$_3$OD=2:1):δ 7.11 (d, J=8.4 Hz, 1H), 7.04-6.99 (m, 2H), 6.78 (d, J=2.7 Hz, 1H), 6.72 (dd, J=8.4, 2.7 Hz, 1H), 6.68-6.63 (m, 2H), 6.26 (s, 1H), 4.52 (m, 1H), 2.82-2.67 (m, 3H), 1.96-1.81 (m, 3H), 1.37 (m, 1H).

EXAMPLE 42(8)

N-(4-aminophenyl)-7-methoxy-2,3,4,5-tetrahydro-1H-1-benzazepine-1-carboxamide

TLC:Rf 0.43 (ethyl acetate);
NMR (CDCl$_3$):δ 7.20 (d, J=8.7 Hz, 1H), 7.09-7.04 (m, 2H), 6.83 (d, J=2.7 Hz, 1H), 6.75 (dd, J=8.4, 3.0 Hz, 1H), 6.61-6.56 (m, 2H), 6.02 (s, 1H), 4.64 (m, 1H), 3.83 (s, 3H), 3.48 (s, 2H), 2.87-2.59 (m, 3H), 1.99-1.78 (m, 3H), 1.35 (m, 1H).

EXAMPLE 42(9)

7-hydroxy-N-(4-hydroxy-2-methyl phenyl)-2,3,4,5-tetrahydro-1H-1-benzazepine-1-carboxamide TLC:Rf 0.27 (n-hexane:ethyl acetate=1:2);
NMR (CD$_3$OD):δ 7.14 (d, J=8.4 Hz, 1H), 7.05 (d, J=8.4 Hz, 1H), 6.75 (d, J=2.7 Hz, 1H), 6.70 (dd, J=8.4, 2.7 Hz, 1H), 6.58 (d, J=2.7 Hz, 1H), 6.55 (dd, J=8.4, 2.7 Hz, 1H), 4.58-4.38 (br, 1H), 2.90-2.55 (br, 3H), 2.03-1.79 (m, 6H), 1.50-1.26 (br, 1H).

EXAMPLE 42(10)

7-hydroxy-N-(4-hydroxy-3-methylphenyl)-2,3,4,5-tetrahydro-1H-1-benzazepine-1-carboxamide TLC: Rf 0.31 (n-hexane:ethyl acetate=1:1);
NMR (CD$_3$OD):δ 7.08 (d, J=8.4 Hz, 1H), 6.92 (d, J=2.7 Hz, 1H), 6.87 (dd, J=8.4, 2.7 Hz, 1H), 6.74 (d, J=2.7 Hz, 1H), 6.69 (dd, J=8.4, 2.7 Hz, 1H), 6.62 (d, J=8.4 Hz, 1H), 4.70-4.30 (br, 1H), 2.90-2.50 (br, 3H), 2.12 (s, 3H), 2.09-1.69 (br, 3H), 1.52-1.20 (br, 1H).

EXAMPLE 42(11)

6-fluoro-N-(4-hydroxyphenyl)-2,3,4,5-tetrahydro-1H-1-benzazepine-1-carboxamide

TLC:Rf 0.36 (ethyl acetate: n-hexane=1:1);
NMR (DMSO-d$_6$):δ 1.59 (m, 2H), 1.72 (m, 2H), 2.74 (m, 2H), 3.58 (m, 2H), 6.60 (m, 2H), 7.04 (t, J=7.69 Hz, 1H), 7.12 (m, 3H), 7.22 (m, 1H), 7.63 (s, 1H), 9.00 (s, 1H).

EXAMPLE 42(12)

N-(4-hydroxy-2-methylphenyl)-7-methoxy-2,3,4,5-tetrahydro-1H-1-benzazepine-1-carboxamide TLC:Rf 0.19 (n-hexane:ethyl acetate=1:1);
NMR (CDCl$_3$):δ 7.26 (d, J=8.4 Hz, 1H), 7.07-7.04 (m, 2H), 6.84 (d, J=3.0 Hz, 1H), 6.78 (dd, J=8.4, 3.0 Hz, 1H), 6.44-6.41 (m, 2H), 5.81 (s, 1H), 4.62 (m, 1H), 3.82 (s, 3H), 2.92-2.63 (m, 3H), 2.02-1.77 (m, 6H), 1.38 (m, 1H).

EXAMPLE 42(13)

N-(4-hydroxy-3-methylphenyl)-7-methoxy-2,3,4,5-tetrahydro-1H-1-benzazepine-1-carboxamide TLC:Rf 0.29 (n-hexane:ethyl acetate=1:1);
NMR (CDCl$_3$):δ 7.21 (d, J=8.4 Hz, 1H), 6.98 (d, J=2.4 Hz, 1H), 6.89 (dd, J=8.4, 2.4 Hz,1H), 6.83 (d, J=3.0 Hz, 1H), 6.78 (dd, J=8.4, 3.0 Hz, 1H), 6.58 (d, J=8.4 Hz, 1H), 6.03 (s, 1H), 5.60 (bs, 1H), 4.63 (m, 1H), 3.83 (s, 3H), 2.88-2.60 (m, 3H), 2.15 (s, 3H), 2.00-1.76 (m, 3H), 1.36 (m, 1H).

EXAMPLE 42(14)

N-(2-fluoro4-hydroxyphenyl)-7-hydroxy-2,3,4,5-tetrahydro-1H-1-benzazepine-1-carboxamide TLC:Rf 0.21 (n-hexane:ethyl acetate=1:1);
NMR (CD$_3$OD):δ 7.31 (t, J=9.0 Hz, 1H), 7.11 (d, J=8.1 Hz, 1H), 6.74 (d, J=2.7 Hz, 1H), 6.69 (dd, J=8.1, 2.7 Hz, 1H), 6.54-6.47 (m, 2H), 4.57-4.37 (br, 1H), 2.83-2.67 (m, 3H), 1.98-1.78 (m, 3H), 1.48-1.26 (br, 1H).

EXAMPLE 42(15)

N-(3-fluoro-4-hydroxyphenyl)-7-hydroxy-2,3,4,5-tetrahydro-1H-1-benzazepine-1-carboxamide TLC: Rf 0.32 (n-hexane:ethyl acetate=1:1);
NMR (CD$_3$OD):δ 7.16 (m, 1H), 7.06 (d, J=8.4 Hz,1H), 6.79-6.67 (m, 4H), 4.62-4.38 (br, 1H), 2.86-2.48 (br, 3H), 2.10-1.66 (br, 3H), 1.54-1.22 (br, 1H).

EXAMPLE 42(16)

7-hydroxy-N-(4-hydroxy-3-methoxyphenyl)-2,3,4,5-tetrahydro-1H-1-benzazepine-1-carboxamide TLC:Rf 0.31 (n-hexane:ethyl acetate=1:2);
NMR (CD$_3$OD):δ 7.08 (d, J=8.1 Hz, 1H), 6.98 (d, J=2.4 Hz, 1H), 6.75-6.57 (m, 4H), 4.65-4.38 (br, 1H), 3.80 (s, 3H), 2.85-2.50 (br, 3H), 2.10-1.70 (br, 3H), 1.50-1.26 (br, 1H).

EXAMPLE 42(17)

7-amino-N-(4-hydroxyphenyl)-2,3,4,5-tetrahydro-1H-1-benzazepine-1-carboxamide

TLC:Rf 0.32 (ethyl acetate: n-hexane=2:1);
NMR (CDCl$_3$):δ 1.28 (m, 1H), 1.95 (m, 3H), 2.64 (m, 3H), 4.56 (m, 1H), 6.20 (s, 1H), 6.56 (m, 1H), 6.62 (d, J=2.75 Hz, 1H), 6.71 (m, 2H), 7.06 (m, 3H).

EXAMPLE 42(18)

N-(4-hydroxyphenyl)-5,5-dimethyl-2,3,4,5-tetrahydro-1H-1-benzazepine-1-carboxamide TLC:Rf 0.33 (ethyl acetate: n-hexane=1:1);
NMR (CDCl$_3$):δ 1.30 (s, 3H), 1.46 (s, 3H), 1.54 (m, 1H), 1.71 (m, 2H), 2.23 (m, 1H), 2.67 (m, 1H), 4.71 (m, 1H), 6.10 (m, 2H), 6.64 (m, 2H), 7.01 (m, 2H), 7.30 (m, 3H), 7.50 (m, 1H).

EXAMPLE 42(19)

N-(4-aminophenyl)-7-fluoro-2,3,4,5-tetrahydro-1H-1-benzazepine-1-carboxamide

TLC:Rf 0.26 (ethyl acetate: n-hexane=2:1);
NMR (CDCl$_3$):δ 1.36 (m, 1H), 1.92 (m, 3H), 2.73 (m, 3H), 3.51 (s, 2H), 4.67 (m, 1H), 5.93 (s, 1H), 6.60 (m, 2H), 6.96 (td, J=8.31, 2.88 Hz, 1H), 7.04 (m, 3H), 7.27 (m, 1H).

EXAMPLE 42(20)

N-benzyl-7-hydroxy-2,3,4,5-tetrahydro-1H-1-benzazepine-1-carboxamide

TLC:Rf 0.42 (n-hexane:ethyl acetate=1:1);
NMR (CD$_3$OD):δ 1.34 (m, 1H), 1.86 (m, 3H), 2.65 (m, 3H), 4.34 (m, 3H), 5.81 (s, 1H), 6.64 (dd, J=8.24, 2.75 Hz, 1H), 6.69 (d, J=2.75 Hz, 1H), 6.99 (d, J=8.52 Hz, 1H), 7.22 (m, 5H).

EXAMPLE 42(21)

N-(4-hydroxybenzyl)-2,3,4,5-tetrahydro-1H-1-benzazepine-1-carboxamide

TLC:Rf 0.38 (n-hexane:ethyl acetate=1:2);
NMR (CDCl$_3$):δ 7.27-7.16 (m, 4H), 7.05-7.00 (m, 2H), 6.76-6.71 (m, 2H), 6.67 (s, 1H), 4.65-4.61 (m, 2H), 4.40-4.26 (br, 2H), 2.90-2.50 (br, 3H), 2.14-1.72 (br, 3H), 1.50-1.20 (br, 1H).

EXAMPLE 42(22)

N-(4-fluorobenzyl)-7-hydroxy-2,3,4,5-tetrahydro-1H-1-benzazepine-1-carboxamide

TLC: Rf 0.29 (n-hexane:ethyl acetate=1:1);
NMR (CD$_3$OD):δ 1.28 (m, 1H), 1.83 (m, 3H), 2.61 (m, 3H), 4.25 (s, 2H), 4.43 (m, 1H), 5.88 (m, 1H), 6.64 (dd, J=8.24, 2.75 Hz, 1H), 6.69 (d, J=2.75 Hz, 1H), 6.99 (m, 3H), 7.22 (m, 2H).

EXAMPLE 42(23)

N-{2-[ethyl(3-methylphenyl)-2-amin]oethyl}-7-hydroxy-2,3,4,5-tetrahydro-1H-1-benzazepine-1-carboxamide TLC: Rf 0.45 (n-hexane:ethyl acetate=1:1);
NMR (CDCl$_3$):δ 1.07 (t, J=7.00 Hz, 3H), 1.27 (m, 1H), 1.82 (m, 3H), 2.28 (s, 3H), 2.57 (m, 3H), 3.30 (m, 6H), 4.50 (m, 2H), 5.29 (m, 1H), 6.49 (m, 3H), 6.59 (dd, J=8.38, 2.88 Hz, 1H), 6.70 (d, J=3.02 Hz, 1H), 6.90 (d, J=8.24 Hz, 1H), 7.06 (m, 1H).

EXAMPLE 42(24)

8-fluoro-N-(4-hydroxybenzyl)-2,3,4,5-tetrahydro-1H-1-benzazepine-1-carboxamide

TLC: Rf 0.57 (n-hexane:ethyl acetate=2:1);
NMR (DMSO-d$_6$):δ 1.57 (m, 2H), 1.71 (m, 2H), 2.66 (m, 2H), 3.49 (m, 2H), 4.12 (d, J=5.77 Hz, 2H), 5.91 (m, 1H), 6.67 (m, 2H), 6.98 (m, 4H), 7.27 (dd, J=8.38, 6.46 Hz, 1H).

EXAMPLE 42(25)

N-(2-hydroxypyridin-5-yl)-2,3,4,5-tetrahydro-1H-1-benzazepine-1-carboxamide

TLC:Rf 0.50 (methanol: ethyl acetate=1:9);
NMR (DMSO-d$_6$):δ 1.62 (m, 2H), 1.75 (m, 2H), 2.74 (m, 2H), 3.54 (m, 2H), 6.23 (dd, J=9.34, 0.82 Hz, 1H), 7.11 (s, 1H), 7.24 (m, 4H), 7.39 (m, 2H), 10.80 (m, 1H).

EXAMPLE 42(26)

7-amino-N-phenyl-2,3,4,5-tetrahydro-1H-1-benzazepine-1-carboxamide

TLC:Rf 0.38 (ethyl acetate: n-hexane=1:1);
NMR (CDCl$_3$):δ 1.32 (m, 1H), 1.91 (m, 3H), 2.66 (m, 3H), 3.77 (s, 2H), 4.63 (m, 1H), 6.33 (s, 1H), 6.55 (m, 1H), 6.60 (d, J=2.75 Hz, 1H), 6.96 (m, 1H), 7.05 (d, J=7.97 Hz, 1H), 7.23 (m, 2H), 7.30 (m, 2H).

EXAMPLE 42(27)

5-fluoro-N-(4-hydroxyphenyl)-2,3,4,5-tetrahydro-1H-1-benzazepine-1-carboxamide

TLC:Rf 0.29 (ethyl acetate: n-hexane=1:1);
NMR (CDCl$_3$):δ 2.05 (m, 5H), 4.60 (m, 1H), 5.66 (m, 2H), 6.05 (s, 1H), 6.67 (m, 2H), 7.05 (m, 2H), 7.38 (m, 4H).

EXAMPLE 42(28)

7-fluoro-N-(4-hydroxybenzyl)-2,3,4,5-tetrahydro-1H-1-benzazepine-1-carboxamide

TLC:Rf 0.54 (n-hexane:ethyl acetate=1:2);
NMR (DMSO-d$_6$):δ 1.61 (m, 2H), 1.70 (m, 2H), 2.66 (m, 2H), 3.47 (m, 2H), 4.11 (d, J=5.77 Hz, 2H), 5.64 (s, 1H), 6.67 (m, 2H), 6.98 (m, 3H), 7.07 (dd, J=9.48, 2.88 Hz, 1H), 7.15 (dd, J=8.52, 5.49 Hz, 1H), 8.78 (m, 1H).

EXAMPLE 42(29)

7-hydroxy-N-(2-methoxy-4-methoxymethoxyphenyl)-2,3,4,5-tetrahydro-1H-1-benzazepine-1-carboxamide TLC:Rf 0.33 (n-hexane:ethyl acetate=1:1);
NMR(CDCl$_3$):δ 1.36 (m, 1H), 1.88 (m, 3H), 2.71 (m, 3H), 3.46 (s, 3H), 3.62 (s, 3H), 4.62 (d, J=13.46 Hz, 1H), 5.10 (s, 2H), 5.42 (s, 1H), 6.49 (d, J=2.47 Hz, 1H), 6.61 (dd, J=8.79, 2.47 Hz, 1H), 6.75 (m, 3H), 7.16 (d, J=8.24 Hz, 1H), 8.04 (d, J=9.07 Hz, 1H).

EXAMPLE 42(30)

N-(2-fluoro-4-methoxymethoxyphenyl)-7-hydroxy-2,3,4,5-tetrahydro-1H-1-benzazepine-1-carboxamide TLC:Rf 0.20(n-hexane:ethyl acetate=2:1);
NMR(CDCl$_3$):δ1.37 (m, 1H), 1.90 (m, 3H), 2.70 (m, 3H), 3.44 (s, 3H), 4.61 (d, J=13.19 Hz, 1H), 5.08 (s, 2H), 5.68 (s, 1H), 6.30 (d, J=2.20 Hz, 1H), 6.74 (m, 4H), 7.16 (d, J=8.24 Hz, 1H), 7.94 (t, J=9.07 Hz, 1H).

EXAMPLE 42(31)

N-(3-fluoro4-methoxymethoxyphenyl)-7-hydroxy-2,3,4,5-tetrahydro-1H-1-benzazepine-1-carboxamide TLC:Rf 0.38 (n-hexane:ethyl acetate=1:1);
NMR(CDCl$_3$):δ 1.38 (m, 1H), 1.91 (m, 3H), 2.72 (m, 3H), 3.49 (s, 3H), 4.62 (d, J=14.28 Hz, 1H), 5.12 (s, 2H), 5.26 (s, 1H), 6.18 (s, 1H), 6.73 (dd, J=8.24, 2.75 Hz, 1H), 6.79 (m, 2H), 7.02 (t, J=8.93 Hz, 1H), 7.13 (d, J=8.52 Hz, 1H), 7.34 (dd, J=13.19, 2.47 Hz, 1H).

EXAMPLE 42(32)

5-(t-butyldimethylsilyloxy)-N-(4-hydroxyphenyl)-2,3,4,5-tetrahydro-1H-1-benzazepine-1-carboxamide TLC: Rf 0.16(n-hexane:ethyl acetate=3:1);
NMR(CDCl$_3$):δ 7.72-7.67 (m, 1H), 7.45-7.24 (m, 3H), 7.04-6.97 (m, 2H), 6.69-6.63 (m, 2H), 6.03 (brs, 1H), 4.91-4.83 (m, 1H), 4.61-4.48 (m, 1H), 2.73-2.58 (m, 1H), 2.09-1.99 (m, 2H), 1.75-1.51 (m, 2H), 0.96 (s, 9H), 0.17 (s, 6H).

EXAMPLE 42(33)

N-(4-hydroxyphenyl )-5-methyl-2,3-dihydro-1H-1-benzazepine-1-carboxamide

TLC:Rf 0.32(n-hexane:ethyl acetate=1:1).

REFERENCE EXAMPLE 27

3-(2-nitrophenyloxy)propionate

To 1N sodium hydroxide solution (100 ml) of o-nitrophenol (6.96 g), 3-bromopropionate (7.65 g) had been added and was stirred at 50° C. over night, and followed by stirring at 70° C. for 3 hours. The reactive mixture to which ice had been added was adjusted to pH 7 with 1N hydrochloric acid. Ethyl acetate was added to the mixture, which was separated. The water layer was adjusted to pH 2 with 1N hydrochloric acid. The water layer was extracted by ethyl acetate and the organic layer was washed with saturated brine, and then both were concentrated after drying with sulfuric anhydride magnesium. The obtained residue was recrystallized from n-hexane/ethyl acetate. A title compound (1.01 g) having the following physical properties values was obtained.

TLC:Rf 0.46 (methylene chlorid: methanol=9:1);
NMR(CDCl$_3$):δ 2.94 (t, J=6.32 Hz, 2H), 4.40 (t, J=6.32 Hz, 2H), 7.06 (ddd, J=8.38, 7.14, 1.24 Hz, 1H), 7.12 (dd, J=8.52, 1.10 Hz, 1H), 7.54 (ddd, J=8.72, 7.07, 1.79 Hz, 1H), 7.84 (dd, J=8.10, 1.79 Hz, 1H).

REFERENCE EXAMPLE 28

3-(2-aminophenyloxy)propionate

A present compound having the following physical properties values was obtained by operating as well as the method represented in Example 14, using the compound prepared in the above Reference example 27.

TLC:Rf 0.43 (methylene chlorid: methanol=9:1);
NMR(CDCl$_3$):δ 2.84 (t, J=6.18 Hz, 2H), 4.27 (t, J=6.04 Hz, 2H), 6.77 (m, 4H).

REFERENCE EXAMPLE 29

2,3,4,5-tetrahydro-benzo[b](1,4)oxazepine-4-one

A mixture of which 1-ethyl-3-[3-(dimethylamino)propyl]carbodiimide hydrochloride (1.06 g) had been added to methylene chlorid (50 ml) solution of the compound (969 mg) prepared in above Reference example 28 was stirred for 150 minutes. The reactive mixture to which ice water had been added was extracted by methylene chlorid. The organic layer sequentially washed with 1N hydrochloric acid, saturated sodium bicarbonate solution, and saturated brine was concentrated after drying with sulfuric anhydride magnesium. The obtained residue was purified by silica gel column chromatography (n-hexane:ethyl acetate=1:1). A title compound (481 mg) having the following physical properties values was obtained.

TLC:Rf 0.26 (n-hexane:ethyl acetate=1:1);
NMR(CDCl$_3$):δ 2.86 (m, 2H), 4.47 (m, 2H), 7.01 (m, 4H), 7.75 (s, 1H).

REFERENCE EXAMPLE 30

2,3,4,5-tetrahydro-benzo[b](1,4) oxazepine

The compound prepared in Reference example 30(465 mg) was added to tetrahydrofuran (10 ml) suspension of lithium hydride aluminum (324 mg) under reflux, which was refluxed for 1 hour. 2N sodium hydroxide solution (1.5 ml) was added to the reactive mixture stored in ice, and was filtered. The filtrate was concentrated. A title compound (424 mg) having the following physical properties values was obtained.

TLC:Rf 0.40 (n-hexane:ethyl acetate=2:1);
NMR(CDCl$_3$):δ 2.00 (m, 2H), 3.24 (m, 2H), 3.70 (m, 1H), 4.09 (m, 2H), 6.72 (dd, J=7.55, 1.79 Hz, 1H), 6.77 (td, J=7.55, 1.65 Hz, 1H), 6.87 (td, J=7.42 Hz, 1H), 6.96 (dd, J=7.69, 1.65 Hz, 1H)

EXAMPLE 43(1)-EXAMPLE 43(22)

Compounds of the present invention having the following physical properties values were obtained by operating as well as the method represented in Examples 1, 19 and 32, using the compound prepared in the Reference example 30 and the corresponding compound

EXAMPLE 43(1)

N-(4-fluorobenzyl)-2,3,4,5-tetrahydro-benzo[b](1,4)oxazepine-5-carboxamide

TLC:Rf 0.33 (ethyl acetate: n-hexane=2:3);
NMR (DMSO-d$_6$):δ 1.88 (m, 2H), 3.62 (m, 2H), 4.00 (m, 2H), 4.17 (d, J=5.77 Hz, 2H), 6.45 (t, J=5.91 Hz, 1H), 7.15 (m, 8H).

EXAMPLE 43(2)

N-phenyl-2,3,4,5-tetrahydro-benzo[b](1,4)oxazepine-5-carboxamide

TLC:Rf 0.30 (n-hexane:ethyl acetate=3:1);
NMR (CD$_3$OD):δ 7.35-7.11 (m, 8H), 7.04-6.97 (m, 1H), 4.05 (brs, 2H), 3.81 (brs, 2H), 2.08-1.99 (m, 2H).

EXAMPLE 43(3)

N-(4-fluorobenzyl )-8-fluoro-2,3,4,5-tetrahydro-benzo[b](1,4)oxazepine-5-carboxamide TLC:Rf 0.22 (ethyl acetate: n-hexane=1:2);
NMR (DMSO-d$_6$):δ 1.89 (m, 2H), 3.61 (m, 2H), 4.03 (m, 2H), 4.15 (d, J=5.77 Hz, 2H), 6.55 (t, J=5.77 Hz, 1H), 6.90 (m, 2H), 7.10 (m, 2H), 7.23 (m, 3H).

EXAMPLE 43(4)

N-[3-[ethyl(phenyl)amino]propyl]-2,3,4,5-tetrahydro-benzo[b](1,4)oxazepine-5-carboxamide TLC:Rf 0.35 (ethyl acetate: n-hexane=1:1);
NMR (DMSO-d$_6$):δ 1.03 (t, J=7.00 Hz, 3H), 1.61 (m, 2H), 1.89 (m, 2H), 3.05 (q, J=6.32 Hz, 2H), 3.17 (m, 2H), 3.28 (m, 2H), 3.61 (m, 2H), 4.00 (m, 2H), 5.90 (t, J=5.49 Hz, 1H), 6.55 (m, 3H), 7.11 (m, 6H).

EXAMPLE 43(5)

N-[3-[ethyl(phenyl)amino]propyl]-8-fluoro-2,3,4,5-tetrahydro-benzo[b](1,4) oxazepine-5-carboxamide TLC: Rf 0.39 (ethyl acetate: n-hexane=1:1);
NMR (DMSO-d$_6$):δ 1.03 (t, J=7.00 Hz, 3H), 1.61 (m, 2H), 1.89 (m, 2H), 3.04 (m, 2H), 3.17 (m, 2H), 3.28 (m, 2H), 3.60 (m, 2H), 4.03 (m, 2H), 5.99 (t, J=5.77 Hz, 1H), 6.52 (t, J=7.14 Hz, 1H), 6.59 (d, J=7.97 Hz, 2H), 6.90 (m, 2H), 7.10 (m, 2H), 7.19 (m, 1H).

EXAMPLE 43(6)

N-[(1S)-1-[ethyl(4-fluorophenyl)aminocarbonyl]ethyl]-2,3,4,5-tetrahydro-benzo[b](1,4)oxazepine-5-carboxamide TLC:Rf 0.38 (n-hexane:ethyl acetate=1:1);
NMR (DMSO-$d_6$):δ 1.01 (m, 6H), 1.91 (m, 2H), 3.64 (m, 4H), 4.04 (m, 2H), 4.22 (m, 1H), 5.37 (m, 1H), 7.06 (m, 2H), 7.24 (m, 4H), 7.36 (m, 2H).

EXAMPLE 43(7)

N-[ethyl (4-fluorophenyl)aminocarbonylmethyl]-2,3,4,5-tetrahydro-benzo[b](1,4)oxazepine-5-carboxamide TLC: Rf 0.24 (n-hexane:ethyl acetate=1:1);
NMR (DMSO-$d_6$):δ 1.01 (t, J=7.14 Hz, 3H), 1.91 (m, 2H), 3.61 (m, 6H), 4.04 (m, 2H), 5.53 (m, 1H), 7.05 (m, 2H), 7.27 (m, 6H).

EXAMPLE 43(8)

N-[2-ethyl(4-fluorophenyl )amino]ethyl]-2,3,4,5-tetrahydro-benzo[b](1,4)oxazepine-5-carboxamide TLC:Rf 0.41 (n-hexane:ethyl acetate=1:1);
NMR (DMSO-$d_6$):δ 1.04 (t, J=7.05 Hz, 3H), 1.92 (m, 2H), 3.22 (m, 6H), 3.65 (m, 2H), 4.02 (m, 2H), 5.60 (m, 1H), 6.72 (m, 2H), 6.92 (m, 2H), 7.01 (m, 2H), 7.16 (m, 2H).

EXAMPLE 43(9)

N-(1-phenylpiperidin-4-yl )-2,3,4,5-tetrahydro-benzo[b](1,4)oxazepine-5-carboxamide TLC:Rf 0.35 (n-hexane:ethyl acetate=1:1);
NMR (DMSO-$d_6$):δ 1.47 (m, 2H), 1.74 (dd, J=12.09, 2.47 Hz, 2H), 1.88 (m, 2H), 2.73 (m, 2H), 3.64 (m, 5H), 4.00 (m, 2H), 5.69 (d, J=7.69 Hz, 1H), 6.70 (t, J=7.14 Hz, 1H), 6.88 (d, J=8.52 Hz, 2H), 7.01 (m, 2H), 7.15 (m, 4H).

EXAMPLE 43(10)

N-[3-[ethyl(4-fluorophenyl)amino]propyl]-2,3,4,5-tetrahydro-benzo[b](1,4)oxazepine-5-carboxamide Free body:
TLC: Rf 0.36 (n-hexane:ethyl acetate=1:1);
NMR (DMSO-$d_6$):δ 1.00 (t, J=7.00 Hz, 3H), 1.58 (m, 2H), 1.88 (m, 2H), 3.04 (q, J=6.32 Hz, 2H), 3.13 (m, 2H), 3.24 (q, J=6.96 Hz, 2H), 3.61 (m, 2H), 4.01 (m, 2H), 5.88 (m, 1H), 6.58 (m, 2H), 6.94 (m, 2H), 7.04 (m, 2H), 7.19 (m, 2H).
Hydrochloride:
TLC:Rf 0.64 (n-hexane:ethyl acetate=1:2);
NMR (DMSO-$d_6$):δ 1.07 (t, J=7.05 Hz, 3H), 1.64 (m, 2H), 1.91 (m, 2H), 3.07 (t, J=6.59 Hz, 2H), 3.39 (m, 4H), 3.64 (m, 2H), 4.02 (m, 2H), 5.67 (m, 1H), 7.03 (m, 2H), 7.19 (m, 4H), 7.46 (m, 2H).

EXAMPLE 43(11)

N-[(2S)-1-[ethyl(4-fluorophenyl)amino]-2-propyl]-2,3,4,5-tetrahydro-benzo[b](1,4)oxazepine-5-carboxamide Free body:
TLC:Rf 0.53 (n-hexane:ethyl acetate=1:1);
NMR (DMSO-$d_6$):δ 1.01 (t, J=6.96 Hz, 3H), 1.05 (d, J=6.77 Hz, 3H), 1.90 (m, 2H), 3.07 (dd, J=14.46, 6.96 Hz, 1H), 3.27 (m, 3H), 3.64 (m, 2H), 3.99 (m, 3H), 5.23 (m, 1H), 6.73 (m, 2H), 6.94 (m, 4H), 7.14 (m, 2H).
Hydrochloride:
TLC:Rf 0.71 (n-hexane:ethyl acetate=1:2);
NMR (DMSO-$d_6$):δ 1.02 (t, J=7.05 Hz, 3H), 1.06 (d, J=6.59 Hz, 3H), 1.91 (m, 2H), 3.14 (dd, J=14.28, 6.59 Hz, 1H), 3.31 (m, 3H), 3.64 (m, 2H), 3.98 (m, 3H), 5.30 (m, 1H), 6.94 (m, 6H), 7.14 (m, 2H).

EXAMPLE 43(12)

N-(1-phenylpiperidin-4-yl)-8-fluoro-2,3,4,5-tetrahydro-benzo[b](1,4)oxazepine-5-carboxamide TLC: Rf 0.37 (n-hexane:ethyl acetate=1:1);
NMR (DMSO-$d_6$):δ 1.48 (m, 2H), 1.72 (m, 2H), 1.89 (m, 2H), 2.73 (m, 2H), 3.63 (m, 5H), 4.03 (m, 2H), 5.82 (d, J=7.69 Hz, 1H), 6.70 (t, J=7.14 Hz, 1H), 6.85 (m, 4H), 7.16 (m, 3H).

EXAMPLE 43(13)

N-[(1S)-1-[ethyl(4-fluorophenyl)aminocarbonyl]ethyl]-8-fluoro-2,3,4,5-tetrahydro-benzo[b](1,4)oxazepine-5-carboxamide TLC:Rf 0.37 (n-hexane:ethyl acetate=1:1);
NMR (DMSO-$d_6$):δ 0.96 (m, 6H), 1.89 (m, 2H), 3.57 (m, 4H), 4.08 (m, 3H), 5.80 (d, J=6.22 Hz, 1H), 6.93 (m, 2H), 7.32 (m, 5H).

EXAMPLE 43(14)

N-[3-[ethyl(4-fluorophenyl)amino]propyl]-8-fluoro-2,3,4,5-tetrahydro-benzo[b](1,4)oxazepine-5-carboxamide TLC:Rf 0.35 (n-hexane:ethyl acetate=1:1);
NMR (DMSO-$d_6$):δ 1.01 (t, J=6.96 Hz, 3H), 1.58 (m, 2H), 1.89 (m, 2H), 3.03 (m, 2H), 3.13 (m, 2H), 3.24 (q, J=6.96 Hz, 2H), 3.59 (s, 2H), 4.03 (m, 2H), 5.97 (t, J=5.31 Hz, 1H), 6.58 (m, 2H), 6.92 (m, 4H), 7.19 (m, 1H).

EXAMPLE 43(15)

5-carbamoyl-8-fluoro-2,3,4,5-tetrahydro-benzo[b](1,4)oxazepine

TLC:Rf 0.21 (n-hexane:ethyl acetate=1:2);
NMR (DMSO-$d_6$):δ 1.89 (m, 2H), 3.57 (m, 2H), 4.04 (m, 2H), 5.83 (m, 2H), 6.86 (m, 2H), 7.22 (m, 1H).

EXAMPLE 43(16)

N-(2,4-difluorobenzyl)-8-fluoro-2,3,4,5-tetrahydro-benzo[b](1,4)oxazepine-5-carboxamide TLC:Rf 0.50 (n-hexane:ethyl acetate=1:1);
NMR(DMSO-$d_6$):δ 1.89 (m, 2H), 3.61 (m, 2H), 4.04 (m, 2H), 4.18 (d, J=5.68 Hz, 2H), 6.54 (m, 1H), 6.92 (m, 2H), 7.03 (m, 1H), 7.15 (ddd, J=10.62, 9.34, 2.56 Hz, 1H), 7.28 (m, 2H).

EXAMPLE 43(17)

N-(3,4-difluorobenzyl)-8-fluoro-2,3,4,5-tetrahydro-benzo[b](1,4)oxazepine-5-carboxamide TLC:Rf 0.41 (n-hexane:ethyl acetate=1:1);
NMR (DMSO-$d_6$):δ 1.88 (m, 2H), 3.60 (m, 2H), 4.03 (m, 2H), 4.14 (d, J=5.86 Hz, 2H), 6.59 (t, J=5.77 Hz, 1H), 6.92 (m, 2H), 7.04 (m, 1H), 7.26 (m, 3H).

EXAMPLE 43(18)

N-(4-fluoro-2-trifluoromethylbenzyl)-8-fluoro-2,3,4,5-tetrahydro-benzo[b](1,4)oxazepine-5-carboxamide TLC:Rf 0.59 (n-hexane:ethyl acetate=1:1);
NMR (DMSO-$d_6$):δ 1.92 (m, 2H), 3.61 (m, 2H), 4.06 (m, 2H), 4.33 (d, J=5.13 Hz, 2H), 6.61 (m, 1H), 6.94 (m, 2H), 7.34 (m, 1H), 7.52 (m, 3H).

EXAMPLE 43(19)

N-(4-fluoro-3-trifluoromethylbenzyl)-8-fluoro-2,3,4,5-tetrahydro-benzo[b](1,4)oxazepine-5-carboxamide TLC:Rf 0.42 (n-hexane:ethyl acetate=1:1);
NMR (DMSO-$d_6$):δ 1.88 (m, 2H), 3.60 (m, 2H), 4.03 (m, 2H), 4.20 (d, J=5.86 Hz, 2H), 6.65 (m, 1H), 6.92 (m, 2H), 7.24 (m, 1H), 7.42 (m, 1H), 7.57 (m, 2H).

EXAMPLE 43(20)

N-(2-chloro-4-fluorobenzyl)-8-fluoro-2,3,4,5-tetrahydro-benzo[b](1,4) oxazepine-5-carboxamide TLC:Rf 0.50 (n-hexane:ethyl acetate=1:1);
NMR (DMSO-$d_6$):δ 1.89 (m, 2H), 3.61 (m, 2H), 4.05 (m, 2H), 4.20 (d, J=5.68 Hz, 2H), 6.55 (m, 1H), 6.93 (m, 2H), 7.29 (m, 4H).

EXAMPLE 43(21)

N-(3-chloro-4-fluorobenzyl)-8-fluoro-2,3,4,5-tetrahydro-benzo[b](1,4) oxazepine-5-carboxamide TLC: Rf 0.42 (n-hexane:ethyl acetate=1:1);
NMR (DMSO-$d_6$):δ 1.88 (m, 2H), 3.59 (m, 2H), 4.01 (m, 2H), 4.14 (d, J=5.68 Hz, 2H), 6.61 (m, 1H), 6.92 (m, 2H), 7.28 (m, 4H).

EXAMPLE 43(22)

N-(2-benzyloxy-4-chlorobenzyl)-8-fluoro-2,3,4,5-tetrahydro-benzo[b](1,4) oxazepine-5-carboxamide TLC:Rf 0.50 (n-hexane:ethyl acetate=1:1);
NMR (DMSO-$d_6$):δ 1.90 (m, 2H), 3.60 (m, 2H), 4.02 (m, 2H), 4.18 (d, J=5.86 Hz, 2H), 5.14 (s, 2H), 6.27 (m, 1H), 6.92 (m, 3H), 7.11 (m, 2H), 7.34 (m, 6H)

EXAMPLE 44

1-(1H-imidazol-1-ylcarbonothioyl)-2,3,4,5-tetrahydro-1H-1-benzazepine

Thiocarbonyldiimidazole (230 mg) was added to dichloromethane (3 ml) solution of 2,3,4,5-tetrahydro-1H-1-benzazepine (172.4 mg), which was concentrated after the disappearance of the raw material had been confirmed. The obtained residue was purified by silica gel column chromatography (n-hexane:ethyl acetate=5:1). The present compound (285 mg) having the following physical properties values was obtained.

TLC:Rf 0.55(n-hexane:ethyl acetate=3:1);
NMR(CDCl$_3$):δ 1.92 (m, 4H), 2.91 (m, 2H), 3.36 (m, 1H), 5.39 (m, 1H), 7.07 (m, 7H).

EXAMPLE 44(1)

N-(2-cyanoethyl)-2,3,4,5-tetrahydro-1H-1-benzazepine-1-carbothioamide

A present compound having the following physical properties values was obtained by operating as well as the method represented in Example 44, using the corresponding compound TLC: Rf 0.18 (n-hexane:ethyl acetate=4:1);
NMR(CDCl$_3$):δ 1.38 (m, 1H), 1.79 (m, 1H), 2.00 (m, 1H), 2.25 (m, 1H), 2.84 (m, 5H), 3.69 (m, 1H), 3.90 (m, 1H), 5.31 (m, 1H), 5.74 (s, 1H), 7.27 (m, 4H).

EXAMPLE 45

5-oxo-N-phenyl-2,3,4,5-tetrahydro-1H-1-benzazepine-1-carboxamide

A mixture of which triethylamine (0.51 mL) and sulfur trioxide/pyridine complex (583 mg) had been added to dimethyl sulphoxide (2 mL) solution of the compound (345 mg) prepared in Example 2 was stirred at room temperature for 5 hours. The reactive mixture to which water had been added was extracted by ethyl acetate. The organic layer sequentially washed with 1N hydrochloric acid, saturated sodium bicarbonate solution, and saturated brine was concentrated under reduced pressure after drying with sulfuric anhydride magnesium. The present compound having the following physical properties values was obtained.

TLC:Rf 0.62 (n-hexane:ethyl acetate=2:1);
NMR(CDCl$_3$):δ 7.97 (dd, J=7.5, 1.5 Hz, 1H), 7.63 (dt, J=1.5, 7.5 Hz, 1H), 7.50-7.40 (m, 2H), 7.32-7.22 (m, 4H), 7.06-7.00 (m, 1H), 6.37 (bs, 1H), 4.20-3.80 (b, 2H), 2.80-2.74 (m, 2H), 2.17-2.04 (m, 2H).

FORMULATION EXAMPLE

The following components were admixed in conventional method and punched out to obtain 100 tablets each containing 50 mg of active ingredient.

| | |
|---|---|
| 1-(4-hydroxyphenyl)carbamoly-2,3,4,5-tetrahydro-1H-1-benzazepine | 5.0 g |
| Carboxymethyl cellulose calcium | 0.2 g |
| Magnesium stearate | 0.1 g |
| Microcrystalline cellulose | 4.7 g |

The invention claimed is:

1. A compound represented by formula (I-a):

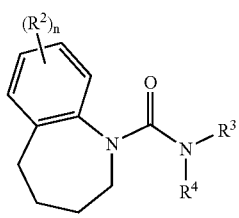

wherein $R^2$ represents (1) C1-8 alkyl or (2) a halogen atom;
$R^3$ represents (1) ring B or (2) a C1-8 alkyl which is substituted by 1-5 group(s) selected from ring B or $CONR^6R^7$;
$R^4$ represents (1) a hydrogen atom or (2) C1-8 alkyl group;
n=0 or 1;
ring B represents C5-8 monocyclic carbocyclic ring which may be substituted by 1-2 group(s) selected from (1) C1-8 alkyl, (2) $OR^5$, or (3) a halogen atom;
$R^5$ represents (1) a hydrogen atom or (2) C1-8 alkyl;
$R^6$ and $R^7$ each independently represents (1) a hydrogen atom or (2) $-D^1-D^2$, wherein $D^1$ represents a single bond and $D^2$ represents (a) C1-8 alkyl which may be substituted by ring C or (b) ring C;
ring C represents benzene or cyclopropane which may be substituted by 1-2 group(s) selected from C1-8 alkyl or a halogen atom, or a pharmaceutically acceptable salt thereof.

2. A method for treatment against irritable bowel syndrome, comprising administering a compound represented by formula (I-a):

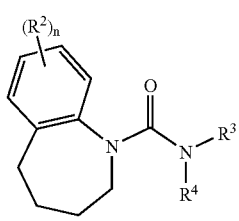

wherein $R^2$ represents (1) C1-8 alkyl or (2) a halogen atom;
$R^3$ represents (1) ring B or (2) a C1-8 alkyl which is substituted by 1-5 group (s) selected from ring B or $CONR^6R^7$;
$R^4$ represents (1) a hydrogen atom or (2) C1-8 alkyl group;
n=0 or 1;
ring B represents C5-8 monocyclic carbocyclic ring which may be substituted by 1-2 group(s) selected from (1) C1-8 alkyl, (2) $OR^5$, or (3) a halogen atom;
$R^5$ represents (1) a hydrogen atom or (2) C1-8 alkyl;
$R^6$ and $R^7$ each independently represents (1) a hydrogen atom or (2) $-D^1-D^2$, wherein $D^1$ represents a single bond and $D^2$ represents (a) C1-8 alkyl which may be substituted by ring C or (b) ring C;
ring C represents benzene or cyclopropane which may be substituted by 1-2 groups(s) selected from C1-8 alkyl or a halogen atom,
or a pharmaceutically acceptable salt thereof.

3. A pharmaceutical composition, comprising the compound represented by formula (I-a) according to claim 1, or a pharmaceutically acceptable salt thereof, and a pharmaceutically acceptable carrier.

4. The compound according to claim 1, wherein the compound is selected from the group consisting of
1-phenylcarbamoyl-2,3,4,5-tetrahydro-1H-1-benzazepine,
8-fluoro-1-phenylcarbamoyl-2,3,4,5-tetrahydro-1H-benzazepine,
1-(4-methoxyphenylcarbamoyl)-2,3,4,5-tetrahydro-1H-1-benzazepine,
1-(4-fluorophenylcarbamoyl)-2,3,4,5-tetrahydro-1H-1-benzazepine,
1-benzylcarbamoyl-2,3,4,5-tetrahydro-1H-1-benzazepine,
1-(2-chlorophenylcarbamoyl)-2,3,4,5-tetrahydro-1H-1-benzazepine,
1-(3-chlorophenylcarbamoyl)-2,3,4,5-tetrahydro-1H-1-benzazepine,
1-(4-chlorophenylcarbamoyl)-2,3,4,5-tetrahydro-1H-1-benzazepine,
1-(2,3-dichlorophenylcarbamoyl)-2,3,4,5-tetrahydro-1H-1-benzazepine,
1-(2,4-dichlorophenylcarbamoyl)-2,3,4,5-tetrahydro-1H-1-benzazepine,
1-(2,6-dichlorophenylcarbamoyl)-2,3,4,5-tetrahydro-1H-1-benzazepine,
1-(2,5-dichlorophenylcarbamoyl)-2,3,4,5-tetrahydro-1H-1-benzazepine,
1-(3,4-dichlorophenylcarbamoyl)-2,3,4,5-tetrahydro-1H-1-benzazepine,
1-(3,5-dichlorophenylcarbamoyl)-2,3,4,5-tetrahydro-1H-1-benzazepine,
1-cyclohexylcarbamoyl-2,3,4,5-tetrahydro-1H-1-benzazepine,
1-(4-methylphenylcarbamoyl)-2,3,4,5-tetrahydro-1H-1-benzazepine,
1-cyclopentylcarbamoyl-2,3,4,5-tetrahydro-1H-1-benzazepine,
8-methyl-1-phenylcarbamoyl-2,3,4,5-tetrahydro-1H-1-benzazepine,
1-(4-bromophenylcarbamoyl)-2,3,4,5-tetrahydro-1H-1-benzazepine,
7-chloro-1-phenylcarbamoyl-2,3,4,5-tetrahydro-1H-1-benzazepine,
1-(2-cyclohexylethylcarbamoyl)-2,3,4,5-tetrahydro-1H-1-benzazepine,
1-cyclohexylmethylcarbamoyl-2,3,4,5-tetrahydro-1H-1-benzazepine,
7-methyl-1-phenylcarbamoyl-2,3,4,5-tetrahydro-1H-1-benzazepine,
9-methyl-1-phenylcarbamoyl-2,3,4,5-tetrahydro-1H-1-benzazepine, 1-(4-hydroxyphenylcarbamoyl)-2,3,4,5-tetrahydro-1H-1-benzazepine,
1-(3-hydroxyphenylcarbamoyl)-2,3,4,5-tetrahydro-1H-1-benzazepine,
1-(2-hydroxyphenylcarbamoyl)-2,3,4,5-tetrahydro-1H-1-benzazepine,
1-(3-hydroxy-4-methoxyphenylcarbamoyl)-2,3,4,5-tetrahydro-1H-1-benzazepine,
1-(4-hydroxyphenylcarbamoyl)-8-methyl-2,3,4,5-tetrahydro-1H-1-benzazepine,
1-(3-chloro-4-hydroxyphenylcarbamoyl)-2,3,4,5-tetrahydro-1H-1-benzazepine,
1-(2-chloro-4-hydroxyphenylcarbamoyl)-2,3,4,5-tetrahydro-1H-1-benzazepine,
1-(4-hydroxy-2-methoxyphenylcarbamoyl)-2,3,4,5-tetrahydro-1H-1-benzazepine,
1-(2-fluoro-4-hydroxyphenylcarbamoyl)-2,3,4,5-tetrahydro-1H-1-benzazepine,
1-(4-hydroxy-2-methylphenylcarbamoyl)-2,3,4,5-tetrahydro-1H-1-benzazepine,
1-(4-hydroxy-3-methylphenylcarbarmoyl)-2,3,4,5-tetrahydro-1H-1-benzazepine,
1-(3-fluoro-4-hydroxyphenylcarbamoyl)-2,3,4,5-tetrahydro-1H-1-benzazepine,
1-(4-hydroxyphenylcarbamoyl)-7-methyl-2,3,4,5-tetrahydro-1H-1-benzazepine,
N-phenyl-6-methyl-2,3,4,5-tetrahydro-1H-1-benzazepine-1-carboxamide,
7-fluoro-N-phenyl-2,3,4,5-tetrahydro-1H-1-benzazepine-1-carboxamide,
8-fluoro-N-(4-fluorobenzyl)-2,3,4,5-tetrahydro-1H-1-benzazepine-1-carboxamide,
N-benzyl-8-fluoro-2,3,4,5-tetrahydro-1H-1-benzazepine-1-carboxamide,
N-benzyl-7-fluoro-2,3,4,5-tetrahydro-1H-1-benzazepine-1-carboxamide,
7-fluoro-N-(4-fluorobenzyl)-2,3,4,5-tetrahydro-1H-1-benzazepine-1-carboxamide,
9-bromo-7-methyl-N-phenyl-2,3,4,5-tetrahydro-1H-1-benzazepine-1-carboxamide,
N-(4-hydroxyphenyl)-2,3-dihydro-1H-1-1-benzazepine-1-carboxamide,
N-(4-fluorobenzyl)-2,3,4,5-tetrahydro-1H-1-benzazepine-1-carboxamide,
N-(4-methoxybenzyl)-2,3,4,5-tetrahydro-1H-1-benzazepine-1-carboxamide,
N-cycloheptyl-2,3,4,5-tetrahydro-1H-1-benzazepine-1-carboxamide,
N-cyclooctyl-2,3,4,5-tetrahydro-1H-1-benzazepine-1-carboxamide,
N-(4-t-butylbenzyl)-2,3,4,5-tetrahydro-1H-1-benzazepine-1-carboxamide,
N-(3-phenylpropyl)-2,3,4,5-tetrahydro-1H-1-benzazepine-1-carboxamide,
N-(4-phenylbutyl)-2,3,4,5-tetrahydro-1H-1-benzazepine-1-carboxamide,
N-[ethyl(4-fluorophenyl)aminocarbonylmethyl]-2,3,4,5-tetrahydro-1H-1-benzazepine-1-carboxamide,
N-[ethyl(3-fluorophenyl)aminocarbonylmethyl]-2,3,4,5-tetrahydro-1H-1-benzazepine-1-carboxamide,
N-[isopropyl(phenyl)aminocarbonylmethyl]-2,3,4,5-tetrahydro-1H-1-benzazepine-1-carboxamide,
N-[benzyl(pbenyl)aminocarbonylmethyl]-2,3,4,5-tetrahydro-1H-1-benzazepine-1-carboxamide,
N-[ethyl(2-fluorophenyl)aminocarbonylmethyl]-2,3,4,5-tetrahydro-1H-1-benzazepine-1-carboxamide,
N-[ethyl(4-fluorophenyl)aminocarbonylmethyl]-7-fluoro-2,3,4,5-tetrahydro-1H-1-benzazepine-1-carboxamide,
N-(2,6-dimethylbenzyl)-2,3,4,5-tetrahydro-1H-1-benzazepine-1-carboxamide,
N-(1-methyl-1-phenylethyl)-2,3,4,5-tetrahydro-1H-1-benzazepine-1-carboxamide,
N-[1-(4-chlorophenyl)-1-methylethyl]-2,3,4,5-tetrahydro-1H-1-benzazepine-1-carboxamide,
N-{(1S)-[ethyl(4-fluorophenyl)aminocarbonyl]ethyl}-2,3,4,5-tetrahydro-1H-1-benzazepine-1-carboxamide,
N-{2-[ethyl(4-fluorophenyl)aminocarbonyl]ethyl}-2,3,4,5-tetrahydro-1H-1-benzazepine-1-carboxamide,
N-[(1R)-1-[ethyl(4-fluorophenyl)aminocarbonyl]ethyl]-2,3,4,5-tetrahydro-1H-1-benzazepine-1-carboxamide,
N-{[t-butyl(4-fluorophenyl)amino]carbonylmethyl}-2,3,4,5-tetrahydro-1H-1-benzazepine-1-carboxamide,
N-{2-[cyclopropyl(4-fluorophenyl)aminocarbonyl]ethyl}-2,3,4,5-tetrahydro-1H-1-benzazepine-1carboxamide,
N-{1-[ethyl(4-fluorophenyl)aminocarbonyl]-2-phenylethyl}-2,3,4,5-tetrahydro-1H-1-benzazepine-1-carboxamide,
cyclopropyl(4-fluorophenyl)aminocarbonylmethyl-2,3,4,5-tetrahydro-1H-1-benzazepine-1-carboxamide,
N-(2-fluorobenzyl)-2,3,4,5-tetrahydro-1H-1-benzazepine-1-carboxamide,
N-(3-fluorobenzyl)-2,3,4,5-tetrahydro-1H-1-benzazepine-1-carboxamide,
N-(2-chlorobenzyl)-2,3,4,5-tetrahydro-1H-1-benzazepine-1-carboxamide,
N-(3-chlorobenzyl)-2,3,4,5-tetrahydro-1H-1-benzazepine-1-carboxamide,
N-(4-chlorobenzyl)-2,3,4,5-tetrahydro-1H-1-benzazepine-1-carboxamide,
N-(2-methoxybenzyl)-2,3,4,5-tetrahydro-1H-1-benzazepine-1-carboxamide,
N-(3-methoxybenzyl)-2,3,4,5-tetrahydro-1H-1-benzazepine-1-carboxamide,
N-(2-methylbenzyl)-2,3,4,5-tetrahydro-1H-1-benzazepine-1-carboxamide,
N-(3-methylbenzyl)-2,3,4,5-tetrahydro-1H-1-benzazepine-1-carboxamide,
N-(4-methylbenzyl)-2,3,4,5-tetrahydro-1H-1-benzazepine-1-carboxamide,
N-(2,3-difluorobenzyl)-2,3,4,5-tetrahydro-1H-1-benzazepine-1-carboxamide,
N-(2,4-difluorobenzyl)-2,3,4,5-tetrahydro-1H-1-benzazepine-1-carboxamide,
N-(2,5-difluorobenzyl)-2,3,4,5-tetrahydro-1H-1-benzazepine-1-carboxamide,
N-(2,6-difluorobenzyl)-2,3,4,5-tetrahydro-1H-1-benzazepine-1-carboxamide,
N-(3,5-difluorobenzyl)-2,3,4,5-tetrahydro-1H-1-benzazepine-1-carboxamide,
N-(3,4-difluorobenzyl)-2,3,4,5-tetrahydro-1H-1-benzazepine-1-carboxamide,
1-(2-methylcyclohexylcarbamoyl)-2,3,4,5-tetrahydro-1H-1-benzazepine,
1-(3-methylcyclohexylcarbamoyl)-2,3,4,5-tetrahydro-1H-1-benzazepine,
1-(4-methylcyclohexylcarbamoyl)-2,3,4,5-tetrahydro-1H-1-benzazepine,
1-[(1R)-1-(4-methylphenyl)ethylcarbamoyl]-2,3,4,5-tetrahydro-1H-1-benzazepine,
1-[1-(4-fluorophenyl)ethylcarbarmoyl]-2,3,4,5-tetrahydro-1H-1-benzazepine, N-(4-hydroxyphenyl)-8-fluoro-2,3,4,5-tetrahydro-1H-1-benzazepine-1-carboxamide,
N-(4-hydroxyphenyl)-9-methyl-2,3,4,5-tetrahydro-1H-1-benzazepine-1-carboxamide,
N-(4-hydroxyphenyl)-6-methyl-2,3,4,5-tetrahydro-1H-1-benzazepine-1-carboxamide,
7-fluoro-N-(4-hydroxyphenyl)-2,3,4,5-tetrahydro-1H-1-benzazepine-1-carboxamide,
6-fluoro-N-(4-hydroxyphenyl)-2,3,4,5-tetrahydro-1H-1-benzazepine-1-carboxamide,
N-(4-hydroxybenzyl)-2,3,4,5-tetrahydro-1H-1-benzazepine-1-carboxamide,
8-fluoro-N-(4-hydroxybenzyl)-2,3,4,5-tetrahydro-1H-1-benzazepine-1-carboxamide,
7-fluoro-N-(4-hydroxybenzyl)-2,3,4,5-tetrahydro-1H-1-benzazepine-1-carboxamide, and
N-(4-hydroxyphenyl)-5-methyl-2,3-dihydro-1H-1-benzazepine-1-carboxamide.

* * * * *